United States Patent
Weier et al.

(10) Patent No.: US 6,426,360 B1
(45) Date of Patent: *Jul. 30, 2002

(54) 4,5-SUBSTITUTED IMIDAZOLYL COMPOUNDS FOR THE TREATMENT OF INFLAMMATION

(75) Inventors: Richard M Weier, Lake Bluff; Paul W Collins, Deerfield; Michael A Stealey, Libertyville; Thomas E Barta, Evanston; Renee M Huff, Park Ridge, all of IL (US)

(73) Assignee: G D Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,033

(22) Filed: May 15, 2000

Related U.S. Application Data

(63) Continuation of application No. 09/218,208, filed on Dec. 22, 1998, now abandoned, which is a continuation of application No. 08/765,865, filed as application No. PCT/US95/09505 on Jul. 27, 1995, now abandoned, and a continuation-in-part of application No. 08/281,903, filed on Jul. 28, 1994, now Pat. No. 5,620,999.

(51) Int. Cl.$^7$ ............................................. A01N 43/50
(52) U.S. Cl. .................. 514/396; 514/398; 548/254; 548/311.7; 548/342.1; 548/333.5; 548/334.5; 548/337.1; 548/338.1; 548/341.1; 548/342.5; 548/325.5; 548/325.1; 548/345.1; 548/343.5; 548/343.1
(58) Field of Search ............................ 548/343.1, 343.5, 548/345.1, 325.1, 325.5, 333.5, 334.5, 337.1, 338.1, 341.1, 342.5, 342.1, 311.7, 254; 514/396, 398

(56) References Cited

U.S. PATENT DOCUMENTS

| | | | |
|---|---|---|---|
| 3,707,475 A | | 12/1972 | Lombardino |
| 3,901,908 A | * | 8/1975 | Fitzi et al. ............... 546/271 X |
| 3,929,807 A | | 12/1975 | Fitz |
| 4,175,127 A | * | 11/1979 | Bender et al. ........... 424/275 X |
| 4,188,397 A | | 2/1980 | Hill |
| 4,372,964 A | | 2/1983 | Whitney |
| 4,472,422 A | | 9/1984 | Whitney |
| 4,503,065 A | * | 3/1985 | Wilkerson ................... 514/396 |
| 4,576,958 A | | 3/1986 | Wexler |
| 4,686,231 A | | 8/1987 | Bender et al. |
| 4,822,805 A | | 4/1989 | Takasugi et al. |
| 5,620,999 A | * | 4/1997 | Weier et al. ................. 514/398 |

FOREIGN PATENT DOCUMENTS

| | | | |
|---|---|---|---|
| AU | 8665565 | | 11/1986 |
| CH | 0561717 | * | 5/1975 |
| EP | 0032113 | * | 7/1981 |
| EP | 0044486 | * | 1/1982 |
| EP | 372445 | | 6/1990 |
| WO | 94/15932 | * | 7/1994 |
| WO | 95/00501 | * | 1/1995 |

OTHER PUBLICATIONS

Hla et al., *Proc. Natl. Acad. Sci, USA*, 89, 7384 (1992).

Masferrer, et al, *Proc. Natl. Acad. Sci, USA*, 89, 3917 (1992).

Meade et al, *J. Biol. Chem.*, 268, 6610 (1993).

Futaki et al, *Prostaglandins*, 47, 55 (1994).

Sharpe et al, *J. Med. Chem.*, 28, 1188 (1985).

Greenberg et al, *J. Org. Chem.*, 31, 3951 (1966).

van Es et al, *J. Chem. Soc.*, 1363 (1963).

Lombardino et al, *J. Med. Chem.*, 17, 1182 (1974).

* cited by examiner

*Primary Examiner*—Floyd D. Higel
*Assistant Examiner*—Ebenezer Sackey
(74) *Attorney, Agent, or Firm*—McDonnell Boehnen Hulbert & Berghoff

(57) ABSTRACT

A class of compounds is described for treating inflammation and inflammation-related disorders. Compounds of particular interest are defined by Formula

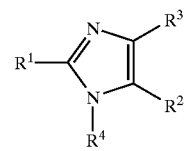

I wherein $R^1$ is selected from lower alkyl, lower haloalkyl, lower hydroxyalkyl, lower alkoxyalkyl, lower alkenyloxyalkyl, mercapto, lower alkylcarbonyl, lower haloalkylcarbonyl, phenylcarbonyl, lower aralkylcarbonyl, lower aralkenyl, lower aryloxyalkyl, lower aralkyloxyalkyl, lower arylsulfonyl, lower aralkylsulfonyl, lower arylthioalkyl, lower heteroarylalkylthioalkyl, and heteroaryl selected from 2-thienyl, 2-furyl, 3-furyl, 2-pyridyl, 4-pyridyl and 2-benzofuryl; wherein $R^2$ and $R^3$ are independently selected from heteroaryl, cycloalkyl and aryl, wherein the heteroaryl, cycloalkyl and aryl radicals are substituted at a substitutable position with one or more radicals selected from hydrido, halo, lower alkylthio, lower alkylsulfinyl, lower alkylsulfonyl, aminosulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, phenylamino and nitro; and wherein $R^4$ is selected from hydrido, lower alkyl and acyl; or a pharmaceutically-acceptable salt thereof.

28 Claims, No Drawings

10
4,5-SUBSTITUTED IMIDAZOLYL COMPOUNDS FOR THE TREATMENT OF INFLAMMATION

This is a continuation of application Ser. No. 09/218,208, filed Dec. 22, 1998, now abandoned, which is a continuation of application Ser. No. 08/765,865, filed Jan. 10, 1997, now abandoned, which is National Phase filing of application Ser. No. PCT/US95/09505, filed Jul. 27, 1995, which is a continuation-in-part of application Ser. No. 08/281,903, filed Jul. 28, 1994, now U.S. Pat. No. 5,620,999.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDS) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel imidazoles disclosed herein are such safe and also effective antiinflammatory agents furthering such efforts. The invention compounds are found to show usefulness in vivo as antiinflammatory agents with minimal side effects. The substituted imidazoles disclosed herein preferably selectively inhibit cyclooxygenase-2 over cyclooxygenase-1.

U.S. Pat. No. 4,822,805, to Takasugi et al., describes pyridyl-imidazoles as antiinflammatory agents. Specifically, 2-[2-methoxy-4-(methylsulfonyl)phenyl-4-methyl-5-(3-pyridyl) imidazole is described.

U.S. Pat. No. 4,188,397, to Hill, describes 2,2-alkyldiylbis(thio)bis(imidazoles) with substituted phenyl radicals at the 4 and 5 positions of the imidazole rings as having antiinflammatory activity. Specifically, imidazoles having phenyl radicals substituted with methoxy, methylthio, trifluoromethylhalo and methylenedioxy are described.

T. Sharpe et al. [*J.Med. Chem.*, 28, 1188 (1985)] describe antiarthritic activity of 4,5-diaryl-2-(substituted thio)-1H-imidazoles.

U.S. Pat. No. 4,686,231, to Bender et al., describes 4,5-diaryl-1H-imidazoles as inhibiting the 5-lipoxygenase pathway for the treatment of arthritis. 1-Methyl-4,5-bis (methoxyphenyl)-2-methylthio-1H-imidazole is specifically described.

Australian publication AU8665565 describes cyano-2,2-bis(imidazoles) as having antihypertensive agents.

WO 93/14082, published Jul. 22, 1993, describes 1-pyridyl-2-phenyl-imidazole derivatives for the treatment of interleukin-1 mediated diseases.

H. Greenberg et al. [*J.Org.Chem.*, 31, 3951 (1966)] describe 4-(2-oxo-5-phenyl-4-imidazolin-4-yl) benzenesulfonamide in a study of the bromination reaction thereof.

T. van Es and O. Backeberg [*J. Chem. Soc.*, 1363 (1963)] describe the synthesis of 4,4'-imidazol-4,5-diyl]bis (benzenesulfonamide) for use in a study of substitution reactions on phenyl radicals.

European publication EP 372,445, published Jun. 13, 1990, describes 4,5-diaryl-1H-imidazoles as having antihypercholesterolemic activity. N-C[[5-(4-Methylsulfonylphenyl)-4-phenyl-1H-imidazol-2-yl]thio] pentyl-N-octyl-N-heptylurea is specifically described. U.S. Pat. No. 5,364,875, to Wilde, describes substituted imidazoles for the treatment of atherosclerosis. U.S. Pat. No. 5,358,946, to Wilde, describes substituted imidazoles for the treatment of atherosclerosis. U.S. Pat. No. 5,310,748, to Billheimer et al., describes substituted imidazoles for the treatment of atherosclerosis. U.S. Pat. No. 5,166,214, to Billheimer et al., describes substituted imidazoles for the treatment of atherosclerosis. T. Maduskuie et al., [*J. Med. Chem.*, 38, 1067 (1995)] describes substituted imidazoles as acyl-CoA:Cholesterol Acyltransferase inhibitors U.S. Pat. No. 4,503,065, to Wilkerson, describes 4,5-diaryl-2-halo-1H-imidazoles as being antiinflammatory. Specifically, 1-(1-ethoxyethyl)-2-fluoro-4,5-bis(4-methylsulfonylphenyl)-1H-imidazole is described.

J. Lombardino (*J. Med. Chem.*, 17, 1182 (1974)) describes trisubstituted imidazoles as being antiinflammatory, and specifically 4,5-bis(4-methoxyphenyl)-2-trifluoromethyl-1H-imidazole. Similarly, U.S. Pat. No. 3,707,475, to Lombardino, describes antiinflammatory 4,5-diarylimidazoles. Specifically, 4-chlorophenyl-5-(4-methylthiophenyl)-2-trifluoromethyl-1H-imidazole is described.

U.S. Pat. No. 4,472,422, to Whitney, describes 4,5-diaryl-1H-imidazole-2-methanamines as having antiinflammatory activity. Specifically, 5-(4-fluorophenyl)-4-(4-methylsulfonylphenyl)-α,α-bis(trifluoromethyl)-1H-imidazole-2-methanamine is described.

U.S. Pat. No. 4,372,964, to Whitney, describes 4,5-diaryl-1H-imidazole-2-methanols as having antiinflammatory activity. Specifically, 5-(4-fluorophenyl)-4-(4-methylsulfonylphenyl)-α,α-bis(trifluoromethyl)-1H-imidazole-2-methanol is described. Additionally, Whitney describes 1-[4,5-diaryl-1H-imidazol-2-yl]-2,2,2-trifluoro-1-ethanones as having antiinflammatory activity. Specifically, 1-[5-(4-fluorophenyl)-4-(4-methylsulfonylphenyl)-1H-imidazol-2-yl]-2,2,2-trifluoro-1-ethanone is described.

U.S. Pat. No. 4,576,958, to Wexler, describes 4-phenyl-5-(4-methylsulfonylphenyl)-1H-imidazoles as having anti-inflammatory activity. Specifically, 4-(4-fluorophenyl)-5-(4-methylsulfonylphenyl)-α,α-bis(trifluoromethyl)-1H-imidazole-2-methanol and 4-(4-fluorophenyl)-5-(4-methylsulfonylphenyl)-α,α-bis(trifluoromethyl)-1H- imidazole-2-methanol, acetate is described. U.S. Pat. No. 4,632,930, to Carini et al., claims cycloalkyl substituted imidazoles, and specifically 4-cyclopentyl-5-(4-methylsulfonyl)-α,α-bis(trifluoromethyl)-1H-imidazole-2-methanol, as having antihypertensive properties.

U.S. Pat. No. 3,901,908, to Fitzi, et al., describes 2-alkyl-4,5-bis(substituted phenyl)-1H-imidazoles. Specifically, 2-tert-butyl-4-(4-methylsulfonylphenyl)-5-phenyl-1H-imidazole is described. French patent 2,081,407 describes 4,5-phenyimidazoles as antiinflammatory agents.

4,5-Diarylimidazoles have been described in WO95/00501, published Jan. 5, 1995, as having antiinflammatory activity.

The invention's imidazolyl compounds are found to show usefulness in vivo as antiinflammatory agents with minimal side effects.

DESCRIPTION OF THE INVENTION

A class of substituted imidazolyl compounds useful in treating inflammation-related disorders is defined by Formula I:

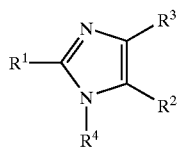

wherein $R^1$ is selected from alkyl, haloalkyl, aralkyl, heterocyclicalkyl, heteroaralkyl, acyl, cyano, mercapto, alkoxy, alkylthio, alkylthioalkyl, alkylsulfonyl, haloalkylsulfonyl, arylsulfonyl, halo, hydroxyalkyl, alkylcarbonyl, arylcarbonyl, aralkylcarbonyl, cyanoalkyl, aralkenyl, aminoalkyl, alkylaminoalkyl, N-arylaminoalkyl, N-alkyl-N-aryl-aminoalkyl, carboxyalkyl, alkoxycarbonylalkyl, alkoxycarbonyl, haloalkylcarbonyl, carboxyl, alkoxyalkyl, alkenyloxyalkyl, aminocarbonyl, alkylaminocarbonyl, alkylaminocarbonylalkyl, heteroaralkoxyalkyl, heteroaryloxyalkyl, heteroarylthioalkyl, heteroarylalkylthioalkyl, aralkoxy, aralkylthio, heteroaralkoxy, heteroaralkylthio, heteroaryloxy, heteroarylthio, arylthioalkyl, arylsulfonyl, aralkylsulfonyl, heteroarylsulfonyl, heteroarylalkylsulfonyl, aryloxyalkyl, arylthio, aryloxy, aralkylthioalkyl, aralkoxyalkyl, alkoxyaralkoxyalkyl, aryl and heteroaryl, wherein the aryl and heteroaryl radicals are optionally substituted at a substitutable position with one or more radicals selected from halo, alkylthio, alkylsulfinyl., alkyl, cyano, haloalkyl, hydroxyl, alkoxy, hydroxyalkyl and haloalkoxy;

wherein $R^2$ and $R^3$ are independently selected from cycloalkyl, cycloalkenyl, heterocyclo and aryl, wherein the cycloalkyl, cycloalkenyl, heterocyclo and aryl radicals are substituted with one or more radicals selected from hydrido, halo, alkylthio, alkylsulfinyl, alkylsulfonyl, aminosulfonyl, haloalkylsulfonyl, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro; and wherein $R^4$ is selected from hydrido, alkyl and acyl;

provided one of $R^2$ and $R^3$ is phenyl substituted with a radical selected from alkylsulfonyl or aminosulfonyl;

further provided $R^1$ is not α,α-bis(trifluoromethyl) methanol, α,α-bis(trifluoromethyl) methanamine, α,α-bis(trifluoromethyl)methanol, acetate ester, or trifluoroacetyl when $R^3$ is 4-methylsulfonylphenyl and when $R^1$ is hydrido; and further provided $R^1$ is not alkyl when $R^3$ is 4-methylsulfonylphenyl and $R^2$ is phenyl optionally substituted with methyl, methoxy or chloro; or a pharmaceutically-acceptable salt thereof.

The phrase "further provided", as used in the above description, is intended to mean that the denoted proviso is not to be considered conjunctive with any of the other provisos.

Compounds of Formula I would be useful for, but not limited. to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis. Such compounds of the invention would be useful in the treatment of asthma, bronchitis, menstrual cramps, tendinitis, bursitis, and skin related conditions such as psoriasis, eczema, burns and dermatitis. Compounds of the invention also would be useful to treat gastrointestinal conditions such as inflammatory bowel disease, Crohn's disease, gastritis, irritable bowel syndrome and ulcerative colitis and for the prevention of colorectal cancer. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, conjunctivitis, swelling occurring after injury, myocardial ischemia, and the like. The compounds were also be useful in the treatment of ophthalmic diseases such as retinitis, retinopathies, uveitis, and of acute injury to the eye tissue. The compounds would also be useful for the treatment of certain central nervous system disorders such as Alzheimer's disease and dementia. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma.

Besides being useful for human treatment, these compounds are also useful for treatment of mammals, including horses, dogs, cats, rats, mice,. sheep, pigs, etc.

The present compounds may also be used in co-therapies, partially or completely, in place of other conventional antiinflammatories, such as together with steroids, NSAIDs, 5-lipoxygenase inhibitors, $LTB_4$ antagonists and $LTA_4$ hydrolase inhibitors.

Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the LTB$_4$ inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

As, illustrated, the imidazoles of Formula II and II' are magnetically and structurally equivalent because of the prototropic tautomeric nature of the acidic hydrogen (A. R. Katritzky and C. W. Rees, "Imidazoles and their Benzo Derivatives" Comprehensive Heterocyclic Chemistry, Vol. 5, 363–365 (1984)]:

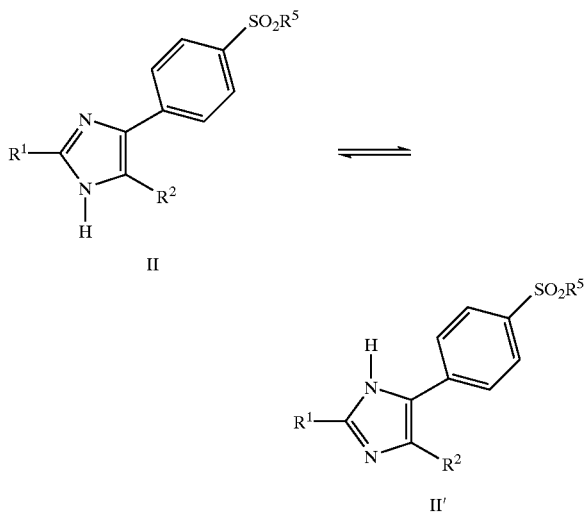

The present invention preferably includes compounds which selectively inhibit cyclooxygenase II over cyclooxygenase I. Preferably, the compounds have a cyclooxygenase II IC$_{50}$ of less than about 0.5 μM, and also have a selectivity ratio of cyclooxygenase II inhibition over cyclooxygenase I inhibition of at least 5, and more preferably of at least 100. Even more preferably, the compounds have a cyclooxygenase I IC$_{50}$ of greater than about 2.5 μM, and more preferably of greater than 50 μM. Such preferred selectivity may indicate an ability to reduce the incidence of common NSAID-induced side effects.

A preferred class of compounds consists of those compounds of Formula I wherein R$^1$ is selected from lower alkyl, lower haloalkyl, lower aralkyl, lower heterocyclicalkyl, lower heteroaralkyl, acyl, cyano, mercapto, lower alkoxy, lower alkylthio, lower alkylthioalkyl, lower alkylsulfonyl, lower haloalkylsulfonyl, lower arylsulfonyl, halo, lower hydroxyalkyl, lower alkoxyalkyl, lower alkenyloxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower haloalkylcarbonyl, carboxyl, aminocarbonyl, lower alkylaminocarbonyl, lower alkylaminocarbonylalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, lower hydroxyl, lower alkoxy, lower hydroxyalkyl and lower haloalkoxy; wherein R$^2$ and R$^3$ are independently selected from heteroaryl, lower cycloalkyl, lower cycloalkenyl, and aryl, wherein the heteroaryl, lower cycloalkyl, lower cycloalkenyl, and aryl radicals are substituted with one or more radicals selected from hydrido, halo, lower alkylthio, lower alkylsulfinyl, lower alkylsulfonyl, aminosulfonyl, lower haloalkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and wherein R$^4$ is selected from hydrido, lower alkyl and acyl; or a pharmaceutically-acceptable salt thereof.

A more preferred class of compounds consists of those compounds of Formula I wherein R$^1$ is selected from lower alkyl, lower haloalkyl, lower hydroxyalkyl, lower alkoxyalkyl, lower alkenyloxyalkyl, mercapto, lower alkylcarbonyl, lower haloalkylcarbonyl, phenylcarbonyl, lower aralkylcarbonyl, lower aralkenyl, lower aryloxyalkyl, lower aralkyloxyalkyl, lower arylsulfonyl, lower aralkylsulfonyl, lower arylthioalkyl, lower heteroarylalkylthioalkyl, and heteroaryl selected from 2-thienyl, 2-furyl, 3-furyl, 2-pyridyl, 4-pyridyl and 2-benzdfuryl; wherein R$^2$ and R$^3$ are independently selected from heteroaryl, cycloalkyl and aryl, wherein the heteroaryl, cycloalkyl and aryl radicals are substituted at a substitutable position with one or more radicals selected from hydrido, halo, lower alkylthio, lower alkylsulfinyl, lower alkylsulfonyl, aminosulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, phenylamino and nitro; and wherein R$^4$ is selected from hydrido, lower-alkyl and acyl; or a pharmaceutically-acceptable salt thereof.

A class of compounds of particular interest consists of those compounds of Formula I wherein R$^1$ is selected from methyl, ethyl, propyl, isopropyl, butyl, isobutyl, tert-butyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, mercapto, hydroxymethyl, hydroxyethyl, methoxymethyl, methoxyethyl, ethoxymethyl, propylenyloxymethyl, methylcarbonyl, trifluoromethylcarbonyl, phenylcarbonyl, benzylcarbonyl, phenylethylcabonyl, phenylpropylcarbonyl, 2-bromobenzylcarbonyl, 2-phenylethenyl, phenoxymethyl, benzyloxymethyl, phenylthiomethyl, quinolylmethylthiomethyl, phenylsulfonyl, benzylsulfonyl, 3-furyl, 2-furyl, 2-benzofuryl; wherein R$^2$ and R$^3$ are independently selected from phenyl, naphthyl, biphenyl, cyclobutyl, cyclopentyl, cyclohexyl, cycloheptyl, cyclohexenyl, benzofuryl, benzodioxolyl, furyl, imidazolyl, thienyl, thiazolyl, pyrrolyl, oxazolyl, isoxazolyl, triazolyl, pyrimidinyl, quinolinyl, benzimidazolyl, indolyl, pyrazolyl and pyridyl, wherein R$^2$ and R$^3$ are substituted at a substitutable position with one or more radicals selected from hydrido, fluoro, chloro, bromo, iodo, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methylsulfonyl, aminosulfonyl, cyano, methoxy, ethoxy, isopropoxy, tert-butoxy, propoxy, butoxy, isobutoxy, pentoxy, methylenedioxy, amino, trifluoromethoxy, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, hydroxyl, nitro, methylsulfinyl, butylsulfinyl, hydroxymethyl, methoxymethyl, ethoxymethyl, methylamino, N,N-dimethylamino, phenylamino, methylthio, ethylthio, propylthio and butylthio; and wherein $R^4$ is selected from methyl, ethyl, hydrido, methylcarbonyl and trifluoromethylcarbonyl; or a pharmaceutically-acceptable salt thereof.

A family of specific compounds of particular interest within Formula I consists of compounds and pharmaceutically-acceptable salts thereof as follows:

5-(3-chlorophenyl)-4-(4-methylsulfonylphenyl)-2-trifluoromethyl-1H-imidazole;
5-(3-chloro-4-methylphenyl)-4-(4-methylsulfonylphenyl)-2-trifluoromethyl-1H-imidazole;
5-(3-fluorophenyl)-4-(4-methylsulfonylphenyl)-2-trifluoromethyl-1H-imidazole;
5-(3-chloro-4-methoxyphenyl)-4-(4-methylsulfonylphenyl)-2-trifluoromethyl-1H-imidazole;
5-(2,4-dichlorophenyl)-4-(4-methylsulfonylphenyl)-2-trifluoromethyl-1H-imidazole;
5-(4-bromophenyl)-4-(4-methylsulfonylphenyl)-2-trifluoromethyl-1H-imidazole;
4-(4-methylsulfonylphenyl)-2-trifluoromethyl-5-(4-trifluoromethylphenyl)-1H-imidazole;
4-(4-methylsulfonylphenyl)-2-trifluoromethyl-5-(4-trifluoromethoxyphenyl)-1H-imidazole;
5-(4-ethylphenyl)-4-(4-methylsulfonylphenyl)-2-trifluoromethyl-1H-imidazole;
5-(4-butylphenyl)-4-(4-methylsulfonylphenyl)-2-trifluoromethyl-1H-imidazole;
5-(4-butoxyphenyl)-4-(4-methylsulfonylphenyl)-2-trifluoromethyl-1H-imidazole;
4-(4-methylsulfonylphenyl)-5-(4-methylthiophenyl)-2-trifluoromethyl-1H-imidazole;
5-(3,5-dichloro-4-methoxyphenyl)-4-(4-methylsulfonylphenyl)-2-trifluoromethyl-1H-imidazole;
5-(3,5-dichloro-4-methylphenyl)-4-(4-methylsulfonylphenyl)-2-trifluoromethyl-1H-imidazole;
5-[4-(4-methylsulfonylphenyl)-2-trifluoromethyl-1H-imidazol-5-yl]-1,3-benzodioxole;
2-(4-chlorophenoxy)methyl-5-(4-chlorophenyl)-4-(4-methylsulfonylphenyl)-1H-imidazole;
5-(4-chlorophenyl)-2-[(4-fluorophenoxy)methyl]-4-(4-methylsulfonylphenyl)-1H-imidazole;
5-(4-chlorophenyl)-4-(4-methylsulfonylphenyl)-2-(phenylthiomethyl)-1H-imidazole;
5-(4-chlorophenyl)-2-[(4-methoxybenzyloxy)methyl]-4-(4-methylsulfonylphenyl)-1H-imidazole;
2-benzyl-5-(4-chlorophenyl)-4-(4-methylsulfonylphenyl)-1H-imidazole;
5-(4-chlorophenyl)-4-(4-methylsulfonylphenyl)-2-(phenylethyl)-1H-imidazole;
5-(4-chlorophenyl)-4-(4-methylsulfonylphenyl)-2-(phenylcarbonyl)-1H-imidazole;
5-(4-chlorophenyl)-4-(4-methylsulfonylphenyl)-2-phenoxymethyl-1H-imidazole;
5-(4-chlorophenyl)-4-(4-methylsulfonylphenyl)-2-(2-phenyl-trans-eth-1-ene)-1H-imidazole;
2-(2-benzofuryl)-5-(4-chlorophenyl)-4-(4-methylsulfonylphenyl)-1H-imidazole;
5-(4-chlorophenyl)-4-(4-methylsulfonylphenyl)-2-(2-furyl)-1H-imidazole;
2-benzylthio-5-(4-chlorophenyl)-4-[4-(methylsulfonyl)phenyl]imidazole;
5-(4-chlorophenyl)-4-[4-(methylsulfonyl)phenyl]-2-(trifluoromethyl)-1H-imidazole;
5-(4-chlorophenyl)-2-(3-furyl)-4-[4-(methylsulfonyl)phenyl]-1H-imidazole;
4-(4-methylsulfonylphenyl)-5-phenyl-2-phenoxymethyl-1H-imidazole;
4-(4-methylsulfonylphenyl)-5-phenyl-2-(2-phenyl-trans-eth-1-ene)-1H-imidazole;
2-(2-benzofuryl)-4-(4-methylsulfonylphenyl)-5-phenyl-1H-imidazole;
2-(2-furyl)-4-(4-methylsulfonylphenyl)-5-phenyl-1H-imidazole;
2-benzylthio-4-[4-(methylsulfonyl)phenyl]-5-phenyl-imidazole;
4-[4-(methylsulfonyl)phenyl]-5-phenyl-2-(trifluoromethyl)-1H-imidazole;
2-(3-furyl)-4-[4-(methylsulfonyl)phenyl]-5-phenyl-1H-imidazole;
4-[5-(3-chlorophenyl)-2-trifluoromethyl-1H-imidazol-4-yl]benzenesulfonamide;
4-[5-(3-chloro-4-methylphenyl)-2-trifluoromethyl-1H-imidazol-4-yl]benzenesulfonamide;
4-[5-(3-fluorophenyl)-2-trifluoromethyl-1H-imidazol-4-yl]benzenesulfonamide;
4-[5-(3-chloro-4-methoxyphenyl)-2-trifluoromethyl-1H-imidazol-4-yl]benzenesulfonamide;
4-[5-(2,4-dichlorophenyl)-2-trifluoromethyl-1H-imidazol-4-yl]benzenesulfonamide;
4-[5-(4-bromophenyl)-2-trifluoromethyl-1H-imidazol-4-yl]benzenesulfonamide;
4-[2-trifluoromethyl-5-(4-trifluoromethylphenyl)-1H-imidazol-4-yl]benzenesulfonamide;
4-[2-trifluoromethyl-5-(4-trifluoromethoxyphenyl)-1H-imidazol-4-yl]benzenesulfonamide;
4-[5-(4-ethylphenyl)-2-trifluoromethyl-1H-imidazol-4-yl]benzenesulfonamide;
4-[5-(4-butylphenyl)-2-trifluoromethyl-1H-imidazol-4yl]benzenesulfonamide;
4-[5-(4-butoxyphenyl)-2-trifluoromethyl-1H-imidazol-4-yl]benzenesulfonamide;
4-[5-(4-methylthiophenyl)-2-trifluoromethyl-1H-imidazol-4-yl]benzenesulfonamide;
4-[5-(3,5-dichloro-4-methoxyphenyl)-2-trifluoromethyl-1H-imidazol-4-yl]benzenesulfonamide;
5-(3,5-dichloro-4-methylphenyl)-2-trifluoromethyl-1H-imidazol-4yl]benzenesulfonamide;
5-[4-(4-aminosulfonylphenyl)-2-trifluoromethyl-1H-imidazol-5-yl]-1,3-benzodioxole;
4-[2-(4-chlorophenoxy)methyl-5-(4-chlorophenyl)-1H-imidazol-4-yl]benzenesulfonamide;

4-[5-(4-chlorophenyl)-2-[(4-fluorophenoxy)methyl]-1H-imidazol-4-yl]benzenesulfonamide;

4-[5-(4-chlorophenyl)-2-(phenylthiomethyl)-1H-imidazol-4-yl]benzenesulfonamide;

4-[5-(4-chlorophenyl)-2-[(4-methoxybenzyloxy)methyl]-1H-imidazol-4-yl]benzenesulfonamide;

4-[2-benzyl-5-(4-chlorophenyl)-1H-imidazol-4-yl]benzenesulfonamide;

4-[5-(4-chlorophenyl)-2-(phenylethyl)-1H-imidazol-4-yl]benzenesulfonamide;

4-[5-(4-chlorophenyl)-2-(phenylcarbonyl)-1H-imidazol-4-yl]benzenesulfonamide;

4-[5-(4-chlorophenyl)-2-phenoxymethyl-1H-imidazol-4-yl]benzenesulfonamide;

4-[5-(4-chlorophenyl)-2-(2-phenyl-trans-eth-1-ene)-1H-imidazol-4-yl]benzenesulfonamide;

4-[2-(2-benzofuryl)-5-(4-chlorophenyl)-1H-imidazol-4-yl]benzenesulfonamide;

4-[5-(4-chlorophenyl)-2-(2-furyl)-1H-imidazol-4-yl]benzenesulfonamide;

4-[2-benzylthio-5-(4-chlorophenyl)-1H-imidazol-4-yl]benzenesulfonamide;

4-[5-(4-chlorophenyl)-2-(trifluoromethyl)-1H-imidazol-4-yl]benzenesulfonamide;

4-[5-(4-chlorophenyl)-2-(3-furyl)-1H-imidazol-4-yl]benzenesulfonamide;

4-[5-phenyl-2-phenoxymethyl-1H-imidazol-4-yl]benzenesulfonamide;

4-[5-phenyl-2-(2-phenyl-trans-eth-1-ene)-1H-imidazol-4-yl]benzenesulfonamide;

4-[2-(2-benzofuryl)-5-phenyl-1H-imidazol-4-yl]benzenesulfonamide;

4-[2-(2-furyl)-5-phenyl-1H-imidazol-4-yl]benzenesulfonamide;

4-[2-benzylthio-5-phenyl-imidazol-4-yl]benzenesulfonamide;

4-[5-phenyl-2-(trifluoromethyl)-1H-imidazol-4-yl]benzenesulfonamide;

4-[2-(3-furyl)-5-phenyl-1H-imidazol-4-yl]benzenesulfonamide;

5-(4-fluorophenyl)-4-(4-methylsulfonylphenyl)-2-trifluoromethyl-1H-imidazole;

5-(4-fluorophenyl)-4-(4-methylsulfonylphenyl)-2-phenoxymethyl-1H-imidazole;

5-(4-fluorophenyl)-4-(4-methylsulfonylphenyl)-2-(2-phenyl-trans-eth-1-ene)-1H-imidazole;

2-(2-benzofuryl)-5-(4-fluorophenyl)-4-(4-methylsulfonylphenyl)-1H-imidazole;

5-(4-fluorophenyl)-2-(2-furyl)-4-(4-methylsulfonylphenyl)-1H-imidazole;

5-(4-fluorophenyl)-2-methyl-4-(4-methylsulfonylphenyl)-1H-imidazole;

5-(4-fluorophenyl)-2-isopropyl-4-(4-methylsulfonylphenyl)-1H-imidazole;

5-(4-fluorophenyl)-2-hydroxymethyl-4-(4-methylsulfonylphenyl)-1H-imidazole;

2-benzylthio-5-(4-fluorophenyl)-4-[4-(methylsulfonyl)phenyl]imidazole;

5-(3-fluoro-4-methoxyphenyl)-4-[4-(methylsulfonyl)phenyl]-2-(trifluoromethyl)-1H-imidazole;

5-(4-chlorophenyl)-4-[4-(methylsulfonyl)phenyl]-2-(trifluoromethyl)-1H-imidazole;

5-(2-chlorophenyl)-4-[4-(methylsulfonyl)phenyl]-2-(trifluoromethyl)-1H-imidazole;

5-(3,4-dichlorophenyl)-4-[4-(methylsulfonyl)phenyl]-2-(trifluoromethyl)-1H-imidazole;

4-[4-(methylsulfonyl)phenyl]-5-(2-naphthyl)-2-(trifluoromethyl)-1H-imidazole;

5-(4-methoxyphenyl)-4-[4-(methylsulfonyl)phenyl]-2-(trifluoromethyl)-1H-imidazole;

5-(4-methylphenyl)-4-[4-(methylsulfonyl)phenyl]-2-(trifluoromethyl)-1H-imidazole;

5-(2,4-difluorophenyl)-4-[4-(methylsulfonyl)phenyl]-2-(trifluoromethyl)-1H-imidazole;

5-(3,4-difluorophenyl)-4-[4-(methylsulfonyl)phenyl]-2-(trifluoromethyl)-1H-imidazole;

4-[4-(methylsulfonyl)phenyl]-5-phenyl-2-(trifluoromethyl)-1H-imidazole;

5-(4-fluorophenyl)-2-(3-furyl)-4-(4-methylsulfonylphenyl)-1H-imidazole;

4-[5-(4-fluorophenyl)-2-(trifluoromethyl)-1H-imidazol-4-yl]benzenesulfonamide;

4-[5-(4-fluorophenyl)-2-phenoxymethyl-1H-imidazol-4-yl]benzenesulfonamide;

4-[5-(4-fluorophenyl)-2-(2-phenyl-trans-eth-1-ene)-1H-imidazol-4-yl]benzenesulfonamide;

4-[5-(4-fluorophenyl)-2-(2-benzofuryl)-1H-imidazol-4-yl]benzenesulfonamide;

4-[5-(4-fluorophenyl)-2-isopropyl-1H-imidazol-4-yl]benzenesulfonamide;

4-[5-(4-fluorophenyl)-2-methyl-1H-imidazol-4-yl]benzenesulfonamide;

4-[5-(4-fluorophenyl)-2-(2-furyl)-1H-imidazol-4-yl]benzenesulfonamide;

4-[2-benzylthio-5-(4-fluorophenyl)-1H-imidazol-4-yl]benzenesulfonamide;

4-[5-(4-fluorophenyl)-2-hydroxymethyl-1H-imidazol-4-yl]benzenesulfonamide;

4-[5-(3-fluoro-4-methoxyphenyl)-2-(trifluoromethyl)-1H-imidazol-4-yl]benzenesulfonamide;

4-[5-(4-chlorophenyl)-2-(trifluoromethyl)-1H-imidazol-4-yl]benzenesulfonamide;

4-[5-(2-chlorophenyl)-2-(trifluoromethyl)-1H-imidazol-4-yl]benzenesulfonamide;

4-[5-(-3,4-dichlorophenyl)-2-(trifluoromethyl)-1H-imidazol-4-yl]benzenesulfonamide;

4-[5-(2-naphthyl)-2-(trifluoromethyl)-1H-imidazol-4-yl]benzenesulfonamide;

4-[5-(4-methoxyphenyl)-2-(trifluoromethyl)-1H-imidazol-4-yl]benzenesulfonamide;

4-[5-(4-methylphenyl)-2-(trifluoromethyl)-1H-imidazol-4-yl]benzenesulfonamide;

4-[5-(2,4-difluorophenyl)-2-(trifluoromethyl)-1H-imidazol-4-yl]benzenesulfonamide;

4-[5-(3,4-difluorophenyl)-2-(trifluoromethyl)-1H-imidazol-4-yl]benzenesulfonamide;

4-[5-phenyl-2-(trifluoromethyl)-1H-imidazol-4-yl]benzenesulfonamide;

4-[5-(4-fluorophenyl)-2-(3-furyl)-1H-imidazol-4-yl]benzenesulfonamide;

4-(3,4-dimethoxyphenyl)-5-[4-(methylsulfonyl)phenyl]-2-(trifluoromethyl)-1H-imidazole;

4-(4-methoxy-3-methylphenyl)-5-[4-(methylsulfonyl)phenyl]-2-(trifluoromethyl)-1H-imidazole;

5-(4-fluorophenyl)-1-methyl-4-[4-(methylsulfonyl)phenyl]-2-(trifluoromethyl)-1H-imidazole;

4-(4-fluorophenyl)-1-methyl-5-[4-(methylsulfonyl)phenyl]-2-(trifluoromethyl)-1H-imidazole;

5-(3,5-dimethylphenyl)-4-[4-(methylsulfonyl)phenyl]-2-(trifluoromethyl)-1H-imidazole;

5-(5-bromothien-2-yl)-4-[4-(methylsulfonyl)phenyl]-2-(trifluoromethyl)-1H-imidazole;

N,N-dimethyl-4-[4-[4-(methylsulfonyl)phenyl]-2-(trifluoromethyl)-1H-imidazol-5-yl]benzenamine;

4-(4-fluorophenyl)-5-[4-(methylsulfonyl)phenyl]-1H-imidazole-2-thiol;

2-[[[4-(4-fluorophenyl)-5-[4-(methylsulfonyl)phenyl]-1H-imidazol-2-yl]thio]methyl]quinoline;

4-(4-fluorophenyl)-5-[4-(methylsulfonyl)phenyl]-2-[(phenylmethyl) sulfonyl]-1H-imidazole;

5-(3,5-dimethyl-4-methoxyphenyl)-4-[4-(methylsulfonyl)phenyl]-2-(trifluoromethyl)-1H-imidazole;

5-[3-fluoro-4-(methylthio)phenyl]-4-[4-(methylsulfonyl)phenyl]-2-(trifluoromethyl)-1H-imidazole;

5-(3-chloro-5-methylphenyl)-4-[4-(methylsulfonyl)phenyl]-2-(trifluoromethyl)-1H-imidazole;

5-[3-chloro-4-(methylthio)phenyl]-4-[4-(methylsulfonyl)phenyl]-2-(trifluoromethyl)-1H-imidazole;

5-(3-fluoro-4-methylphenyl)-4-[4-(methylsulfonyl)phenyl]-2-(trifluoromethyl)-1H-imidazole;

1-[5-(3-chloro-5-methylphenyl)-4-[4-(methylsulfonyl)phenyl]-2-(trifluoromethyl)-1H-imidazol-1-yl]ethanone;

5-(3-methylphenyl)-4-(4-(methylsulfonyl)phenyl]-2-trifluoromethyl-1H-imidazole;

5-(3-methylphenyl)-4-[4-(sulfonamido)phenyl]-2-trifluoromethyl-1H-imidazole;

5-(3,4-dimethylphenyl)-4-[4-(methylthio)phenyl]-2-(trifluoromethyl)-1H-imidazole;

4-(4-(methylsulfonyl)phenyl]-5-(3-pyridyl)-2-(trifluoromethyl)-1H-imidazole;

5-(3-cyanophenyl)-4-[4-(methylthio)phenyl]-2-(trifluoromethyl)-1H-imidazole;

5-(2-fluorophenyl)-4-[4-(methylsulfonyl)phenyl]-2-(trifluoromethyl)-1H-imidazole;

5-(3-methoxyphenyl)-4-[4-(methylsulfonyl)phenyl]-2-(trifluoromethyl)-1H-imidazole;

5-(2-methylphenyl)-4-[4-(methylsulfonyl)phenyl]-2-(trifluoromethyl)-1H-imidazole;

5-(cyclohexyl)-4-[4-(methylsulfonyl)phenyl]-2-(trifluoromethyl)-1H-imidazole;

4-[4-(methylsulfonyl)phenyl]-5-(2-thiophenyl)-2-(trifluoromethyl)-1H-imidazole;

5-(4-chloro-3-methylphenyl)-4-[4-(methylsulfonyl)phenyl]-2-(trifluoromethyl)-1H-imidazole;

5-(4-cycloheptyl)-4-[4-(methylsulfonyl)phenyl]-2-(trifluoromethyl)-1H-imidazole;

5-(4-fluoro-3-methylphenyl)-4-[4-(methylsulfonyl)phenyl]-2-(trifluoromethyl)-1H-imidazole;

5-(cyclopentyl)-4-[4-(methylsulfonyl)phenyl]-2-(trifluoromethyl)-1H-imidazole;

4-[4-(methylsulfonyl)phenyl]-5-(3-thiophenyl)-2-(trifluoromethyl)-1H-imidazole;

5-(3-fluoro-2-methylphenyl)-4-[4-(methylsulfonyl)phenyl]-2-(trifluoromethyl)-1H-imidazole;

5-(4-chloro-3-methoxyphenyl)-4-[4-(methylsulfonyl)phenyl]-2-(trifluoromethyl)-1H-imidazole;

5-(4-fluorophenyl)-2-(methoxymethyl)-4-[4-(methylsulfonyl)-phenyl]-1H-imidazole;

4-(4-fluorophenyl)-5-[4-(methylsulfonyl)phenyl]-2-[(2-propenyloxy)methyl]-1H-imidazole;

2-(ethoxymethyl)-4-(4-fluorophenyl)-5-[4-(methylsulfonyl)phenyl]-1H-imidazole;

4-(4-fluorophenyl)-5-[4-(methylsulfonyl)phenyl]-2-(phenyl-methoxymethyl)-1H-imidazole;

1-[4-(4-fluorophenyl)-5-[4-(methylsulfonyl)phenyl]-1H-imidazol-2-yl]ethanone;

2-(2-bromophenyl)-1-[4-(4-fluorophenyl)-5-[4-(methylsulfonyl)phenyl]-1H-imidazol-2-yl]ethanone;

1-(4-(4-fluorophenyl)-5-[4-methylsulfonyl)phenyl]-1H-imidazol-2-yl]-3-phenyl-1-propanone;

1-[5-(4-fluorophenyl)-4-[4-(methylsulfonyl)phenyl]-1H-imidazol-2-yl]-2-phenylethanone;

[5-(4-fluorophenyl)-4-[4-(methylsulfonyl)phenyl]-1H-imidazol-2-yl]phenylmethanone;

1-[5-(4-fluorophenyl)-4-[4-(methylsulfonyl)phenyl]-1H-imidazol-2-yl]-4-phenyl-1-butanone;

2,2,2-trifluoro-1-[4-(4-fluorophenyl)-5-[4-methylsulfonyl)phenyl]-1H-imidazol-2-yl]ethanone;

4-(4-fluorophenyl)-5-[4-(methylsulfonyl)phenyl]-2-(phenyl-sulfonyl)-1H-imidazole;

4-(4-fluorophenyl)-α-methyl-5-[4-(methylsulfonyl)phenyl]-1H-imidazole-2-methanol;

4-(4-fluorophenyl)-2-(1-methoxyethyl)-5-[4-(methylsulfonyl)phenyl]-1H-imidazole; and 2-(1,1-difluoroethyl)-4-(4-fluorophenyl)-5-[4-(methylsulfonyl)phenyl]-1H-imidazole.

Within Formula I there is a subclass of compounds of high interest represented by Formula II:

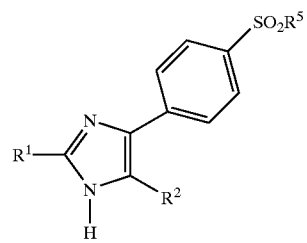

wherein $R^1$ is selected from lower alkyl, lower haloalkyl, lower aralkyl, lower heterocyclicalkyl, lower heteroaralkyl, acyl, cyano, mercapto, lower alkoxy, lower alkylthio, lower alkylthioalkyl, lower alkylsulfonyl, lower haloalkylsulfonyl, lower arylsulfonyl, halo, lower hydroxyalkyl, lower alkoxyalkyl, lower alkenyloxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower haloalkylcarbonyl, carboxyl, aminocarbonyl, lower alkylaminocarbonyl, lower alkylaminocarbonylalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, lower hydroxyl, lower alkoxy, lower hydroxyalkyl and lower haloalkoxy; wherein $R^2$ is selected from heteroaryl, lower cycloalkyl, lower cycloalkenyl, and aryl, wherein the heteroaryl, lower cycloalkyl, lower cycloalkenyl, and aryl radicals are substituted with one or more radicals selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and wherein $R^5$ is selected from lower alkyl and amino; provided $R^1$ is not lower alkyl when $R^5$ is methyl and when $R^2$ is phenyl or phenyl substituted with methyl, methoxy or chloro; or a pharmaceutically-acceptable salt thereof.

A preferred class of compounds consists of those compounds of Formula II wherein $R^1$ is selected from lower heterocyclicalkyl, lower heteroaralkyl, acyl, cyano, mercapto, lower alkoxy, lower alkylthio, lower alkylthioalkyl, lower alkylsulfonyl, lower haloalkylsulfonyl, lower arylsulfonyl, halo, lower alkenyloxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower alkoxycarbonyl, lower haloalkylcarbonyl, aminocarbonyl, lower alkylaminocarbonyl, lower alkylaminocarbonylalkyl, lower aralkoxy, lower aralkylthio, phenylsulfonyl, lower aralkylsulfonyl, lower heteroaralkoxy, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are optionally substituted at a substitutable position with one or more radicals selected from halo, lower alkylthio, lower alkylsulfinyl lower alkyl, cyano, lower haloalkyl, lower hydroxyl, lower alkoxy, lower hydroxyalkyl and lower haloalkoxy; wherein $R^2$ is selected from heteroaryl, lower cycloalkyl, lower cycloalkenyl, and aryl, wherein the heteroaryl, lower cycloalkyl, lower cycloalkenyl, and aryl radicals are substituted with one or more radicals selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and wherein $R^5$ is selected from lower alkyl and amino; or a pharmaceutically-acceptable salt thereof.

Another preferred class of compounds consists of those compounds of Formula II wherein $R^1$ is selected from lower alkyl, lower haloalkyl, lower hydroxyalkyl, lower alkoxyalkyl, lower aralkylsulfonyl, lower arylthioalkyl, heteroarylalkoxyalkyl, lower heteroaryloxyalkyl, lower heteroarylthioalkyl, lower heteroarylalkylthioalkyl, lower aralkylthio, and lower aralkoxy; wherein $R^2$ is selected from heteroaryl, cycloalkyl and aryl, wherein the heteroaryl, cycloalkyl and aryl radicals are substituted at a substitutable position with one or more radicals selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, phenylamino and nitro; and wherein $R^5$ is selected from lower alkyl-and amino; or a pharmaceutically-acceptable salt thereof.

Within Formula I there is a subclass of compounds of high interest represented by Formula III:

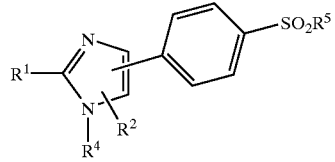

wherein $R^1$ is selected from lower alkyl, lower haloalkyl, lower aralkyl, lower heterocyclicalkyl, lower heteroaralkyl, acyl, cyano, mercapto, lower alkoxy, lower alkylthio, lower alkylthioalkyl, lower alkylsulfonyl, lower haloalkylsulfonyl, lower arylsulfonyl, halo, lower hydroxyalkyl, lower alkoxyalkyl, lower alkenyloxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower haloalkylcarbonyl, carboxyl, aminocarbonyl, lower alkylaminocarbonyl, lower alkylaminocarbonylalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, lower hydroxyl, lower alkoxy, lower: hydroxyalkyl and lower haloalkoxy; wherein $R^2$ is selected from heteroaryl, lower cycloalkyl, lower cycloalkenyl, and aryl, wherein the heteroaryl, lower cycloalkyl, lower cycloalkenyl, and aryl radicals are substituted with one or more radicals selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; wherein $R^4$ is selected from lower alkyl and acyl; and wherein $R^5$ is selected from lower alkyl and amino; or a pharmaceutically-acceptable salt thereof.

Compounds of Formula I where $R^2$ is heteroaryl would also be capable of inhibiting cytokines, such as TNF, IL-1, IL-6, and IL-8. As such, the compounds can be used in the manufacture of a medicament or in a method for the treatment for the prophylactic or therapeutic treatment of diseases mediated by cytokines, such as TNF, IL-1, IL-6, and IL-8.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one-or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl methoxybutyl and methoxypropyl. The "alkoxy" or "alkoxyalkyl" radicals may be further substituted with one or more halo atoms, such as fluoro, chloro or bromo, to provide "haloalkoxy" or "haloalkoxyalkyl" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cyanoalkyl" embraces radicals having a cyano or nitrile (—CN) radical attached to an alkyl radicals as described above. More preferred cyanoalkyl radicals are "lower cyanoalkyl"radicals having one to six carbon atoms. Examples of such lower cyanoalkyl radicals include cyanomethyl, cyanopropyl, cyanoethyl and cyanobutyl. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces unsaturated cyclic radicals having three to ten carbon atoms. More preferred cycloalkenyl radicals are "lower cycloalkenyl" radicals having about five to about eight carbon atoms. Examples of such radicals include cyclobutenyl, cyclopentenyl, cyclohexenyl and cycloheptenyl. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The terms "heterocyclic" and "heterocyclo" embrace saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated. condensed heterocyclic group containing 1 to 2 oxygen atoms and. 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like. Said "heterocyclic" radicals may have 1 to 3 substituents such as lower alkyl, hydroxy, oxo, amino and lower alkylamino. More preferred heteroaryl radicals include five to six membered heteroaryl radicals. The term "heterocyclicalkyl" embraces heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "arylthio" embraces radicals containing an aryl radical, attached to a divalent sulfur atom, such as a phenylthio radical. The term "arylthioalkyl" embraces arylthio radicals attached to an alkyl radical. More preferred arylthioalkyl radicals are "lower arylthioalkyl" radicals having alkyl radicals of one to six carbon atoms and an arylthio radical as described above. Examples of such radicals include phenylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl. The term "arylsulfonyl" embraces aryl radicals as defined above, attached to a sulfonyl radical. Examples of such radicals include phenylsulfonyl. The term "aralkylsulfonyl" embraces aralkyl radicals as defined above, attached to a sulfonyl radical. Examples of such radicals include benzylsulfonyl. The term "heteroarylsulfonyl" embraces heteroaryl radicals as defined above, attached to a sulfonyl radical. Examples of such radicals include thienylsulfonyl, oxazolylsulfonyl and pyridylsulfonyl. The term "heteroarylalkylsulfonyl" embraces heteroarylalkyl radicals as defined above, attached to a sulfonyl radical. Examples of such radicals include thienylmethylsulfonyl. The terms "sulfamyl", "minosulfonyl" and "sulfonamidyl" denotes NH$_2$O$_2$S—. The term "acyl" denotes a radical provided by the residue after removal of hydroxyl from an organic acid. Examples of such acyl radicals include formyl, alkanoyl and aroyl radicals. The terms "carboxy" or "carboxyl", whether used alone or with other terms, such as "carboxyalkyl", denotes —CO$_2$H. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, haloalkyl and haloalkoxy. The terms benzyl and phenylmethyl are interchangeable. The term "aralkenyl" embraces aryl-substituted alkenyl radicals. Preferable aralkenyl radicals are "lower aralkenyl" radicals having aryl radicals attached to alkenyl radicals having two to six carbon atoms. Examples of such radicals include phenylethenyl and diphenylethenyl. The aryl in said aralkenyl may be additionally substituted with halo, alkyl, alkoxy, haloalkyl and haloalkoxy. The terms "alkylcarbonyl", "arylcarbonyl" and "aralkylcarbonyl" include radicals having alkyl, aryl and aralkyl radicals, respectively, as defined above, attached via an oxygen atom to a carbonyl radical. More preferred alkylcarbonyl radicals are "lower alkylcarbonyl" radicals having one to six carbon atoms. Examples of such radicals include methylcarbonyl and ethylcarbonyl. More preferred aralkylcarbonyl radicals are "lower aralkylcarbonyl" radicals having aryl radicals attached to alkyl radicals having one to six carbon atoms. Examples of such aralkylcarbonyl radicals include benzylcarbonyl. An example of an arylcarbonyl radical is phenylcarbonyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical. The term "carboxyalkyl" embrace radicals having a carboxy radical as defined above, attached to an alkyl radical. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "heteroaralkyl" embraces heteroaryl-substituted alkyl radicals. More preferred heteroaralkyl radicals are "lower heteroaralkyl" radicals having five to six membered heteroaryl radicals attached to one to six carbon atoms. Examples of such radicals include pyridylmethyl, quinolylmethyl, thienylmethyl, furylethyl and quinolylethyl. The heteroaryl in said heteroaralkyl may be additionally substituted with halo, alkyl, alkoxy, haloalkyl and haloalkoxy. The term "aryloxy" embraces aryl radicals, as defined above, attached to an oxygen atom. The aryl in said aryloxy may be additionally substituted with one or more halo, alkyl, alkoxy, haloalkyl and haloalkoxy radicals. Examples of such radicals include phenoxy. The term "heteroaryloxy" embraces heteroaryl radicals as defined above attached to an oxygen radical. More preferred heteroaryloxy radicals are "lower heteroaryloxy" radicals having five to six membered heteroaryl radicals. The term "aralkoxy" embraces oxy-containing aralkyl radicals attached through an oxygen atom to other radicals. The term "aralkoxyalkyl" embraces alkyl radicals having one or more aralkoxy radicals attached to the Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of alkyl radical, that is, to form monoaralkyloxyalkyl and diaralkyloxyalkyl radicals. The "aralkoxy" or "aralkoxyalkyl" radicals may be further substituted on the aryl ring portion of the radical. More preferred aralkoxyalkyl radicals are "lower aralkoxyalkyl" having an alkoxy attached to one to six carbon atoms. Examples of lower aralkoxyalkyl radicals include benzyloxymethyl. The term "heteroarylthio" embraces radicals having heteroaryl radicals attached to a sulfur radical. More preferred heteroarylthio radicals are "lower heteroarylthio" radicals having five to six membered heteroaryl radicals. Examples of such radicals include 2-furylthio, 2-thienylthio, 3-thienylthio, 4-pyridylthio and 3-pyridylthio. The term "alkoxyaralkoxyalkyl" embraces alkoxy substituted aralkoxyalkyl radicals. More preferred radicals have lower alkoxy substituted aralkoxyalkyl, where lower alkoxy is defined above. The terms "heteroaralkylthio" and "heteroaralkylthio" denote radicals having an heteroaryl radical attached to an alkylthio radical. More preferred heteroaralkylthio radicals are "lower heteroaralkylthio" radicals having heteroaryl radicals attached to lower alkylthio radicals as described above. Examples of such radicals include furylmethylthiomethyl and quinolylmethylthioethyl. The term "heteroarylalkylthioalkyl" denotes radicals having an heteroaryl radical attached to an alkylthio radical further attached through the sulfur atom to an alkyl radical. More preferred heteroarylalkylthioalkyl are "lower heteroarylalkylthioalkyl" radicals having lower heteroarylalkyl radicals as described above. Examples of such radicals include furylmethylthiomethyl and quinolylmethylthioethyl. The term "heteroarylthioalkyl" denotes radicals having an heteroaryl radical attached to a sulfur atom further attached through the sulfur atom to an alkyl radical. More preferred heteroarylthioalkyl radicals are "lower heteroarylthioalkyl" having lower heteroarylthio radicals as described above. Examples of such radicals include thienylthiomethyl and pyridylthiohexyl. The term "aralkylthio" embraces radicals having aralkyl radicals attached to a bridging sulfur atom. More preferred aralkylthio radicals are "lower aralkylthio" radicals having the aryl radicals attached to one to six carbon atoms. Examples of such radicals include benzylthio and phenylethylthio. The term "aralkylthioalkyl" embraces radicals having aralkyl radicals attached to alkyl radicals through a bridging sulfur atom. More preferred aralkylthioalkyl radicals are "lower aralkylthioalkyl" radicals having the aralkylthio radicals attached to one to six carbon atoms. Examples of such radicals include benzylthiomethyl and phenylethylthiomethyl. The term "heteroaryloxyalkyl" denotes radicals having an heteroaryl radical attached to an oxygen atom further attached through the oxygen atom to an alkyl radical. More preferred heteroaryloxyalkyl radicals are "lower heteroaryloxyalkyl" radicals having five to six membered heteroaryl radicals. Examples of such radicals include furylbutoxyethyl, pyridyloxymethyl and thienyloxyhexyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. More preferred alkylamino radicals are "lower alkylamino" radicals having one or two alkyl radicals of one to six carbon atoms, attached to a nitrogen atom. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above; attached to a carbonyl radical. Examples of such radicals include N-methylaminocarbonyl and N,N-dimethylcarbonyl. The term "arylamino" denotes amino groups which have been substituted with one or two aryl radicals, such as N-phenylamino. The "arylamino" radicals may be further substituted on the aryl ring portion of the radical. The terms "N-arylaminoalkyl" and "N-aryl-N-alkylaminoalkyl" denote amino groups which have been substituted with one aryl radical or one aryl and one alkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The term "aminocarbonyl" denotes an amide group of the formula —C(=O)NH$_2$. The term "alkylaminocarbonylalkyl" denotes an aminocarbonyl group which has been substituted with one or two alkyl radicals. More preferred are "lower alkylaminocarbonylalkyl" having lower alkylaminocarbonyl radicals as described above attached to one to six carbon atoms. The term "aryloxyalkyl" embraces alkyl radicals having one or more aryloxy radicals, aryl radicals attached to a divalent oxygen atom, attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl. The terms "heteroaralkoxyalkyl" and "heteroarylalkoxyalkyl" embrace alkyl radicals having one or more heterocyclic radicals attached to an alkoxy radical, further attached to the alkyl radical. More preferred heteroaralkoxyalkyl radicals are "lower heteroaryl alkoxyalkyl radicals having five to six membered heteroaryl radicals. Examples of such radicals include 2-thienylmethoxymethyl.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having or susceptible to such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, pantothenic, toluenesulfonic, 2-hydroxyethanesulfonic sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, -potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–VII, wherein the $R^1$–$R^5$ substituents are as defined for Formula I–III, above, except where further noted.

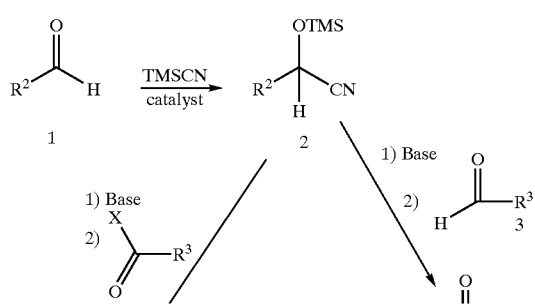

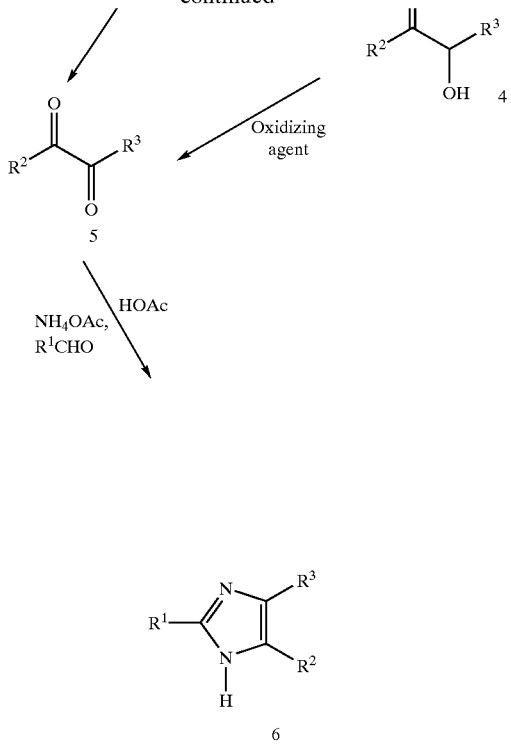

The subject imidazole compounds 6 of this invention may be synthesized according to the sequence outlined in Scheme I. Aldehyde 1 may be converted to the protected cyanohydrin 2 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 2 with a strong base followed by treatment with aldehyde 3 and using both acid and base treatments, in that order, on workup gives enol 4. Examples of strong bases suitable for this reaction are lithium diisopropylamide (LDA) and lithium hexamethyldisilazane. Enol 4 may be converted to diketone 5 by reaction with a suitable oxidizing agent, such as bismuth oxide or manganese dioxide, or by a Swern oxidation using dimethyl sulfoxide (DMSO) and trifluoroacetic anhydride. Diketone 5 may be obtained directly by reaction of the anion of cyanohydrin 2 with a substituted acid halide (where X is halo). Any of compounds 4 and 5 may be used as intermediates for conversion to imidazoles 6 according to chemical procedures known by those skilled in the art and described by M. R. Grimmett, "Advances in Imidazole Chemistry" in Advances in Heterocyclic Chemistry, 12, 104 (1970). The conversion of 5 to imidazoles 6 is carried out by reaction with ammonium acetate and an appropriate aldehyde ($R^1$CHO) in acetic acid. Enol 4 may be converted to imidazoles 6 by reaction with formamide. In addition, enol 4 may be converted to imidazoles by first acylating with an appropriate acyl group ($R^1$CO—) and then treating with ammonium hydroxide.

Scheme II

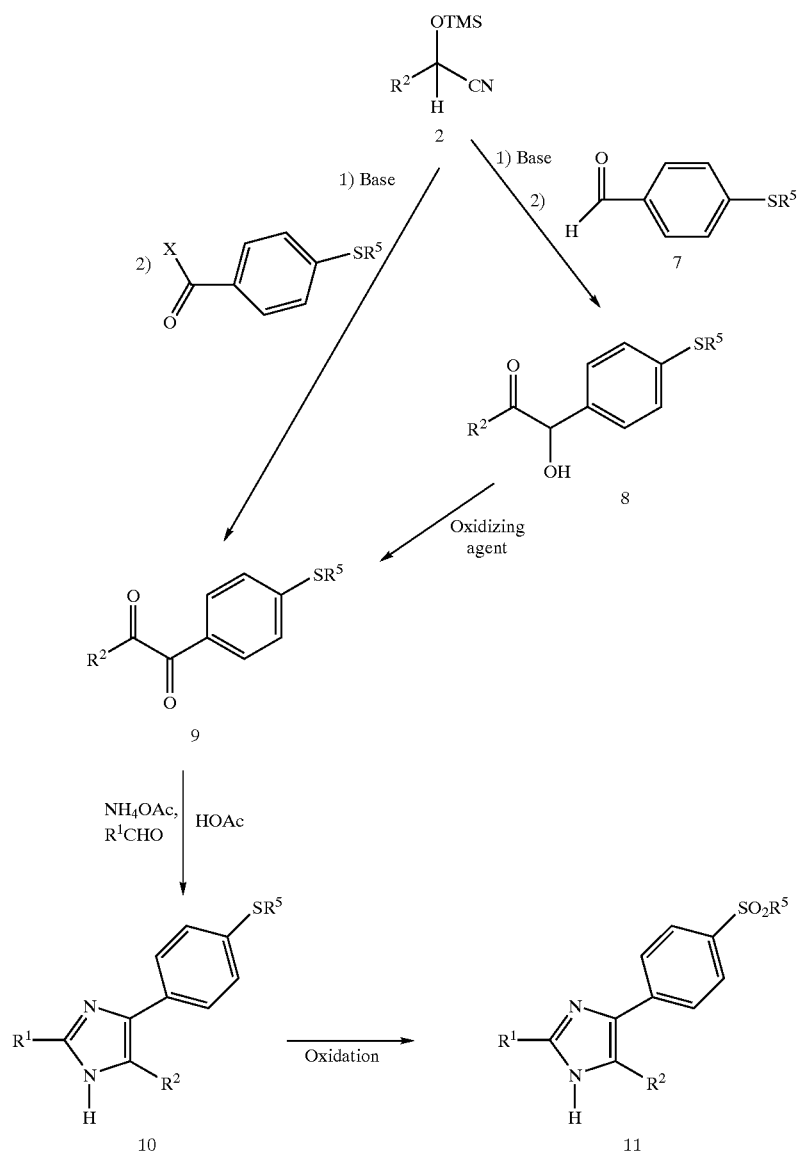

The subject imidazole compounds 11 of this invention may be synthesized according to the sequence outlined in Scheme II. Reaction of cyanohydrin 2 with a strong base followed by treatment with benzaldehyde 7 (where $R^5$ is alkyl) and using both acid and base treatments, in that order, on workup gives benzoin 8. Examples of strong bases suitable for this reaction are lithium diisopropylamide (LDA) and lithium hexamethyldisilazane. Benzoin 8 may be converted to benzil 9 by reaction with a suitable oxidizing agent, such as bismuth oxide or manganese dioxide, or by a Swern oxidation using dimethyl sulfoxide (DMSO) and trifluoroacetic anhydride. Benzil 9 may be obtained directly by reaction of the anion of cyanohydrin 2 with a substituted benzoic acid halide (where X is halo) Any of compounds 8 and 9 may be used as intermediates for conversion to imidazoles 10 (where $R^5$ is alkyl) according to chemical procedures known by those skilled in the art and described by M. R. Grimmett, "Advances in Imidazole Chemistry" in Advances in Heterocyclic Chemistry, 12, 104 (1970). The conversion of 9 to imidazoles 10 is carried out by reaction with ammonium acetate and an appropriate aldehyde ($R^1$CHO) in acetic acid. Benzoin 8 may be converted to imidazoles 10 by reaction with formamide. In addition, benzoin 8 may be converted to imidazoles by first acylating with an appropriate acyl group ($R^1$CO—) and then treating with ammonium hydroxide. Those skilled in the art will recognize that the oxidation of the sulfide (where $R^5$ is methyl) to the methylsulfone (—$SO_2CH_3$) may be carried out at any point along the way beginning with compounds 8, and including oxidation of imidazoles 10, using, for examples, reagents such as hydrogen peroxide in acetic acid, m-chloroperoxybenzoic acid (MCPBA) and potassium peroxymonosulfate (OXONE®).

Scheme III

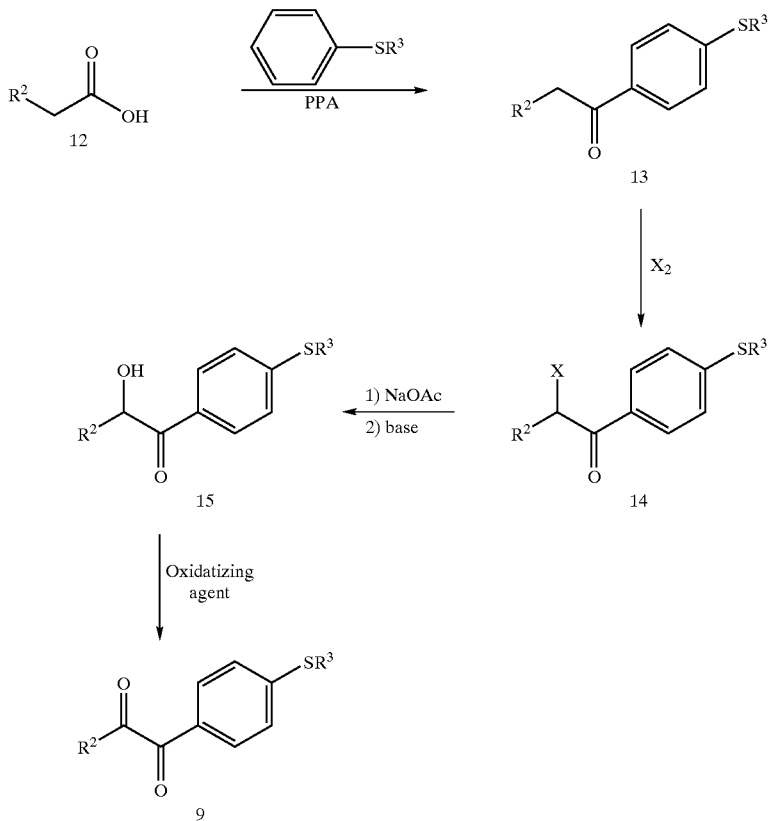

Alternative syntheses of benzoins and benzils may be carried out as described in Scheme III. Acylation of a thiobenzene derivative with an appropriately substituted acetic acid 12 using an acidic catalyst yields desoxybenzoin 13. Some suitable acidic catalysts include polyphosphoric acid (PPA), sulfuric acid, titanium tetrachloride, ferric chloride and stannic chloride. The resulting desoxybenzoin 13 may be halogenated to give haloketone 14 (where X is halo). Treatment of compound 14 with either water in a suitable co-solvent such as acetone, or with a. carboxylate salt, followed by saponification with base, yields benzoin 15. Examples of bases suitable for saponification include sodium bicarbonate, sodium carbonate, potassium carbonate, sodium hydroxide and ammonium hydroxide. Examples of appropriate carboxylate salts include sodium acetate and sodium benzoate. Compound 15 is converted to benzil 9 by reaction with a suitable oxidizing agent such as bismuth oxide or manganese dioxide. Alternatively, benzil 9 may be synthesized directly from desoxybenzoin 13 by treatment with an appropriate oxidizing agent, such as selenious acid ($H_2SeO_3$).

Haloketone 14 may be converted to imidazoles 10 by reaction either with formamide or with amidines.

Scheme IV

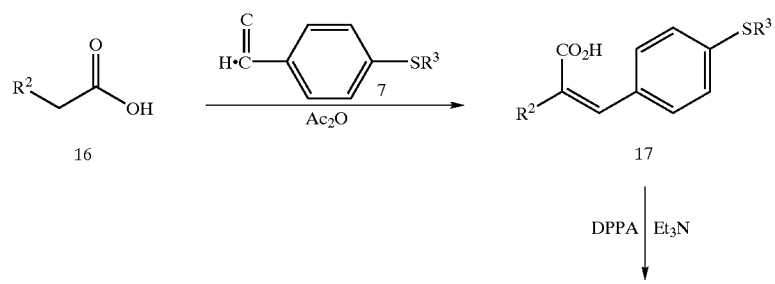

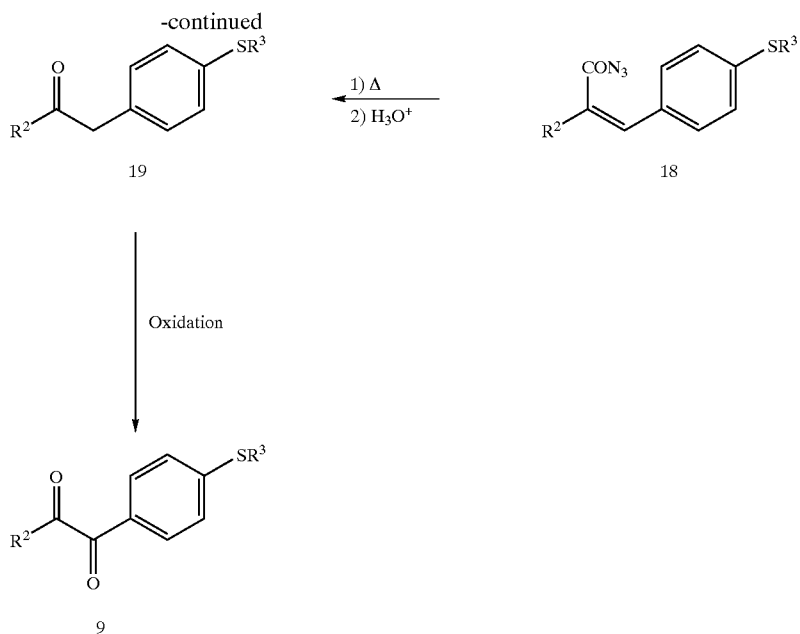

Scheme III outlines yet another outlines yet another method for the synthesis of benzil 9. Reaction of a suitable acetic acid derivative 16 with an aromatic aldehyde 7 in acetic anhydride yields unsaturated acid 17. Acid 17 is converted to acyl azides 18 by reaction with diphenylphosphoryl azide (DPPA) in the presence of a base such as triethylamine ($Et_3N$) or by reaction of an activated carboxyl derivative of 17, such as an acid chloride or anhydride, with sodium azide. Decomposition of the acyl azide 18 by thermolysis, followed by hydrolysis with aqueous acid yields desoxybenzoin 19. Compound 19 may be converted to benzil 9 by oxidation according to procedures discussed in Schemes II–III.

Scheme V

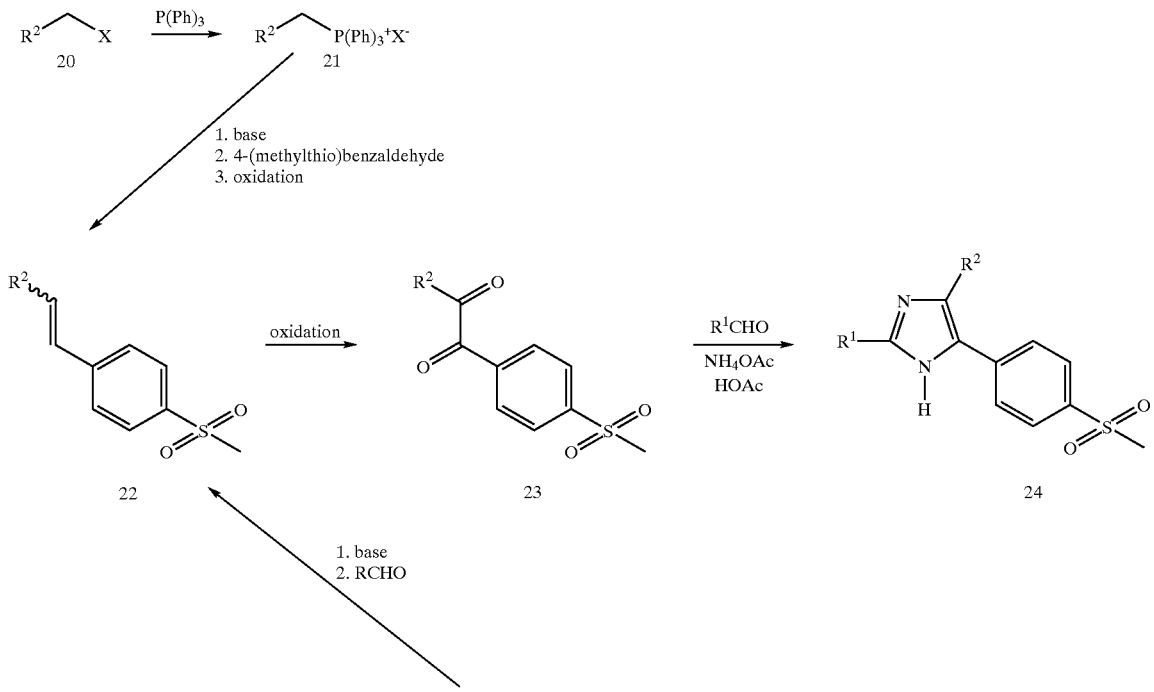

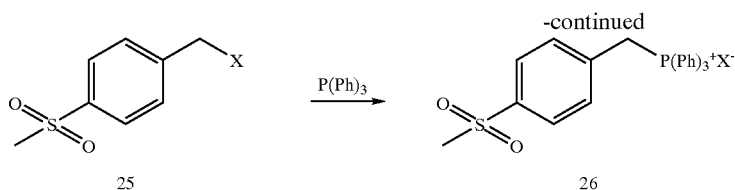

The compounds of the invention can be prepared according to the procedures in Scheme V. The subject imidazoles 24 are obtained from the condensation of diketones 23 with aldehydes $R^1CHO$ in the presence of acetic acid and ammonium acetate, as previously described. Scheme V differs from previous synthetic routes in that it employs an α-diketone 23 that is obtained by oxidation of the olefinic intermediate 22. This transformation is conveniently accomplished in one pot subjecting the olefin to potassium permanganate oxidation in acetic anhydride, according to a method of stilbene oxidation developed by Sharpless, et al. [*J. Am. Chem. Soc.*, 93, 3303 (1971)]. One may reduce the requirement for acetic anhydride by using a cosolvent, such as dioxane, ether, or methylene chloride. Oxidative sequences involving catalytic permanganate; catalytic osmium tetroxide followed by Swern oxidation; or epoxidation followed by oxidative rearrangement present alternatives to the conditions described.

Olefin 22 may be obtained using Wittig technology or other coupling protocols, such as transition metal mediated cross-coupling, silicon-based (Peterson) olefination, or sulfone-based (Julia) coupling. The commercial intermediate 25 (X=Cl) in the present scheme is transformed into an activated phosphorus compound, for example, a triphenylphosphonium salt. The phosphorus species 26 is deprotonated with a strong base, lithium ethoxide, generated in situ from n-butyllithium and ethanol. Other bases, such as sodium hydroxide or potassium t-butoxide present alternatives. A primarily aprotic medium could be employed, such as potassium tert-butoxide in tetrahydrofuran or sodium amide in dioxane. $R^2CHO$ represents an aryl aldehyde, such as benzaldehyde; an alkyl or cycloalkyl aldehyde, such as cyclohexanecarboxaldehyde; or a heterocyclic aldehyde, such as thiophene carboxaldehyde. It is recognized that the intermediate methyl sulfone 25 could be replaced with a different (e.g. ethyl sulfone) or sulphonamide with similar results.

Olefin 22 may also be obtained by allowing a suitable phosphonium salt 21 (X=Cl, Br, OTs, or I) to react in the presence of strong base, such as lithium ethoxide with 4-(thiomethyl)benzaldehyde. Oxidation of the sulfur atom to the sulfone is conveniently accomplished with Oxone® at this stage, but could be accomplished with other reagents, such as hydrogen peroxide or m-chloroperbenzoic acid, or could be effected at another place in the sequence. The oxidation step could be entirely eliminated by employing 4-(methylsulphonyl)benzaldehyde in the place of 4-(thiomethyl)benzaldehyde.

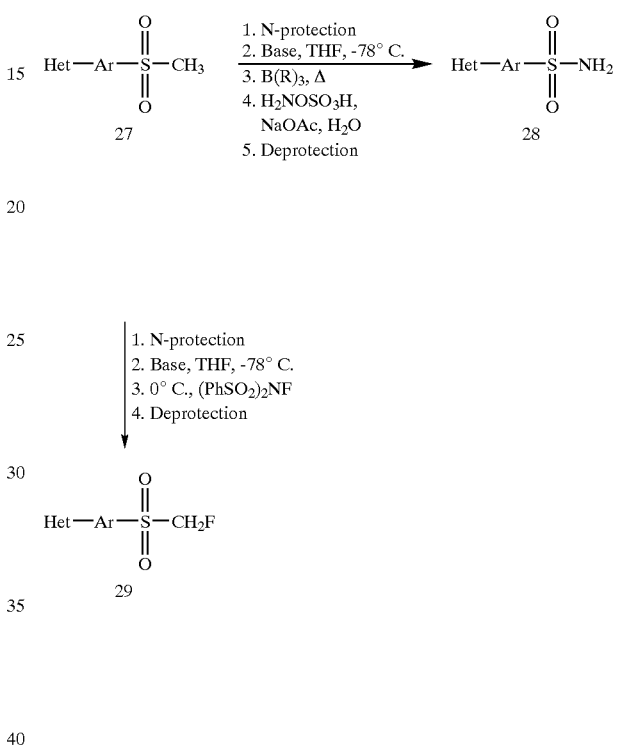

Synthetic Scheme VI shows the three step procedure used to prepare sulfonamide antiinflammatory agents 28 and the two step procedure used to prepare fluoromethyl sulfone antiinflammatory agents 29 from their corresponding methyl sulfones 27. In step one, THF solutions of the methyl sulfones 27 at −78° C. are treated with an alkyllithium reagent, e.g., methyllithium, n-butyllithium, lithium diisopropylamide (LDA), etc. In step two, the anions generated in step one are treated with an organoborane, e.g., triethylborane, tributylborane, etc., at −78° C. then allowed to warm to ambient temperature prior to stirring at reflux. An alternative to the boron chemistry involves room temperature alkylation, such as with trimethylsilylmethylhalides, followed by treatment with tetrabutylammonium fluoride (1M in THF). In step three, an aqueous solution of sodium acetate and hydroxylamine-O-sulfonic acid is added to provide the corresponding sulfonamide antiinflammatory agents 28 of this invention. Alternatively, the anion solutions generated in step one may be warmed to 0° C. and treated with N-fluorodibenzenesulfonamide to provide the corresponding fluoromethyl sulfone antiinflammatory agents 29 of this invention.

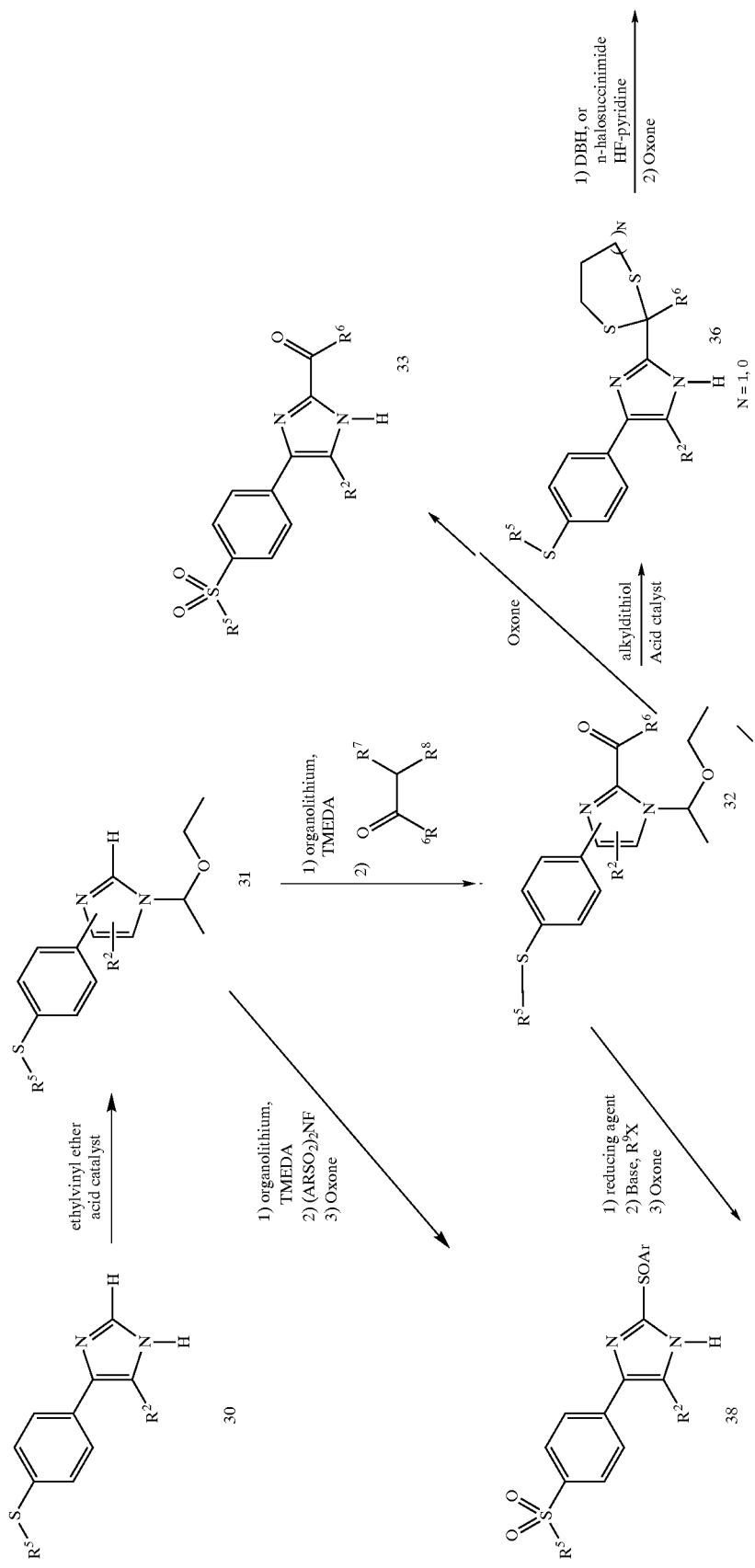

-continued
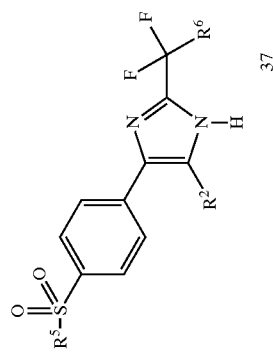
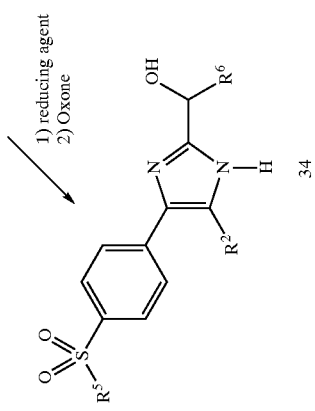
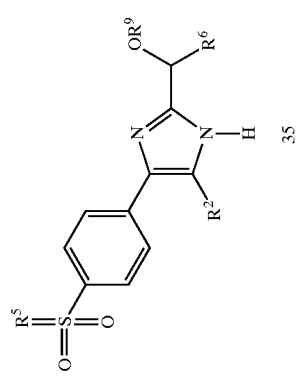

Synthetic Scheme VII outlines further modications at position 2 of the imidazole compounds of this invention. Compound 30 may be obtained via the condensation of benzoin 8 with formamide as discussed above. The parent imidazole 30, maybe converted to the ethoxyethyl derivatives 31 by treatment with ethylvinylether in the presence of an acid catalyst. Examples of suitable acid catalysts are dichloroacetic acid, p-toluenesulfonic acid, methanesulfonic acid and hydrogen chloride. Alternatively the ethoxyethyl group may be incorporated by chemical procedures known to those skilled in the art and described by T. S. Manoharan and R. S. Brown in *J. Org. Chem.*, 53, 1107–1110 (1988). Due to the tautomeric nature of the nitrogen atom, two compounds 31 are obtained at the end of this process. Both compounds 31 are carried on to subsequent steps as a mixture because this group is ultimately removed and upon removal one compound is obtained from the reaction sequence of interest. A series of acyl derivatives can be obtained by conversion of 31 into 32 and then 33 by lithiation via the process of Manoharan and Brown, followed by treatment of the resulting lithium anion with amides such as dimethylformamide ($R^6$=H, $R^7$ and $R^8$=$CH_3$), dimethyl acetamide($R^6$,$R^7$, $R^8$=$CH_3$) or with amides where $R^7$ and $R^8$=OMe and $CH_3$ and wherein $R^6$ may include hydrogen, lower alkyl, aryl, aralkyl, and haloalkyl. Subsequent treatment with Oxone® results in compounds 33, where $R^6$ is as defined above. The preparation of these amides involves the treatment of the appropriate carboxylic acid with N,O-dimethylhydroxyamine chloride in the presence of triethylamine, and 2-chloromethylpyridinium iodide at room temperature in methylene chloride. The preparation of the amide where $R^7$ and $R^8$ are OMe and methyl, and $R^6$ is $CF_3$ can be accomplished by those skilled in art by following the published procedure in *J. Org. Chem,.* 56, 4260 (1991). Finally, the lithium anion may be treated with other electrophiles, for example, trifluoroacetone or N-fluorodibenzenesulfonamide resulting in compounds where imidazole position 2 is [$CH_3(OH)CF_3$] or phenylsulfonyl 38, respectively. If further modification of the acyl group in compounds 32 is desired, the imidazole nitrogen at position 1 is left protected. This process is exemplified by the conversion of compounds 32 into 34, 35, 36, 37 and 38 where $R^6$ is defined as stated above. The conversion of 32 into 34 can be performed by treatment of compound 32 with a reducing agent followed by treatment with Oxone®. Some examples of reducing agents are sodium borohydride, lithium borohydride, zinc borohydride, lithium triethylborohydride, RED-AL, borane, alane, and diisopropylaluminum hydride. To synthesize ether compounds 35 ($R^9$ is lower alkyl, alkenyl or aralkyl), ketones 32 are reduced to the corresponding alcohols using a suitable reducing agent as defined above. The resulting alcohol is treated with a strong base, such as sodium hydride or lithium hydride in a suitable solvent, such as dimethylformamide, dimethylsulfoxide or tetrahydrofuran, and then reacted with the appropriate alkyl, aralkyl or alkenyl halide. Oxidation of the sulfide to the methyl sulfone results in concomitant loss of the nitrogen protecting group to produce compounds 35. The conversion of compound 32 to 37 may be carried out by those that are skilled in the art using procedures described by Susan C. Sondej and John A. Katzenellenbogen [*J. Org Chem.*, 51, 3508–3513 (1986).

The following examples contain detailed descriptions of the methods of preparation of compounds of Formula I–III. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

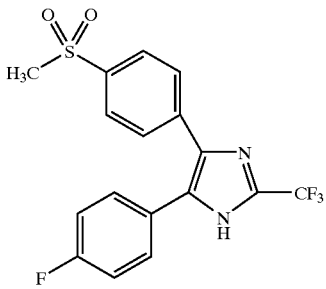

5-(4-Fluorophenyl)-4-(4-methylsulfonylphenyl)-2-trifluoromethyl-1H-imidazole

Method A

Step 1 Preparation of 4-Fluorophenyl-4'-methylthiophenyl-α-carboxystilbene (cis and trans)

4-Fluorophenylphenylacetic acid (23.5 g, 0.152 mol), p-methylthiobenzaldehyde (23.2 g, 0.152 mol), and triethylamine ($Et_3N$) (16.2 g, 0.16 mol) were dissolved in acetic anhydride (100 ml) and heated to reflux for 8 hours. After cooling, the contents were poured into water (500 ml) and stirred for 2 hours. The mixture was extracted with methylene chloride, dried ($MgSO_4$) and concentrated in vacuo. The residue was dissolved in methanol (300 ml), 2N KOH (potassium hydroxide) (100 ml) was added, and the contents were placed on a steam bath for 30 minutes. The mixture was cooled in ice and conc. HCl was added to reach pH 3, forming a precipitate. The precipitate was filtered, air dried and recrystallized from ethanol (EtOH) to give 24 g (50%) of 4-fluorophenyl-4'-methylthiophenyl-α-carboxystilbene (cis and trans) in the first crop: Anal. Calc'd. for $C_{16}H_{13}FO_2S$ (M.W.=288.34): C, 66.65; H, 4.54. Found: C, 66.71; H, 4.49.

Step 2 Preparation of 1-(4-Fluorophenyl)-2-(4-methylthiophenyl)-1-ethanone

A solution of the stilbene carboxylic acid (11.8 g, 41 mmol) from step 1, diphenylphosphoryl azide ($(PhO)_2PON_3$) (12.5 g, 1.1 equiv.) and $Et_3N$ (5 g, 1.2 equiv.) in toluene (200 ml) was stirred for 1 hour at 25° C. The contents were poured into water (1 L), the layers separated and the organic layer was washed with brine. After filtration through $MgSO_4$, the toluene solution was heated at reflux for 1.5 hours under a nitrogen atmosphere. After cooling, the solvent was concentrated in vacuo, and the residue was heated to reflux with 2:1 acetic acid:water (50 ml) for 2 hours. After cooling, water (50 ml) was added and the precipitate was filtered, air dried and recrystallized from EtOH to give the ketone (7 g, 65%): m.p. 139–140° C. Anal. Calc'd. for $C_{15}H_{13}FOS$ (M.W. 260.33): C, 69.21; H, 5.03; S, 12.32. Found: C, 68.94; H, 5.09; S, 12.15.

Step 3 Preparation of 1-(4-Fluorophenyl)-2-(4-methylsulfonylphenyl)-1-ethanone

A solution of 1-(4-fluorophenyl)-2-(4-methylthiophenyl)-1-ethanone from step 2 (15.7 g, 60 mmol) in methanol (500 ml) and tetrahydrofuran (200 ml) was stirred at 25° C. while a solution of OXONEO (40 g, excess) in water (150 ml) was added over 45 minutes. The entire reaction mixture was stirred at 40° C. for 3 hours. Water (500 ml) was added and the precipitate was filtered and air dried. The desired ketone was recrystallized by dissolving in warm chloroform and adding hexane until cloudy. The precipitate formed by cooling the solution in a refrigerator was filtered and air dried to give the titled ketone (15 g, 80%): m.p. 185–187° C. Anal. Calc'd. for $C_{15}H_{13}FO_3S$ (M.W. 292.33): C, 61.63; H, 4.48; S, 10.97. Found: C, 61.72; H, 4.34; S, 11.01.

Step 4 Preparation of 1-(4-Methylsulfonylphenyl)-2-(4-fluorophenyl)-ethane-1,2-dione A mixture of ketone from step 3 (1 g, 3.5 mmol), selenious acid ($H_2SeO_3$) (550 mg, 1.25 equiv.), dioxane (10 ml) and water (1 ml) were heated to reflux for 4 hours and cooled. The mixture was filtered and the filtrate evaporated. The residue was triturated with cold methanol and filtered to give 620 mg (60%) of the dione: m.p. 174–175° C. Anal. Calc'd. for $C_{15}H_{11}FO_4S$ (M.W. 306.31): C, 58.82; H, 3.62; S, 10.47. Found: C, 58.70; H, 3.60; S, 10.70.

Step 5 Preparation of 5-(4-Fluorophenyl)-4-(4-methylsulfonylphenyl)-2-trifluoromethyl-1H-imidazole A mixture of dione from step 4 (1 g, 4.2 mmol), ammonium acetate (2.2 g, 5 equiv.), trifluoroacetaldehyde ethyl hemiacetal (2 g, 5 equiv.) and acetic acid (20 ml) was heated to reflux for 16 hours under an argon atmosphere. After cooling, the contents were poured into water (100 ml) and neutralized with ammonium hydroxide ($NH_4OH$) to pH 6.5. The precipitate was filtered, dried in an oven at 80° C. and recrystallized from ethyl acetate and hexane to give 5-(4-fluorophenyl)-4-(4-methylsulfonylphenyl)-2-trifluoromethyl-1H-imidazole (550 mg, 34%): m.p. 249–250° C. (dec.). Anal. Calc'd. for $C_{17}H_{12}F_4N_2O_2S$ (M.W. 384.35): C, 53.13; H, 3.15; N, 7.29; S, 8.34. Found: C, 52.91; H, 2.99; N, 6,97; S, 8.56.

Method B

Step 1 Preparation of 1-(4-Fluorophenyl)-2-(4-methylsulfonylphenyl)-bromoethane-1-one A suspension of 1-(4-fluorophenyl)-2-(methylsulfonylphenyl)-ethane-1-one (Method A, step 3) (24 g, 82 mmol) in acetic acid (500 ml) was warmed to 80° C. with stirring, and, a solution of bromine (14.38 g, 0.09 mol) in acetic acid (50 ml) was added over 15 minutes. The reaction mixture became homogeneous, was cooled and stirred an additional 3 hours at 25°. The contents were poured into water (3 L) and extracted with ethyl acetate. The organic phase was washed with aqueous $NaHCO_3$, brine and dried ($MgSO_4$). The dried solution was concentrated in vacuo to give a solid which was triturated with cold ether to produce 26.5 g (87%) of the desired haloketone: m.p. 144–145° C. Anal. Calc'd. for $C_{15}H_{12}BrFO_3S$: C, 48.53; H, 3.26; Br, 21.52; S, 8.65. Found: C, 48.34; H, 3.28; Br, 21.19; S, 8.42.

Step 2 Preparation of 5-(4-Fluorophenyl)-4-(4-methylsulfonylphenyl)-2-trifluoromethyl-1H-imidazole A mixture of 1-(4-fluorophenyl)-2-(4-methylsulfonylphenyl)-2-bromo-ethane-1-one from step one (3 g, 8.2 mmol), trifluoroacetamidine (925 mg, 8.2 mmol), $NaHCO_3$ (690 mg, 8.2 mmol) and n-butanol (30 ml) was heated to reflux for 18 hours, cooled and concentrated. The residue was dissolved in water and methylene chloride, and the organic phase was separated, dried ($Na_2SO_4$) and concentrated. The residue was purified by chromatography on silica gel using methanol/toluene (5/95) and the crude product was recrystallized from ethyl acetate and hexane to give 700 mg (22%) of purified material which was identical to the material obtained in Method A, step 5.

Method C

Step 1 Preparation of 4-Fluoro-α-(trimethylsilyl)benzeneacetonitrile

To a solution of 50.0 g (403 mmol) of 4-fluorobenzaldehyde in methylene chloride (100 ml) stirring in an ice bath under a nitrogen atmosphere, was added dropwise 54 ml (40 g, 403 mmol) of trimethylsilyl cyanide. After the addition was complete, anhydrous zinc iodide (10 mg) was added, and stirring continued overnight while the mixture warmed to room temperature. The solvent was removed by distillation under reduced pressure, and continued distillation under high vacuum gave the title compound (82.2 g) as a very pale straw yellow liquid: bp. 98–100° C. at 0.8 mm Hg.

Step 2 Preparation of 1-(4-Fluorophenyl)-2-(4-methylthiophenyl)-2-hydroxy-ethane-1-one To a cold (−70° C.) stirred solution of lithium bis (trimethylsilylamide) (11 ml of 1.0 M in tetrahydrofuran, 11 mmol) in tetrahydrofuran (20 ml) under an argon atmosphere was added a solution of trimethylsilane (TMS) protected cyanohydrin of 4-fluorobenzaldehyde from step 1 (2.2 g, 0.01 mole) over 2 minutes and the reaction mixture was stirred cold (−70° C.) for 15 minutes. A mixture of 4-thiomethylbenzaldehyde (1.52 g, 0.01 mol) in tetrahydrofuran (10 ml) was added and the reaction mixture was warmed to −50° C. for 1 hour. Saturated ammonium chloride ($NH_4Cl$) (20 ml) was added and the mixture was warmed to 25° C. Water (20 ml) and methylene chloride ($CH_2Cl_2$) (25 ml) were added and the organic phase was separated and dried ($Na_2SO_4$). The organic solvent was evaporated and the residue was dissolved in methanol (10 ml) and treated with 5% $H_2SO_4$ (5 ml) at 25° C. overnight. Ether (25 ml) and water (50 ml) were added and the ether layer was separated. The ether layer was then stirred vigorously with 0.5N NaOH (30 ml) for 15 minutes. The ether layer was dried ($Na_2SO_4$), evaporated, and the residue was purified by chromatography on silica gel with ethyl acetate/hexane (20/80) to yield 1.8 g (67%) of the titled ketone. Anal. Calc'd. for $C_{15}H_{13}OF_2S$ (M.W. 276.33): C, 65.20; H, 4.74; S, 11.60. Found: C, 65.10; H, 4.80; S, 11.75.

Step 3 Preparation of 1-(4-Methylthiophenyl)-2-(4-fluorophenyl)-ethane-1,2-dione A mixture of ketone from step 2 (1.25 g, 4.5 mmol) and bismuth oxide ($Bi_2O_3$) (2.7 g, 1.2 equiv.) in acetic acid (20 ml) was warmed to 80° C. for 30 minutes. After cooling, the mixture was filtered through Celite® filter agent and the filtrate was concentrated. The residue was dissolved in hot methanol and filtered. The solvent was concentrated under a nitrogen stream, placed in the refrigerator and the precipitate formed was filtered to give 1 g (83%) of titled dione: m.p. 96–970° C. Anal. Calc'd. for $C_{15}H_{11}FO_2S$ (M.W. 274.31): C, 65.68; H, 4.04; S, 11.69. Found: C, 65.42; H, 3.85; S, 11.42.

Step 4 Preparation of 5-(4-Fluorophenyl)-4-(4-methylthiophenyl)-2-trifluoromethyl-1H-imidazole Following the procedure of Example 1, Method A, step 5, and using the dione from step 3 above (1 g, 3.6 mmol), ammonium acetate (2.2 g, 5 equiv.), trifluoroacetaldehyde ethyl hemiacetal (1.25 g, 1.75 equiv.) and acetic acid (30 ml) gave a crude imidazole which was purified by chromatography on silica gel with toluene to afford 570 mg (45%) of the title compound.

Step 5 Preparation of 5-(4-Fluorophenyl)-4-(4-methylsulfonylphenyl)-2-trifluoromethyl-1H-imidazole A solution of imidazole from step 4 above (550 mg, 1.6 mmol) in methanol (10 ml) was stirred at 25° C. while a solution of OXONE® (1.6 g) in water (3 ml) was added. The reaction mixture was stirred for 3 hours at room temperature, poured into water (50 ml) and extracted with methylene chloride. After drying the organic layer (Na$_2$SO$_4$) and concentration, the residue was treated with cold ethyl acetate, filtered, and air dried to give 490 mg (80%) of the titled material which was identical with Examples 1 Method A and Method B.

EXAMPLE 2

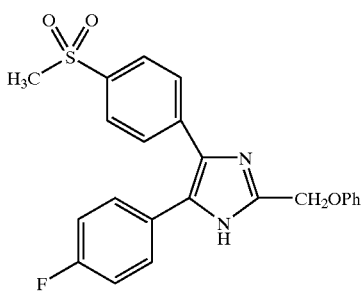

5-(4-Fluorophenyl)-4-(4-methylsulfonylphenyl)-2-phenoxymethyl-1H-imidazole

In a manner similar to Example 1, 1-(4-methylsulfonylphenyl)-2-(4-fluorophenyl)-ethane-1,2-dione (Example 1, Method A, step 4) (500 mg, 1.6 mmol), ammonium acetate (1.1 g, 5 equiv.), phenoxyacetaldehyde dimethyl acetal (800 mg, 2.5 equiv.) and acetic acid (20 ml) gave 4-(4-methylsulfonylphenyl)-5-(4-fluorophenyl)-2-phenoxymethyl-1H-imidazole (110 mg, 12%) after chromatography on silica gel using ethyl acetate/toluene (30/70) as the eluent and recrystallization from ethyl acetate and hexane: m.p. 189–190° C. Anal. Calc'd. for C$_{23}$H$_{19}$N$_2$O$_3$FS. 1/4H$_2$O (M.W. 426.98): C, 64.70; H, 4.60; N, 6.56; S, 7.51. Found: C, 64.62; H, 4.29; N, 6.22; S, 7.88.

EXAMPLE 3

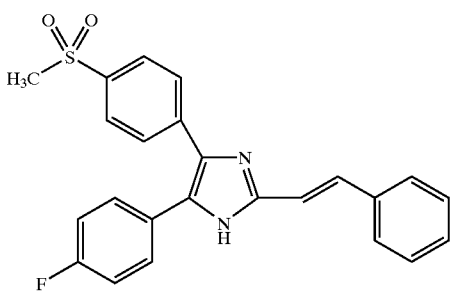

5-(4-Fluorophenyl)-4-(4-methylsulfonylphenyl)-2-(2-phenyl-trans-eth-1-ene)-1H-imidazole Following the procedure of Example 1, 1-(4-methylsulfonylphenyl)-2-(4-fluorophenyl)-ethane-1,2-dione (Example 1, Method A, step 4) (500 mg, 1.6 mmol), NH$_4$OAc (1.1 g, 14.3 mmol), trans-cinnamaldehyde (250 mg, 1.89 mmol) and acetic acid (20 ml) gave 121 mg (18%) of the desired imidazole after chromatography on silica gel with methanol:toluene (3:97) as the eluent and recrystallization from cyclohexane: m.p. 221–224° C. Anal. Calc'd. for C$_{24}$H$_{19}$N$_2$O$_2$FS (M.W. 418.49): C, 68.88; H, 4.58; N, 6.69; S, 7.66. Found: C, 68.44; H, 4.57; N, 6.45; S, 7.61.

EXAMPLE 4

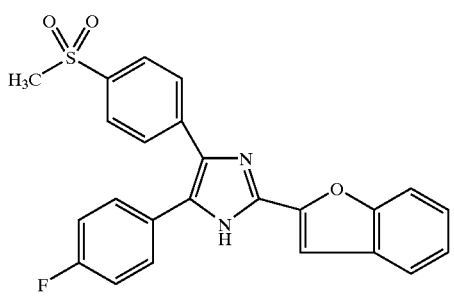

2-(2-Benzofuryl)-5-(4-fluorophenyl)-4-(4-methylsulfonylphenyl)-1H-imidazole

Following the procedure of Example 1, Method A, 1-(4-methylsulfonylphenyl)-2-(4-fluorophenyl)-ethane-1,2-dione (500 mg, 1.6 mmol), NH$_4$OAc (1.1 g, 14.3 mmol), benzofuran-2-carboxaldehyde (280 mg, 1.92 mmol) and acetic acid (20 ml) gave 2-(2-benzofuryl)-5-(4-fluorophenyl)-4-(4-methylsulfonylphenyl)-1H-imidazole (575 mg, 76%) after recrystallization from isopropanol and water: m.p. 235–237° C. Anal. Calc'd. for C$_{24}$H$_{17}$N$_2$O$_3$FS. 2H$_2$O (M.W. 468.51): C, 61.53; H, 4.52; N, 5.98; S, 6.84. Found: C, 61.39; H, 4.27; N, 5.79; S, 6.82.

EXAMPLE 5

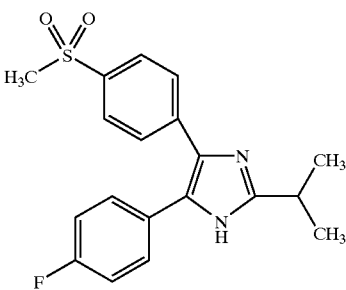

5-(4-Fluorophenyl)-2-isopropyl-4-(4-methylsulfonylphenyl)-1H-imidazole

Following the procedure of Example 1, Method A, 1-(4-methylsulfonylphenyl)-2-(4-fluorophenyl)-ethane-1,2-dione (Example 1, Method A, step 4) (500 mg, 1.6 mmol), ammonium acetate (1.1 g, 5 equiv.), isobutyraldehyde (140 mg, 1.25 equiv.) and acetic acid (20 ml) gave 4-(4-methylsulfonylphenyl)-5-(4-fluorophenyl)-2-isopropyl-1H-imidazole (380 mg, 66%) after recrystallization from ethyl acetate and hexane: m.p. 214–215° C. Anal. Calc'd. for C$_{19}$H$_{19}$N$_2$O$_2$FS (M.W. 358.44): C, 63.67; H, 5.34; N, 7.82; S, 8.95. Found: C, 63.49; H, 5.41; N, 7.62; S, 8.97.

EXAMPLE 6

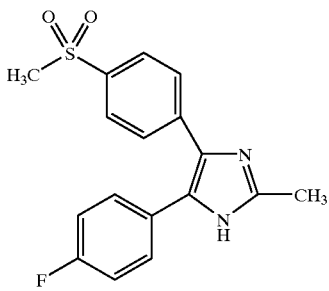

5-(4-Fluorophenyl)-2-methyl-4-(4-methylsulfonylphenyl)-1H-imidazole

Step 1 Preparation of 1-(4-Methylthiophenyl)-2-(4-fluorophenyl)-1-ethanone

A mixture of polyphosphoric acid (160 g), 4-fluorophenylacetic acid (10 g, 65 mmol) and thioanisole (10 g, 1.2 equiv.) was heated and mechanically stirred to 125° C. for 20 minutes and cooled to 50° C. Ice was added rapidly with external cooling so as to maintain the internal temperature at about 50° C. After excess ice was added, the reaction was stirred for 30 minutes, filtered, and the filter cake air dried. The crude ketone was recrystallized from EtOH to give 10 g (60%) of ketone: Anal. Calc'd. for $C_{15}H_{13}FOS$ (M.W. 260.33): C, 69.21; H, 5.03; S, 12.32. Found: C, 69.14; H, 5.00; S, 12.23.

Step 2 Preparation of 1-(4-Methylthiophenyl)-2-bromo-2-(4-fluorophenyl)-1-ethanone A mixture of 1-(4-methylthiophenyl)-2-(4-fluorophenyl)-1-ethanone from step 1 (9.48 g, 36 mmol) and acetic acid (200 ml) was stirred at 15° C. and a solution of bromine (5.80 g, 0.036 mol) in acetic acid (10 ml) was added dropwise over 5 minutes. The reaction mixture was stirred at 25° C. for an additional 2 hours. The mixture was poured into water (400 ml) with stirred for one hour. The precipitate formed was filtered, air dried and dried in vacuo at ambient temperature to give 11.4 g (93%) of the bromoketone: Anal. Calc'd. for $C_{15}H_{12}BrFOS$ (M.W. 339.23): C, 53.11; H, 3.57; S, 9.45; Br, 23.55. Found: C, 51.34; H, 3.34; S, 9.62; Br, 23.40.

Step 3 Preparation of 1-(4-Methylthiophenyl)-2-(4-Fluorophenyl)-1-ethanone-2-acetate A mixture of 1-(4-methylthiophenyl)-2-bromo-2-(4-fluorophenyl)-1-ethanone from step 2 (7.26 g, 21 mmol), sodium acetate (NaOAc) (8.6 g, 5 equiv.), dimethoxyethane (105 ml) and water (70 ml) was heated to reflux for 4 hours, cooled, poured into water (400 ml) and extracted with methylene chloride. The organic extract was dried (MgSO_4), filtered, concentrated in vacuo and the residue was purified by chromatography on silica gel with toluene to give 5 g (74%) of the acetate which slowly crystallized upon standing: Anal. Calc'd. for $C_{17}H_{15}FO_3S$ (M.W. 318.37): C, 64.14; H, 4.75; S, 10.07. Found: C, 63.89; H, 4.68; S, 9.81.

Step 4 Preparation of 4-(4-Methylthiophenyl)-5-(4-fluorophenyl)-2-methyl-1H-imidazole The 1-(4-methylthiophenyl)-2-(4-fluorophenyl)-1-ethanone-2-acetate from step 3 (700 mg, 2.2 mmol) was heated to 180° C. in formamide (10 ml) under a nitrogen atmosphere for 2 hours. After cooling, the mixture was poured into water (50 ml) and extracted with methylene chloride. The extract was dried (Na_2SO_4), evaporated, and the residue was purified by chromatography on silica gel with toluene/methanol (95/5) containing 0.5% NH_4OH to give 132 mg (20%) of imidazole: Anal. Calc'd. for $C_{17}H_{15}N_2FS$ (M.W. 298.38): C, 68.43; H, 5.07; N, 9.39; S, 10.17. Found: C, 68.14; H, 5.18; N, 9.09; S, 10.31.

Step 5 Preparation of 4-(4-Methylsulfonylphenyl)-5-(4-fluorophenyl)-2-methyl-1H-imidazole In a manner similar to Example 1, Method C, step 4, 4-(4-methylthiophenyl)-5-(4-fluorophenyl)-2-methyl-1H-imidazole (114 mg, 0.4 mmol) from step 4 was converted to 5-(4-fluorophenyl)-2-methyl-4-(4-methylsulfonylphenyl)-1H-imidazole (107 mg, 95%): Anal. Calc'd. for $C_{17}H_{15}N_2O_2FS$ (M.W. 330.38): C, 61.80; H, 4.58; N, 8.48; S, 9.71. Found: C, 61.90; H, 4.61; N, 68.35; S, 9.39.

EXAMPLE 7

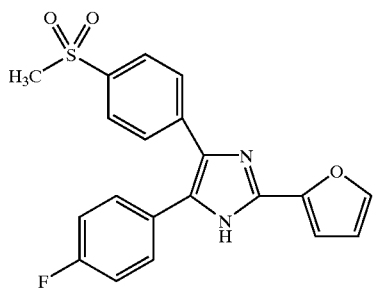

5-(4-Fluorophenyl)-2-(2-furyl)-4-(4-methylsulfonylphenyl)-1H-imidazole

In a manner similar to Example 1, Method A, 1-(4-methylsulfonylphenyl)-2-(4-fluorophenyl)-ethane-1,2-dione (Example 1, Method A, step 4) (500 mg, 1.6 mmol), ammonium acetate (1.1 g, 5 equiv.), 2-furaldehyde (170 mg, 1.1 equiv.) and acetic acid (20 ml) gave 308 mg (50%) of product after chromatography on silica gel with ethyl acetate/toluene (50/50) and recrystallization from isopropanol: m.p. 244–246° C. (dec.). Anal. Calc'd. for $C_{20}H_{15}N_2O_3FS$ (M.W. 382.42): C, 62.82; H, 3.95; N, 7.33; S, 8.38. Found: C, 62.63; H, 4.06; N, 7.13; S, 8.39.

EXAMPLE 8

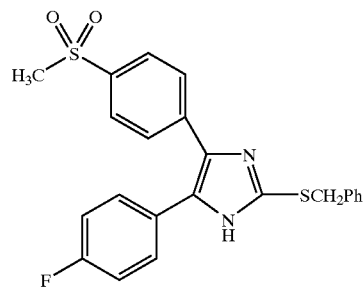

2-Benzylthio-5-(4-fluorophenyl)-4-[4-(methylsulfonyl)phenyl]-1H-imidazole

A mixture of S-benzylisothiourea hydrochloride (300 mg, 1.5 mmol), 1-(4-fluorophenyl)-2-(4-methylsulfonylphenyl)-2-bromoethan-1-one (Example 1, Method B, step 1) (500 mg, 1.3 mmol) and NaHCO_3 (500 mg, 6 mmol) in EtOH (10 ml) was heated to reflux for 3 hours. After evaporation of the solvent, the residue was treated with water (25 ml) and extracted with methylene chloride (25 ml). After drying (MgSO_4), the organic phase was evaporated. The residue was purified by chromatography on silica gel, eluting with ethyl acetate/toluene (25/75). The crude material was recrystallized from toluene and hexane to give 100 mg (17%) of titled product: m.p. 155–156° C. Anal. Calc'd. for $C_{23}H_{19}FN_2O_2S_2$: C, 62.99; H, 4.37; N, 6.39; S, 14.62. Found: C, 62.93; H, 4.41; N, 5.98; S, 14.33.

EXAMPLE 9

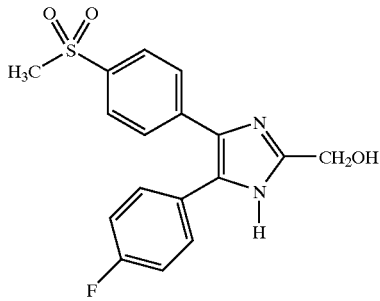

5-(4-Fluorophenyl)-2-hydroxymethyl-4-[4-(methylsulfonyl)phenyl]imidazole

Step 1 Preparation of 5-(4-Fluorophenyl)-4-(4-methylthiophenyl)-1H-imidazole 1-(4-Fluorophenyl)-2-(4-methylthiophenyl)-2-hydroxyethane-1-one (Example 1, Method C, step 1) (12.25 g, 44 mmol) was heated at 200° C. in formamide (200 ml) for 4 hours under a nitrogen atmosphere. After cooling, the reaction was poured into 1 L of ice water and stirred rapidly for 30 minutes. The precipitate was filtered and air dried. The crude material was recrystallized from EtOH to give 7.5 g (60%) of imidazole: m.p. 195–196° C. (dec.). Anal. Calc'd. for $C_{16}H_{13}N_2FS$: C, 67.58; H, 4.61; N, 9.85; S, 11.28. Found: C, 67.51; H, 4.51; N, 9.68; S, 11.33.

Step 2 Preparation of 5-(4-Fluorophenyl)-4-(4-methylthiophenyl)-1-(1-methyl-1-ethoxymethyl)-1H-imidazole A mixture of the imidazole described in step 1 (500 mg, 1.7 mmol), ethyl vinyl ether (250 mg, 3.4 mmol) and dichloroacetic acid (200 mg, 1.5 mmol) was heated to reflux in toluene (5 ml) for 6 hours. After cooling, the mixture was stirred with 1N NaOH (2 ml) for 30 minutes. The organic layer was separated and dried over $K_2CO_3$ (anhyd.) and the residue, after evaporation, was purified by chromatography on silica gel, eluting with toluene/methanol (95/5), to give 520 mg (86%) of the titled compound as an oil: Anal. Calc'd. for $C_{20}H_{21}N_2OFS$: C, 67.39; H, 5.94; N, 7.86; S, 8.99. Found: C, 67.51; H, 5.88; N, 7.55; S, 9.05.

Step 3 Preparation of 5-(4-Fluorophenyl)-4-(4-methylthiophenyl)-1H-imidazole-2-carboxaldehyde A solution of the compound from step 2 (500 mg, 1.4 mmol) and tetramethylethylenediamine (TMEDA) (186 mg, 1.6 mmol) in tetrahydrofuran (8 ml) was cooled to −70° C. under an argon atmosphere. n-Butyllithium (1.2 ml of 1.6M solution in hexane, 1.9 mmol) was added and the solution stirred at −70° C. for 15 minutes. Dimethylformamide (DMF) (140 mg, 1.9 mmol) was added and the solution was warmed to 0° C. The reaction was quenched by the addition of saturated $NaHCO_3$ solution (2 ml) and extracted with diethyl ether. The organic phase was separated and dried ($Na_2SO_4$). The drying agent was filtered and the filtrate concentrated in vacuo. The residue was treated with 2N HCl (5 ml) in EtOH (10 ml) at room temperature for 24 hours. The reaction solution was made basic with $NaHCO_3$, diluted with water (20 ml) and extracted with methylene chloride. After evaporation, the residue was purified by chromatography on silica gel, eluting with toluene/methanol (90/10), to give 350 mg (70%) of titled compound which was used immediately without further purification.

Step 4 Preparation of 5-(4-Fluorophenyl)-2-hydroxymethyl-4-(4-methylthiophenyl)-1H-imidazole A solution of compound from step 3 (350 mg, 1 mmol) and $NaBH_4$ (75 mg, 2 eq.) in methanol (10 ml) was stirred for 1 hour at 25° C. The reaction was acidified with 2N HCl (4 ml), stirred for 2 hours and placed on a steam bath for 2 minutes. After cooling, the mixture was neutralized with aqueous $NaHCO_3$ solution, extracted with methylene chloride, dried ($MgSO_4$) and evaporated. The residue was purified by chromatography on silica gel, eluting with toluene/methanol (90/10). The crude product was recrystallized from ethyl acetate/hexane to give 240 mg (78%) of pure 5-(4-fluorophenyl)-2-hydroxymethyl-4-(4-methylthiophenyl)-1H-imidazole: m.p. 108–110° C. Anal. Calc'd. for $C_{17}H_{15}N_2OFS$: C, 64.95; H, 4.81; N, 8.91; S, 10.20. Found: C, 64.69; H, 4.92; N, 8.79; S, 10.41.

Step 5 Preparation of 5-(4-Fluorophenyl)-2-hydroxymethyl-4-[4-(methylsulfonyl)phenyl]imidazole A mixture of 2-hydroxymethyl-imidazole from step 4 (150 mg, 0.4 mmol), OXONE®(450 mg, excess), water (2 ml), methanol (5 ml) and tetrahydrofuran (3 ml) was stirred at 25° C. for 2 hours. The reaction mixture was diluted with water (20 ml) and extracted with methylene chloride. After removal of solvent, the crude material was recrystallized from toluene to give 80 mg (70%) of 4-(4-fluorophenyl)-2-hydroxymethyl-5-(4-methylsulfonylphenyl)-1H-imidazole: m.p. 115–117° C. Anal. Calc'd. for $C_{17}H_{15}N_2O_3FS \cdot H_2O$: C, 56.03; 4.70; N, 7.69; S, 8.80. Found: C, 56.02; H, 4.64; N, 7.45; S, 8.90.

EXAMPLE 10

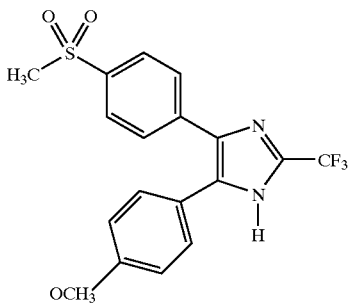

5-(3-Fluoro-4-methoxyphenyl)-4-[4-(methylsulfonyl)phenyl]-2-(trifluoromethyl)-1H-imidazole Step 1 Preparation of 3-Fluoro-4-methoxy-α-(trimethylsilyl)oxy]benzeneacetonitrile 3-Fluoro-p-anisaldehyde (15 mmol, 2.31 g) and trimethylsilyl cyanide (16 mmol, 2.13 ml) were added to $ZnI_2$ (15 mg). The mixture was stirred for 3 hours at room temperature and vacuum distilled (ca. 1 torr, 105° C.) affording the title compound as an oil (3.38 g, 89%).

Step 2 Preparation of 1-(3-Fluoro-4-methoxyphenyl)-2-hydroxy-2-[4-(methylthio)phenyl]ethanone A dry flask under an argon atmosphere containing tetrahydrofuran (25 ml) was cooled to −78° C. Lithium hex amethyldisilazide (1M in tetrahydrofuran, 15 ml) was introduced, followed by 3-fluoro-4-methoxy-α-[(trimethylsilyl)oxy]benzeneacetonitrile from step 1 (13. 4 mmol, 3.38 g), which was transferred using ca. 10 ml of tetrahydrofuran. After 20 minutes, (4-methylthio) benzaldehyde (14.4 mmol, 1.92 ml) was added. The reaction was quenched after an hour by addition of 5% HCl (60 ml) and $KHF_2$ (22 mmol, 1.75 g). The mixture was stirred for 1.5 hours at room temperature and extracted into ethyl acetate (150 ml). The organic phase was separated and stirred for 1 hour in the presence of aqueous NaOH (1.20 g in 50 ml). The organic layer was separated, dried over $MgSO_4$, concentrated in vacuo and subjected to chromatography, affording the title compound (2.00 g, 50%) as a waxy solid.

Step 3 Preparation of 1-(3-Fluoro-4-methoxyphenyl)-2-[4-(methylthio)phenyl]ethane-1,2-dione 1-(3-Fluoro-4-methoxyphenyl)-2-hydroxy-2-[4-(methylthio)phenyl]ethanone from step 2 (6.5 mmol, 2.00 g) was diluted with glacial acetic acid (30 ml). Bismuth oxide (11.4 mmol, 5.30 g) was added and the mixture was heated at 90° C. for 2 hours. The crude mixture was filtered through Celite® filter agent, lyophilized and subjected to chromatography, affording the title compound as a yellow solid (642 mg, 32%).

Step 4 Preparation of 5-(3-Fluoro-4-methoxyphenyl)-4-[4-(methylthio)phenyl]-2-(trifluoromethyl)-1H-imidazole To 1-(3-fluoro-4-methoxyphenyl)-2-([4-(methylthio) phenyl]ethane-1,2-dione from step 3 (2.1 mmol, 638 mg) was added ammonium acetate (12 mmol, 0.925 g), glacial acetic acid (10 ml) and trifluoroacetaldehyde ethyl hemiacetal (5.5 mmol, 0.64 ml). The mixture was brought to reflux. After 6 hours, additional hemiacetal (0.2 ml) was added and the mixture was heated an additional 16 hours. Lyophilization followed by chromatography (1:20 methanol in toluene) afforded the imidazole as a glass (526 mg).

Step 5 Preparation of 5-(3-Fluoro-4-methoxyphenyl)-4-[4-(methylsulfonyl)phenyl]-2-(trifluoromethyl)-1H-imidazole 4-(3-Fluoro-4-methoxyphenyl)-5-[4-(methylthio) phenyl]-2-(trifluoromethyl)-1H-imidazole (516 mg, 1.35 mmol) from step 4 was dissolved in methanol (10 ml) and cooled to 0° C. OXONE® (2.46 g, 4 mmol) in water (10 ml) was added. After the addition, the ice bath was removed and the reaction was stirred at ambient temperature for 3 hours. The mixture was extracted with chloroform (3×50 ml). The combined organic phases were dried ($MgSO_4$) and concentrated in vacuo. The residue was purified by chromatography, affording 4-(3-fluoro-4-methoxyphenyl)-5-[4-(methylsulfonyl)phenyl]-2-(trifluoromethyl)-1H-imidazole as a solid (98 mg): m.p. 228–234° C. (DSC) The structure assignment was supported by NMR. Mass spectrum (EI, m/e): 414. Anal. Calc'd. for $C_{18}H_{14}N_2F_4O_3S$: C, 52.17; H, 3.41; N, 6.76. Found: C, 52.30; H, 3.62; N, 6.53.

EXAMPLE 11

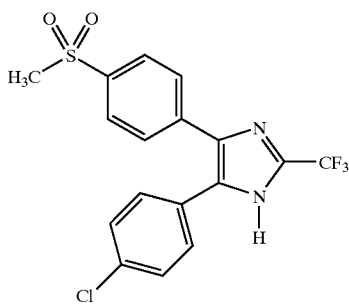

5-(4-Chlorophenyl)-4-[4-(methylsulfonyl)phenyl]-2-(trifluoromethyl)-1H-imidazole Step 1 Preparation of 4-Chloro-α-[(trimethylsilyl)oxy] benzeneacetonitrile The title compound was prepared from 4-chlorobenzaldehyde (2.81 g) by the method of Example 10, step 1 (distilled at ca. 1 torr, 98–100° C.), affording an oil (4.53 g, 94%).

Step 2 Preparation of 1-(4-Chlorophenyl)-2-hydroxy-2-[4-(methylthio)phenyl]ethanone The title compound was prepared from 4-chloro-α-[(trimethylsilyl)oxy]benzeneacetonitrile from step 1 (18.9 mmol, 4.53 g) by the method of Example 10, step 2, affording a solid (3.05 g, 55%).

Step 3 Preparation of 1-(4-Chlorophenyl)-2-[4-(methylthio)-phenyl]ethane-1,2-dione The title compound was prepared from 1-(4-chlorophenyl)-2-hydroxy-2-[4-(methylthio)phenyl] ethanone from step 2 (4.5 mmol, 1.31 g) by the method of Example 10, step 3, affording a yellow solid (929 mg, 71%).

Step 4 Preparation of 5-(4-Chlorophenyl)-4-[4-(methylthio) phenyl]-2-(trifluoromethyl)-1H-imidazole The title compound was prepared from 1-(4-chlorophenyl)-2-[4-(methylthio)phenyl]ethane-1,2-dione of step 3 (3.0 mmol, 870 mg) by the method of Example 10, step 4, affording a foam (516 mg, 47%).

Step 5 Preparation of 5-(4-Chlorophenyl)-4-[4-(methylsulfonyl)phenyl]-2-(trifluoromethyl)-1H-imidazole The title compound was prepared from 4-[4-(methylthio) phenyl]-5-(4-chlorophenyl)-2-(trifluoromethyl)-1H-imidazole from step 4 (488 mg, 1.3 mmol) by the method of Example 10, step 5, affording a solid (103 mg). The structure assignment was supported by NMR. Mass spectrum (EI, m/e): 400. Anal. Calc'd. for $C_{17}H_{12}N_2ClF_3O_2S$. 0.5 $H_2O$: C, 49.82; H, 3.20; N, 6.84. Found: C, 49.52; H, 2.98; N, 6.46.

EXAMPLE 12

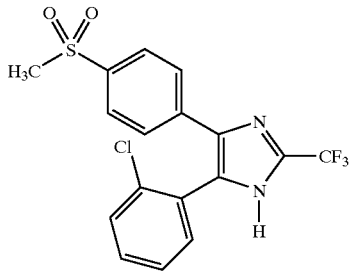

5-(2-Chlorophenyl)-4-[4-(methylsulfonyl)phenyl]-2-(trifluoromethyl)-1H-imidazole Step 1 Preparation of 2-Chloro-α-[(trimethylsilyl)oxy] benzeneacetonitrile The title compound was prepared from 2-chlorobenzaldehyde (2.81 ml) by the method of Example 10, step 1 (distilled at ca. 1 torr, 92° C.), affording an oil (5.61 g, 94%).

Step 2 Preparation of 1-(2-Chlorophenyl)-2-hydroxy-2-[4-(methylthio)phenyl]ethanone The title compound was prepared from 2-chloro-α-[(trimethylsilyl)oxy]benzeneacetonitrile (23.5 mmol, 5.61 g) from step 1 by the method of Example 10, step 2, affording a solid (1.54 g, 22%).

Step 3 Preparation of 1-(2-Chlorophenyl)-2-hydroxy-2-[4-(methylthio)phenyl]ethanone The title compound was prepared from 1-(2-chlorophenyl)-2-[4-(methylthio)phenyl]ethane-1,2-dione from step 2 (5.27 mmol, 1.54 g) by the method of Example 10, step 3, affording a yellow solid (374 mg, 24%).

Step 4 Preparation of 5-(2-Chlorophenyl)-4-[4-(methylthio)phenyl]-2-(trifluoromethyl)-1H-imidazole The title compound was prepared from 1-(2-chlorophenyl)-2-hydroxy-2-[4-(methylthio)phenyl]ethanone from step 3 (1.27 mmol, 370 mg) by the method of Example 10, step 4, affording a white solid (291 mg, 62%). Mass spectrum (EI, m/e): 368. Anal. Calc'd. for $C_{17}H_{12}N_2ClF_3S$: C, 55.36; H, 3.28; N, 7.60. Found: C, 55.46; H, 3.13; N, 7.28.

Step 5 Preparation of 5-(2-Chlorophenyl)-4-[4-(methylsulfonyl)phenyl]-2-(trifluoromethyl)-1H-imidazole 4-[4-(Methylthio)phenyl]-5-(2-chlorophenyl)-2-(trifluoromethyl)-1H-imidazole from step 4 (285 mg, 0.77 mmol) was dissolved in acetic acid (6 ml). Hydrogen peroxide (30%, 0.23 ml).was added and the solution was heated over a steam bath for 40 minutes. Lyophilization followed by chromatography afforded the title compound as a white foam (133 mg). The structure assignment was supported by NMR. Mass spectrum (EI, m/e): 400. Anal. Calc'd. for $C_{17}H_{12}N_2ClF_3O_2S$: C, 50.80; H, 2.92; N, 6.76. Found: C, 50.94; H, 3.02; N, 6.99.

EXAMPLE 13

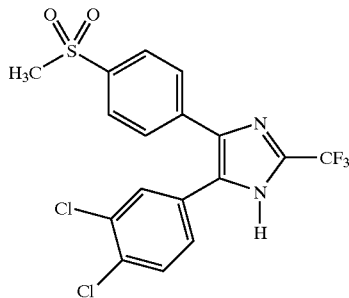

5-(3,4-Dichlorophenyl)-4-[4-(methylsulfonyl)phenyl]-2-(trifluoromethyl)-1H-imidazole Step 1 Preparation of 3,4-Dichloro-α-[(trimethylsilyl)oxy] benzeneacetonitrile The title compound was prepared from 3,4-dichlorobenzaldehyde (25 mmol, 4.375 g) by the method of Example 10, step 1 (distilled at ca. 1 torr, 115° C.), affording the title compound as an oil (6.49 g, 95%).

Step 2 Preparation of 1-(3,4-Dichlorophenyl)-2-hydroxy-2-[4-(methylthio)phenyl]ethanone A dry flask under an argon atmosphere containing tetrahydrofuran (50 ml) was cooled to −78° C. Lithium hexamethyldisilazide (1M in tetrahydrofuran, 25 ml) was introduced, followed by a solution of 3,4-dichloro-α-[(trimethylsilyl)oxy]benzeneacetonitrile from step 1 (23.7 mmol, 6.49 g) in tetrahydrofuran (10 ml). After 20 minutes, (4-methylthio)benzaldehyde (25 mmol, 3.33 ml) was added. The reaction was quenched after an hour by addition of 10% HCl (100 ml) and $KHF_2$ (40 mmol, 3.12 g). The mixture was stirred 45 minutes at room temperature, then extracted into ethyl acetate (200 ml). The organic phase was separated, washed with saturated NaCl solution (50 ml), then stirred for 1 hour in the presence of aqueous NaOH (1.14 g in 50 ml). The organic layer was separated, dried over $MgSO_4$, concentrated in vacuo and subjected to chromatography on silica gel (2:1 hexane/ethyl acetate), affording the title compound (2.32 g, 30%) as a waxy solid.

Step 3 Preparation of 1-(3,4-Dichlorophenyl)-2-[4-(methylthio)phenyl]ethane-1,2-dione Dimethyl sulfoxide (16.3 mmol, 1.20 ml) was added to methylene chloride (70 ml) and the solution was cooled to −65° C. Trifluoroacetic acid anhydride (13.1 mmol, 1.84 ml) was added over 2 minutes and the cold solution was stirred an additional 10 minutes. A solution of 1-(3,4-dichlorophenyl)-2-hydroxy-2-[4-(methylthio)phenyl] ethanone from step 2 (7.10 mmol, 2.32 g) in methylene chloride (ca. 10 ml) was introduced and after 30 minutes, triethylamine (32.6 mmol, 4.53 ml) was added. The mixture was warmed to 0° C. over 30 minutes, diluted with water (60 ml) and extracted with ethyl acetate (200 ml). The organic phase was separated, dried over magnesium sulfate, filtered through silica gel, and concentrated in vacuo. The residue was subjected to chromatography on silica gel using mixtures of hexane and ethyl acetate as eluents, affording the title compound as a yellow solid (2.035 g, 88%). Step 4 Preparation of 5-(3,4-Dichlorophenyl)-4-[4-(methylthio) phenyl]-2-(trifluoromethyl)-1H-imidazole The title compound was prepared from 1-(3,4-dichlorophenyl)-2-[4-(methylthio)phenyl]ethane-1,2-dione from step 3 (6.26 mmol, 2.035 g) by the method of Example 10, step 4, affording a viscous oil (1.374 g, 54%). Step 5 Preparation of 5-(3,4-Dichlorophenyl)-4-[4-(methylsulfonyl)phenyl]-2-(trifluoromethyl)-1H-imidazole The title compound was prepared from 5-(3,4-dichlorophenyl)-4-[4-(methylthio)phenyl]-2-(trifluoromethyl)-1H-imidazole from step 4 (3.41 mmol, 1.374 g) by the method of Example 12, step 5, affording, after two recrystallizations from ethyl acetate and hexane, a solid (395 mg): m.p. 249–251° C. (DSC). The structure assignment was supported by NMR. Anal. Calc'd. for $C_{17}H_{11}Cl_2F_3O_2S$: C, 46.91; H, 2.55; N, 6.44. Found: C, 47.15; H, 2.93; N, 5.91.

EXAMPLE 14

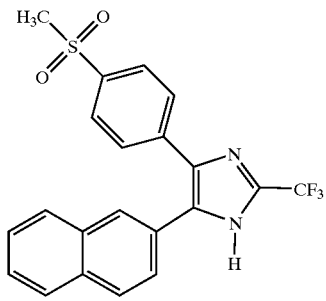

4-[4-(Methylsulfonyl)phenyl]-3-(2-naphthyl)-2-(trifluoromethyl)-1H-imidazole

Step 1 Preparation of α-[(Trimethylsilyl)oxy]-2-naphthylacetonitrile.

The title compound was prepared from 2-naphthaldehyde (25 mmol, 3.90 g) by the method of Example 10, step 1, (distilled at ca 1 torr, 110° C.),. affording an oil (4.896 g, 77%).

Step 2 Preparation of 2-Hydroxy-2-[4-(methylthio)phenyl]-1-(2-naphthyl)-ethanone The title compound was prepared from α-[(trimethylsilyl)oxy]-2-naphthylacetonitrile from step 1 (19.2 mmol, 4.89 g) by the method of Example 13, step 2, affording a solid (3.28 g, 55%).

Step 3 Preparation of 2-[4-(Methylthio)phenyl]-1-(2-naphthyl)ethane-1,2-dione

The title compound was prepared from 2-hydroxy-2-[4-(methylthio)phenyl]-1-(2-naphthyl)-ethanone from step 2 above (6.50 mmol, 2.00 g) using the method of Example 10, step 3, affording a yellow solid (968 mg, 49%).

Step 4 Preparation of 4-[4-(Methylthio)phenyl]-5-(2-naphthyl)-2-(trifluoromethyl)-1H-imidazole The title compound was prepared from 2-[4-(methylthio)phenyl]-1-(2-naphthyl)ethane-1,2-dione (3.14 mmol, 960 mg) from step 3 above by the method of Example 10, step 4, affording a white solid (675 mg, 56%).

Step 5 Preparation of 4-[4-(Methylsulfonyl)phenyl]-5-(2-naphthyl)-2-(trifluoromethyl)-1H-imidazole The title compound was prepared from 4-[4-(methylthio)phenyl]-5-(2-naphthyl)-2-(trifluoromethyl)-1H-imidazole of step 4 above (1.77 mmol, 675 mg) by the method of Example 12, step 5, affording, after recrystallization from acetone and hexane, a solid (393 mg, 54%). The solid was diluted with acetone (ca. 1 ml) and concentrated in vacuo to remove traces of hexane: m.p. 228–230° C. (DSC). The structure assignment was supported by NMR. Mass spectrum (EI , M/e): 416. Anal. Calc'd. for $C_{21}H_{15}F_3N_2O_2S$: C, 60.57; H, 3.63; N, 6.73. Found: C, 60.13; H, 3.97; N, 6.34.

EXAMPLE 15

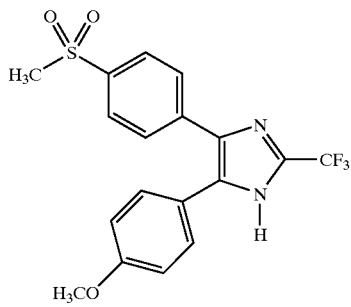

5-(4-Methoxyphenyl)-4-[4-(methylsulfonyl)phenyl]-2-(trifluoromethyl)-1H-imidazole Step 1 Preparation of 4-Methoxy-α-[(trimethylsilyl)oxy]benzeneacetonitrile The title compound was prepared from p-anisaldehyde (25 mmol, 3.03 ml) by the method of Example 10, step 1 (distilled at ca. 1 torr, 102° C.), affording an oil (5.74 g, 98%).

Step 2 Preparation of 2-Hydroxy-1-(4-methoxyphenyl)-2-[4-(methylthio)phenyl]ethanone The title compound was prepared from 4-methoxy-α-[(trimethylsilyl)oxy]benzeneacetonitrile from step 1 above (24.4 mmol, 5.74 g) by the method of Example 13, step 2, affording a solid (5.53 g, 79%).

Step 3 Preparation of 1-(4-Methoxyphenyl)-2-[4-(methylthio)phenyl]ethane-1,2-dione The title compound was prepared from 2-hydroxy-1-(4-methoxyphenyl)-2-[4-(methylthio)phenyl]ethanone from step 2 (5.64 mmol, 1.63 g) using the method of Example 10, step 3, affording a yellow solid (968 mg, 60%).

Step 4 Preparation of 5-(4-Methoxyphenyl)-4-[4-(methylthio)phenyl]-2-(trifluoromethyl)-1H-imidazole The title compound was prepared from 1-(4-methoxyphenyl)-2-[4-(methylthio)phenyl]ethane-1,2-dione from step 3 (3.33 mmol, 952 mg) by the method of Example 10, step 4, affording a viscous oil (411 mg, 34%).

Step 5 Preparation of 5-(4-Methoxyphenyl)-4-[4-(methylsulfonyl)phenyl]-2-(trifluoromethyl)-1H-imidazole The title compound was prepared from 5-(4-methoxyphenyl)-4-[4-(methylthio)phenyl]-2-(trifluoromethyl)-1H-imidazole from step 4 (1.12 mmol, 0.408 g) by the method of Example 12, step 5, affording, after recrystallization from ethyl acetate and hexane, a solid (236 mg, 53%). The solid was diluted with acetone (ca. 1 ml) and concentrated in vacuo to remove traces of hexane. The structure assignment was supported by NMR. Anal. Calc'd. for $C_{18}H_{15}F_3N_2O_3S$: C, 54.54; H, 3.81; N, 7.07. Found: C, 54.83; H, 3.83; N, 6.62.

EXAMPLE 16

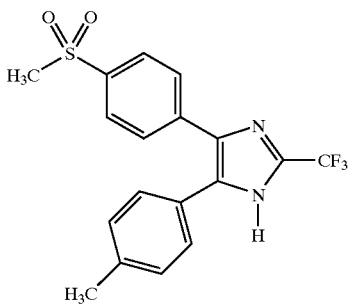

5-(4-Methylphenyl)-4-[4-(methylsulfonyl)phenyl]-2-(trifluoromethyl)-1H-imidazole Step 1 Preparation of 4-Methyl-α-[(trimethylsilyl)oxy]benzeneacetonitrile The title compound was prepared from p-tolualdehyde (25 mmol, 2.94 ml) by the method of Example 10, step 1 (distilled at ca. 1 torr, 96° C.), affording an oil (5.23 g, 96%).

Step 2 Preparation of 2-Hydroxy-1-(4-methylphenyl)-2-[4-(methylthio)phenyl]-ethanone The title compound was prepared from 4-methyl-α-[(trimethylsilyl)oxy]benzeneacetonitrile from step 1 (23.7 mmol, 5.20 g) by the method of Example 13, step 2, affording a solid (5.53 g, 70%).

Step 3 Preparation of 1-(4-Methylphenyl)-2-[4-(methylthio)phenyl]ethane-1,2-dione The title compound was prepared from 2-hydroxy-1-(4-methoxyphenyl)-2-[4-(methylthio)phenyl]ethanone from step 2 (5.64 mmol, 1.63 g) using the method of Example 10, step 3, affording a yellow solid (968 mg, 60%).

Step 4 Preparation of 5-(4-Methylphenyl)-4-[4-(methylthio)phenyl]-2-(trifluoromethyl)-1H-imidazole The title compound was prepared from 1-(4-methylphenyl)-2-[4-(methylthio)phenyl]ethane-1,2-dione from step 3 (3.29 mmol, 889 mg) by the method of Example 10, step 4, affording a viscous oil (345 mg, 30%).

Step 5 Preparation of 5-(4-Methylphenyl)-4-[4-(methylsulfonyl)phenyl]-2-(trifluoromethyl)-1H-imidazole The title compound was prepared from 5-(4-methylphenyl)-4-[4-(methylthio)phenyl]-2-(trifluoromethyl)-1H-imidazole from step 4 (1.00 mmol, 0.345 mg) by the method of Example 12, step 5, affording,

EXAMPLE 17

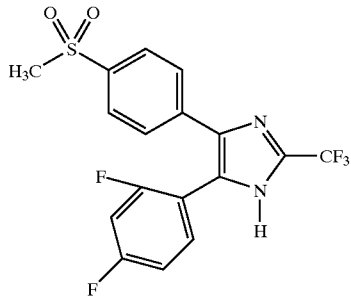

5-(2,4-Difluorophenyl)-4-[4-(methylsulfonyl)
phenyl]-2-(trifluoromethyl)-1H-imidazole Step 1 Preparation of 2,4-Difluoro-α-[(trimethylsilyl)oxy] benzeneacetonitrile The title compound was prepared from 2,4-difluorobenzaldehyde (25 mmol, 2.73 ml) by the method of Example 10, step 1 (distilled at ca. 1 torr, 80° C.), affording an oil (5.83 g, 97%).

Step 2 Preparation of 1-(2,4-Difluorophenyl)-2-hydroxy-2-[4-(methylthio)phenyl]-ethanone The title compound was prepared from 2,4-difluoro-α-[(trimethylsilyl)oxy]benzeneacetonitrile from step 1 (24.2 mmol, 5.85 g) by the method of Example 13, step 2, affording a solid (3.63 g, 51%).

Step 3 Preparation of 1-(2,4-Difluorophenyl)-2-[4-(methylthio)phenyl]ethane-1,2-dione The title compound was prepared from 1-(2,4-difluorophenyl)-2-hydroxy-2-[4-(methylthio)phenyl]-ethanone from step 2 (12.3 mmol, 3.63 g) using the method of Example 10, step 3, affording a yellow solid (1.57 g, 44%).

Step 4 Preparation of 5-(2,4-Difluorophenyl)-4-[4-(methylthio)phenyl]-2-(trifluoromethyl)-1H-imidazole The title compound was prepared from 1-(2,4-difluorophenyl)-2-[4-(methylthio)phenyl]ethane-1,2-dione from step 3 (5.38 mmol, 1.57 g) by the method of Example 10, step 4, affording a viscous oil (938 mg, 47%).

Step 5 Preparation of 5-(2,4-Difluorophenyl)-4-[4-(methylsulfonyl)phenyl]-2-(trifluoromethyl)-1H-imidazole The title compound was prepared from 5-(2,4-difluorophenyl)-4-[4-(methylthio)phenyl]-2-(trifluoromethyl)-1H-imidazole from step 4 (2.53 mmol, 0.938 g) by the method of Example 12, step 5, affording, after recrystallization from ethyl acetate and hexane, a solid (487 mg, 48%). The solid was diluted with acetone (ca. 1 ml) and concentrated in vacuo to remove traces of hexane. The structure assignment was supported by NMR. Mass Spectrum (EI, M/e) : 402. Anal. Calc'd. for $C_{17}H_{11}F_5O_2S$: C, 50.75; H, 2.76; N, 6.96. Found: C, 50.83; H, 2.59; N, 6.79.

EXAMPLE 18

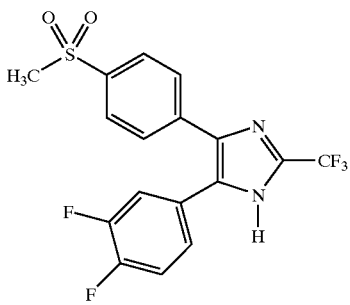

5-(3,4-Difluorophenyl)-4-[4-(methylsulfonyl)
phenyl]-2-(trifluoromethyl)-1H-imidazole Step 1 Preparation of 3,4-Difluoro-α-[(trimethylsilyl)oxy] benzeneacetonitrile The title compound was prepared from 3,4-difluorobenzaldehyde (25 mmol, 2.73 ml) by the method of Example 10, step 1 (distilled at ca. 1 torr, 80° C.), affording an oil (6.02 g, 100%).

Step 2 Preparation of 1-(3,4-Difluorophenyl)-2-hydroxy-2-[4-(methylthio)phenyl]-ethanone The title compound was prepared from 3,4-difluoro-α-[(trimethylsilyl)oxy]benzeneacetonitrile from step 1 above (25 mmol, 6.02 g) by the method of Example 13, step 2, affording a solid (1.83 g, 25%).

Step 3 Preparation of 1-(3,4-Difluorophenyl)-2-[4-(methylthio)phenyl]ethane-1,2-dione The title compound was prepared from 1-(3,4-difluorophenyl)-2-hydroxy-2-[4-(methylthio)phenyl]-ethanone from step 2 (6.23 mmol, 1.83 g). using the method of Example 10, step 3, affording a yellow solid (985 g, 54%).

Step 4 Preparation of 5-(3,4-Difluorophenyl)-4-[4-(methylthio)phenyl]-2-(trifluoromethyl)-1H-imidazole The title compound was prepared from 1-(3,4-difluorophenyl)-2-[4-(methylthio)phenyl]ethane-1,2-dione from step 3 (3.37 mmol, 985 mg) by the method of Example 10, step 4, affording a viscous oil (606 mg, 49%).

Step 5 Preparation of 5-(3,4-Difluorophenyl)-4-[4-(methylsulfonyl)phenyl]-2-(trifluoromethyl)-1H-imidazole The title compound was prepared from 5-(3,4-difluorophenyl)-4-[4-(methylthio)phenyl]-2-(trifluoromethyl)-1H-imidazole from step 4 (1.64 mmol, 0.606 g) by the method of Example 12, step 5, affording, after recrystallization from acetone, a solid (313 mg, 47%). The solid was diluted with acetone (ca. 1 ml) and concentrated in vacuo to remove traces of hexane: m.p. 249–252° C. (DSC). The structure assignment was supported by NMR. Anal. Calc'd. for $C_{17}H_{11}F_5O_2S$: C, 50.75; H, 2.76; N, 6.96. Found: C, 50.58; H, 2.96; N, 6.66.

EXAMPLE 19

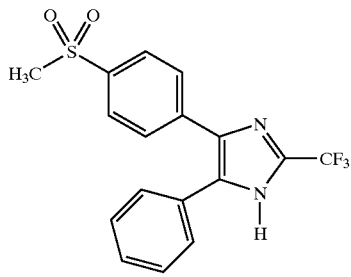

4-[4-(Methylsulfonyl)phenyl]-5-phenyl-2-(trifluoromethyl)-1H-imidazole

Step 1 Preparation of α-(Trimethylsilyl)oxy]benzeneacetonitrile

The title compound was prepared from benzaldehyde (25 mmol, 2.55 ml) by the method of Example 10, step 1 (distilled at ca. 1 torr, 86° C.), affording an oil (4.52 g, 88%).

Step 2 Preparation of 2-Hydroxy-2-[4-(methylthio)phenyl]-1-phenyl-ethanone

The title compound was prepared from α-(trimethylsilyl)oxy]benzeneacetonitrile from step 1 (22 mmol, 4.52 g) by the method of Example 13, step 2, affording a solid (3.25 g, 57%).

Step 3 Preparation of 2-[4-(Methylthio)phenyl]-1-(phenyl)ethane-1,2-dione

The title compound was prepared from 2-hydroxy-2-[4-(methylthio)phenyl]-1-phenyl-ethanone from step 2 (12.6 mmol, 3.25 g) using the method of Example 10, step 3, affording a yellow solid (1.50 g, 46%).

Step 4 Preparation of 4-[4-(Methylthio)phenyl]-5-phenyl-2-(trifluoromethyl)-1H-imidazole The title compound was prepared from 2-[4-(methylthio)phenyl]-1-(phenyl)ethane-1,2-dione from step 3 (5.87 mmol, 1.50 g) by the method of Example 10, step 4, affording a viscous oil (918 mg, 47%).

Step 5 Preparation of 4-[4-(Methylsulfonyl)phenyl]-5-phenyl-2-(trifluoromethyl)-1H-imidazole The title compound was prepared from 4-([4-(methylthio)phenyl]-5-phenyl-2-(trifluoromethyl)-1H-imidazole from step 4 (2.75 mmol, 0.918 g) by the method of Example 12, step 5, affording, after recrystallization from acetone, a solid (489 mg, 45%). The solid was diluted with acetone (ca 1 ml) and concentrated in vacuo to remove traces of hexane: m.p. 228–230° C. (DSC). The structure assignment was supported by NMR. Mass spectrum (EI, M/e): 366. Anal. Calc'd. for $C_{17}H_{12}F_3O_2S$: C, 55.73; H, 3.58; N, 7.65. Found: C, 55.58; H, 3.66; N, 7.31.

EXAMPLE 20

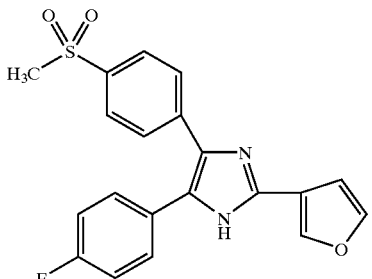

5-(4-Fluorophenyl)-2-(3-furyl)-4-(4-methylsulfonylphenyl)-1H-imidazole

In a manner similar to Example 1, Method A, 1-(4-methylsulfonylphenyl)-2-(4-fluorophenyl)-ethane-1,2-dione (Example 1, Method A, step 4) (1 g, 3.3 mmol), ammonium acetate (2 g, 25.9 mmol), 3-furaldehyde (350 mg, 3.64 mmol) and acetic acid (20 ml) gave 500 mg (47%) product after recrystallization from ethanol and water. m.p. 233–235° C. (dec.). Anal. Calc'd. for $C_{20}H_{15}N_2O_3FS$ (M.W. 382.42): C, 62.82; H, 3.95; N, 7.33; S, 8.38. Found: C, 62.50; H, 3.90; N, 7.04; S, 8.25.

EXAMPLE 21

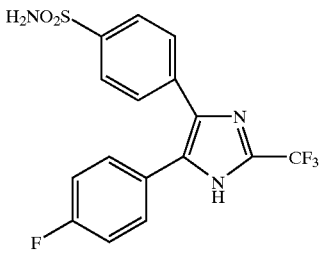

4-[5-(4-Fluorophenyl)-2-(trifluoromethyl)-1H-imidazol-4-yl]benzenesulfonamide

Step 1 Preparation of 5-(4-Fluorophenyl)-4-(4-methylsulfonylphenyl)-2-trifluoromethyl-1-(2-trimethylsilylethoxymethyl)-1H-imidazole A mixture of hexane-washed sodium hydride (NaH) (110 mg of 60%, 2.8 mmol) in dimethylformamide (DMF) (15 ml) was stirred under a nitrogen atmosphere at 25° C. and a solution of 5-(4-fluorophenyl)-4-(4-methylsulfonylphenyl)-2-trifluoromethyl-1H-imidazole (Example 1) (970 mg, 2.5 mmol) in DMF (5 ml) was added over 15 minutes. This mixture was stirred an additional 30 minutes. Trimethylsilylethoxymethyl chloride (450 mg, 3 mmol) was added and the reaction mixture was stirred for 16 hours at 25° C. The reaction mixture was poured into 2% aqueous NH$_4$Cl (150 ml) and extracted with ethyl acetate. After drying (Na$_2$SO$_4$) and solvent removal, the protected sulfone imidazole (1.1 g, 95%) was essentially pure and was used without further purification.

Step 2 Preparation of 4-[5-(4-Fluorophenyl)-2-trifluoromethyl-1-(2-trimethylsilylethoxymethyl)-1H-imidazol-4-yl]benzenesulfonamide To a solution of the protected sulfone imidazole from step 1 (1.1 g, 2.0 mmol) in THF (15 ml) at 0° C. under an argon atmosphere, n-butyl magnesium bromide (n-BuMgBr) (2M solution in THF, 4.5 ml) was added and the temperature warmed to 25° C. over 30 minutes. Triethylborane (Et₃B) (1M solution in THF, 9 ml) was added and the reaction was heated to reflux for 48 hours. The reaction mixture was cooled to 25° C. and a mixture of hydroxylamine-O-sulfonic acid (NH₂OSO₃H) (2 g) and sodium acetate (2 g) in water (8 ml) was added and rapidly stirred at 25° C. for 16 hours. Water (50 ml) was added and the product was extracted with ethyl acetate, dried (Na₂SO₄), and evaporated. The residue was purified by chromatography on silica gel using mixtures of ethyl acetate and toluene as the eluent to give 500 mg (45%) of the desired protected sulfonamide. The product was used directly in the next step.

Step 3 Preparation of 4-[5-(4-Fluorophenyl)-2-trifluoromethyl-1H-imidazol-4-yl]benzenesulfonamide A solution of protected sulfonamide from step 2 (500 mg, 1 mmol) in a solution of 3 N HCl (5 ml) in EtOH (4 ml) was heated to reflux for 1 hour, cooled and diluted with water (20 ml). The resulting mixture was extracted with methylene chloride, dried (Na₂SO₄) and the solvent was evaporated. The residue was recrystallized from toluene containing a small amount of ethyl acetate to give the title product (150 mg, 40%): m.p. 259–260° C. Anal. Calc'd. for $C_{16}H_{11}N_3O_2F_4S$: C, 49.87; H, 2.88; N, 10.90; S, 8.32. Found: C, 50.30; H, 3.10; N, 10.55; S, 8.73.

The following imidazole derivatives could be prepared by the procedure described in Example 21:

Example 22 4-[5-(4-fluorophenyl)-2-phenoxymethyl-1H-imidazol-4-yl]benzenesulfonamide;

Example 23 4-[5-(4-fluorophenyl)-2-(2-phenyl-trans-eth-1-ene)-1H-imidazol-4-yl]benzenesulfonamide;

Example 24 4-[2-(2-benzofuryl)-5-(4-fluorophenyl)-1H-imidazol-4-yl]benzenesulfonamide;

Example 25 4-[5-(4-fluorophenyl)-2-isopropyl-1H-imidazol-4-yl]benzenesulfonamide;

Example 26 4-[5-(4-fluorophenyl)-2-methyl-1H-imidazol-4-yl]benzenesulfonamide;

Example 27 4-[5-(4-fluorophenyl)-2-(2-furyl)-1H-imidazol-4-yl]benzenesulfonamide;

Example 28 4-[2-benzylthio-5-(4-fluorophenyl)-1H-imidazol-4-yl]benzenesulfonamide;

Example 29 4-[5-(4-fluorophenyl)-2-hydroxymethyl-1H-imidazol-4-yl]benzenesulfonamide;

Example 30 4-[5-(3-fluoro-4-methoxyphenyl)-2-(trifluoromethyl)-1H-imidazol-4-yl]benzenesulfonamide;

Example 31 4-[5-(4-chlorophenyl)-2-(trifluoromethyl)-1H-imidazol-4-yl]benzenesulfonamide;

Example 32 4-[5-(2-chlorophenyl)-2-(trifluoromethyl)-1H-imidazol-4-yl]benzenesulfonamide;

Example 33 4-[5-(3,4-dichlorophenyl)-2-(trifluoromethyl)-1H-imidazol-4-yl]benzenesulfonamide;

Example 34 4-[5-(2-naphthyl)-2-(trifluoromethyl)-1H-imidazol-4-yl]benzenesulfonamide;

Example 35 4-[5-(4-methoxyphenyl)-2-(trifluoromethyl)-1H-imidazol-4-yl]benzenesulfonamide;

Example 36 4-[5-(4-methylphenyl)-2-(trifluoromethyl)-1H-imidazol-4-yl]benzenesulfonamide;

Example 37 4-[5-(2,4-difluorophenyl)-2-(trifluoromethyl)-1H-imidazol-4-yl]benzenesulfonamide;

Example 38 4-[5-(3,4-difluorophenyl)-2-(trifluoromethyl)-1H-imidazol-4-yl]benzenesulfonamide;

Example 39 4-[5-phenyl-2-(trifluoromethyl)-1H-imidazol-4-yl]benzenesulfonamide; and Example 40 4-[5-(4-fluorophenyl)-2-(3-furyl)-1H-imidazol-4-yl]benzenesulfonamide.

EXAMPLE 41

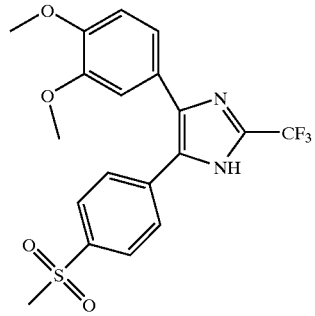

4-(3,4-Dimethoxyphenyl)-5-[4-(methylsulfonyl)phenyl]-2-(trifluoromethyl)-1H-imidazole Step 1 Preparation of 4-Methylthiobenzaldehyde-trimethylsilylcyanohydrin 4-Methylthiobenzaldehyde (38.5 g, 0.25 mol) was added dropwise over 30 minutes to a stirred mixture of trimethylsilylcyanide (25 g, 0.25 mol) and zinc iodide (150 mg) at 25° C. under a nitrogen atmosphere. After stirring overnight, the reaction mixture was distilled to give 25 g (51%) of desired liquid: bp 120–125° C. (0.1 mm Hg). Anal. Calc'd. for $C_{12}H_{17}NOSiS$ (MW 251.43): C, 57.33; H, 6.82; N, 5.57; S, 12.75. Found: C, 57.11; H, 6.71; N, 5.49; S, 12.99.

Step 2 Preparation of 4-Methylthiophenyl-3',4'-dimethoxyphenyl Benzoin

To a cold (−70° C.) stirred solution of lithium bis(trimethylsilyl)amide (23 ml of a 1M solution in tetrahydrofuran, 23 mmol) was added a solution of 4-methylthiobenzaldehyde-trimethylsilylcyanohydrin (Step 1) (5 g, 20 mmol) in tetrahydrofuran (25 ml) dropwise over 15 minutes. After stirring for an additional 5 minutes, a solution of 3,4-dimethoxybenzaldehyde (3.3 g, 20 mmol) in tetrahydrofuran (20 ml) was added dropwise over 5 minutes. The reaction was stirred for 30 minutes at −70° C. and then warmed to room temperature. After stirring for 3 hours, the reaction was quenched by adding 3N sulfuric acid (50 ml) and warming at 40° C. for 3 hours. After cooling, the reaction mixture was partitioned between ethyl ether and water and the layers separated. The organic layer was stirred with 1N sodium hydroxide (100 ml) for 1 hour and the layers were separated. The organic layer was washed with brine and dried over sodium sulfate. The drying agent was filtered and the filtrate concentrated in vacuo to give the crude product as an oil. Chromatography of the oil on silica gel using 30% ethyl acetate/hexane gave 2.3 g (35%) of the desired benzoin as an oil that crystallized on standing: mp 88–91° C. Anal. Calc'd. for $C_{17}H_{18}O_4S$ (MW 318.40): C, 64.13; H, 5.70; S, 10.07. Found: C, 63.92; H, 5.51; S, 10.31.

Step 3 Preparation of 4-Methylthiophenyl-3',4'-dimethoxyphenyl Benzil

A mixture of the benzoin from Step 2 (2.2 g, 6.9 mmol) and bismuth oxide (4 g, 8.6 mmol) in acetic acid (25 ml) was heated at 90° C. for 45 minutes. The hot reaction mixture was filtered and the filtrate concentrated in vacuo to give 2.0 g (90%) of a solid suitable for use without further purification: mp 109–110° C. Anal. Calc'd. for $C_{17}H_{16}O_4S$ (MW 316.40): C, 64.54; H, 5.10; S, 10.13. Found: C, 64.59; H, 5.02; S, 10.29.

Step 4 Preparation of 4-Methylsulfonylphenyl-3',4'-dimethoxyphenyl Benzil

A solution of Oxone®(9.8 g, 16 mmol) in water (50 ml) was added dropwise over 15 minutes to a solution of the benzil from Step 3 (2.0 g, 63 mmol) in a methanol:tetrahydrofuran solution (2:1, 100 ml). The reaction mixture was warmed to 40° C. for 2 hours, cooled and poured into water (500 ml). The solid precipitate was filtered and air dried to give 2.0 g (95%) of desired product as a solid: mp 181–183° C. Anal. Calc'd. for $C_{17}H_{16}O_6S$ (MW 348.38): C, 58.61; H, 4.63; S, 9.20. Found: C, 58.55; H, 4.49; S, 9.29.

Step 5 Preparation of 4-(3,4-Dimethoxyphenyl)-5-[4-(methylsulfonyl)phenyl]-2-(trifluoromethyl)-1H-imidazole A mixture of 4-methylsulfonylphenyl-3',4'-dimethoxyphenyl benzil (Step 4) (2 g, 5.7 mmol), ammonium acetate (2.65 g, 34 mmol) and trifluoroacetaldehyde ethyl hemiacetal (1.90 g) in acetic acid was heated at reflux with stirring overnight under a nitrogen atmosphere. The reaction was cooled, poured into water and the resulting precipitate filtered and air dried. The crude product was purified by chromatography on silica gel using 2% methanol in methylene chloride as the eluent to give 1.1 g (51%) of the title product: mp 221–224° C. Anal. Calc'd. for $C_{19}H_{17}N_2F_3O_4S$ (MW 426.41): C, 53.52; H, 4.02; N, 6.57; S, 7.52. Found: C, 53.35; H, 4.07; N, 6.51; S, 7.85.

EXAMPLE 42

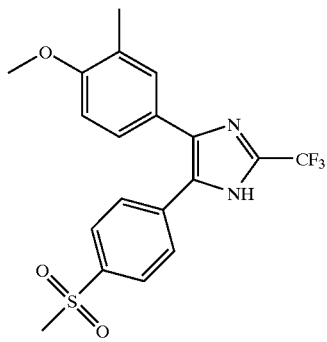

4-(4-Methoxy-3-methylphenyl)-5-[4-(methylsulfonyl)phenyl]-2-(trifluoromethyl)-1H-imidazole Step 1 Preparation of 4-Methylthiophenyl-3'-methyl-4'-methoxyphenyl Benzoin The benzoin was synthesized according to the procedure of Example 41, step 2 using the product of Example 41, Step 1 (5 g, 20 mmol), 3-methyl-4-methoxybenzaldehyde (3 g, 20 mmol) and 1M lithium bis(trimethylsilyl)amide in tetrahydrofuran (23 ml, 23 mmol). The crude product was purified by chromatography on silica gel using 30% ethyl acetate in hexane to give 4.1 g (68%) of the compound as a crystalline solid: mp 101–103° C. Anal. Calc'd. for $C_{17}H_{18}O_3S$ (MW 302.40): C, 67.52; H, 6.00; S, 10.60. Found: C, 67.33; H, 5.89; S, 10.75.

Step 2 Preparation of 4-Methylthiophenyl-3'-methyl-4'-methoxyphenyl Benzil

The benzil was synthesized according to the procedure of Example 41, Step 3 using the benzoin of Step 1 (4.1 g, 13.5 mmol) and bismuth oxide (7.9 g, 16.9 mmol) in acetic acid. There was obtained 4 g (95%) of the desired compound as a crystalline solid: mp 134–136° C. Anal. Calc'd. for $C_{17}H_{16}O_3S$ (MW 300.39): C, 67.98; H, 5.37; S, 10.67. Found: C, 68.00; H, 5.20; S, 10.79.

Step 3 Preparation of 2-Trifluoromethyl-4-(4-methylthiophenyl)-5-(3-methyl-4-methoxyphenyl)-1H-imidazole The imidazole was synthesized according to the procedure of Example 41, Step 5 using the product of Step 2 (1.6 g, 5.3 mmol), ammonium acetate (2.8 g, 37 mmol) and trifluoroacetaldehyde ethyl hemiacetal (1.9 g, 10.6 mmol) in acetic acid (30 ml). The crude product was purified by chromatography on silica gel using 3% methanol in toluene as the eluent give 1 g (55%) of the desired product as a crystalline solid: mp 188–190° C. Anal. Calc'd. for $C_{19}H_{17}N_2F_3OS$ (MW 378.42): C, 60.31; H, 4.53; N, 7.40; S, 8.47. Found: C, 60.11; H, 4.39; N, 7.21; S, 8.63.

Step 4 Preparation of 4-(4-Methoxy-3-methylphenyl)-5-[4-(methylsulfonyl)phenyl]-2-(trifluoromethyl)-1H-imidazole The title compound was synthesized according to the procedure of Example 41, Step 4 using the product of Step 3 (1 g, 2.6 mmol) and Oxone®(4 g, 6.6 mmol) in methanol (20 ml), tetrahydrofuran (10 ml) and water (5 ml). The crude product was purified by chromatography on silica gel using 50% ethyl acetate in toluene as the eluent to give 610 mg (75%) of the desired product as a crystalline solid: mp 265–267° C. Anal. Calc'd. for $C_{19}H_{17}N_2F_3O_3S$ (MW 410.41): C, 55.60; H, 4.18; N, 6.83; S, 7.81. Found: C, 55.69; H, 4.28; N. 6.70; S, 8.07.

EXAMPLE 43

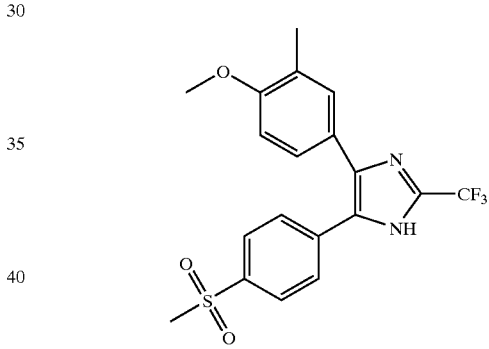

4-(4-Methoxy-3-methylphenyl)-5-[4-(methylsulfonyl)phenyl]-2-(trifluoromethyl)-1H-imidazole Step 1 Preparation of 4-Methylsulfonylphenyl-3'-methyl-4'-methoxyphenyl Benzil The sulfone was synthesized according to the procedure of Example 41, Step 4 using the benzil of Example 42, Step 2 (530 mg, 1.7 mmol) and Oxone® (2.4 g, 4 mmol) in methanol (15 ml), tetrahydrofuran (10 ml) and water (5 ml). There was isolated 545 mg (96%) of the desired sulfone as a crystalline solid: mp 149–151° C. Anal. Calc'd. for $C_{17}H_{16}O_5S$ (MW 332.39): C, 61.43; H, 4.85; S, 9.65. Found: C, 61.40; H, 4.80; S, 9.70.

Step 2 Preparation of 4-(4-Methoxy-3-methylphenyl)-5-[4-(methylsulfonyl)phenyl]-2-(trifluoromethyl)-1H-imidazole The imidazole was synthesized according to the procedure of Example 41, Step 5 using the benzil of Step 1 (540 mg, 1.6 mmol), ammonium acetate (620 mg, 8 mmol) and trifluoroacetaldehyde ethyl hemiacetal (500 mg, 3.2 mmol) in acetic acid (10 ml). There was obtained 530 mg (80%) of the desired product.

EXAMPLE 44

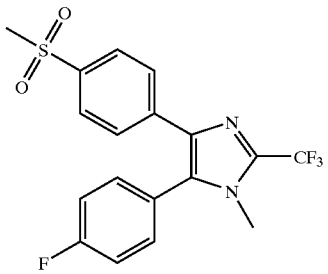

5-(4-Fluorophenyl)-1-methyl-4-[4-(methylsulfonyl)phenyl]-2-(trifluoromethyl)-1H-imidazole

EXAMPLE 45

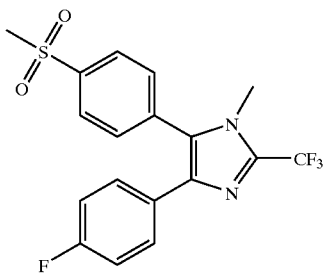

4-(4-Fluorophenyl)-1-methyl-5-[4-(methylsulfonyl)phenyl]-2-(trifluoromethyl)-1H-imidazole To a stirred suspension of hexane-washed sodium hydride (26 mg, 1.1 mmol) in dimethylformamide (10 ml) under a nitrogen atmosphere at room temperature was added a solution of 2-trifluoromethyl-5-( 4-fluorophenyl)-4-(4-methylsulfonylphenyl)-1H-imidazole (Example 1) (388 mg, 1 mmol) in dimethylformamide (10 ml). After stirring for 10 minutes, methyl iodide (142 mg, 1 mmol) was added and the reaction mixture was stirred for 16 hours. The mixture was poured into water and the solid precipitate was filtered and air dried. The crude product was purified by chromatography on silica gel using 20% ethyl acetate in toluene as the eluent to give two products: 1-methyl-2-trifluoromethyl-4-(4-methylsulfonylphenyl)-5-(4-fluorophenyl)-imidazole (210 mg, 35%), mp 187–189° C.; and 1-methyl-2-trifluoromethyl-4-(4-fluorophenyl)-5-(4-methylsulfonylphenyl)-imidazole (60 mg, 13%), mp 193–195° C. Anal. Calc'd. for $C_{18}H_{14}N_2O_2F_4S$ (MW 398.38): C, 54.27; H, 3.54; N, 7.03; S, 8.05. Found for Example 44: C, 54.11; H, 3.61; N, 6.99; S, 8.00. Found for Example 45: C, 54.21; H, 3.60; N, 6.89; S, 8.10.

EXAMPLE 46

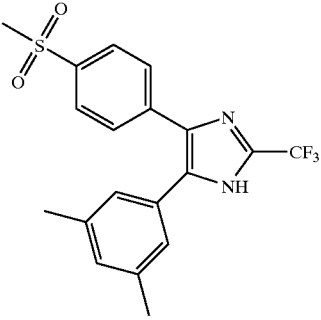

5-(3,5-Dimethylphenyl)-4-[4-(methylsulfonyl)phenyl]-2-(trifluoromethyl)-1H-imidazole Step 1 Preparation of 3,5-Dimethylbenzaldehyde To a cold (–70° C.), stirred solution of oxalyl chloride (5.12 g, 40 mmol) and dimethylsulfoxide (6.3 g, 80 mmol) in methylene chloride (50 ml) was added a solution of 3,5-dimethylbenzyl alcohol (5 g, 36.7 mmol) in methylene chloride (15 ml) over 10 minutes. After stirring for an additional 30 minutes in the cold, triethylamine (8.3 g, 82 mmol) was added and the mixture was warmed to room temperature over 1 hour. The reaction mixture was poured into water and extracted with ethyl ether. The combined organic layers were dried over sodium sulfate, filtered and concentrated to give 4.5 g (88%) of aldehyde suitable for use in the next step without further purification.

Step 2 Preparation of 4-Methylthiophenyl-3',5'-dimethylphenyl Benzoin

The benzoin was synthesized according to the procedure of Example 41, Step 2 using the product of Example 41, Step 1 (5 g, 20 mmol), 3, dimethylbenzaldehyde from Step 1 (2.7 g, 20 mmol) and 1M lithium bis(trimethylsilyl)amide in tetrahydrofuran (23 ml, 23 mmol). The crude product was purified by chromatography on silica gel using 20% ethyl acetate in hexane as the eluent to give 2.9 g (50%) of the compound as a crystalline solid: mp 81–83° C. Anal. Calc'd. for $C_{17}H_{18}O_2S$ (MW 286.40): C, 71.30; H, 6.34; S, 11.20. Found: C, 71.15; H, 6.21; S, 11.40.

Step 3 Preparation of 4-Methylthiophenyl-3',5'-dimethylphenyl Benzil

The benzil compound was synthesized according to the procedure of Example 41, Step 3 using the product of Step 2 (2.88 g, 10 mmol) and bismuth oxide (6 g, 12.5 mmol) in acetic acid (30 ml). There was obtained 2.4 g (85%) of the desired benzil as a crystalline solid: mp 100–102° C. Anal. Calc'd. for $C_{17}H_{16}O_2S$ (MW 300.39): C, 71.80; H, 5.67; S, 11.28. Found: C, 72.00; H, 5.49; S, 11.35.

Step 4 Preparation of 4-Methylsulfonylphenyl-3',5'-dimethylphenyl Benzil

The sulfone was synthesized according to the procedure of Example 41, Step 4 using the product of Step 3 (2.4 g, 8.4 mmol) and Oxone® (13.5 g, 20 mmol) in methanol (100 ml), tetrahydrofuran (50 ml) and water (50 ml). There was isolated 2.2 g (83%) of the desired sulfone as a crystalline solid: mp 141–142° C. Anal. Calc'd. for $C_{17}H_{16}O_4S$ (MW 316.40): C, 64.54; H, 5.10; S, 10.13. Found: C, 64.61; H, 5.03; S, 10.21.

Step 5 Preparation of 5-(3,5-Dimethylphenyl)-4-[4-(methylsulfonyl)phenyl]-2-(trifluoromethyl)-1H-imidazole.

The imidazole was synthesized according to the procedure of Example 41, Step 5 using the product of Step 4 (2.2 g, 6.9 mmol), ammonium acetate (2.75 g, 35 mmol) and trifluoroacetaldehyde ethyl hemiacetal (2.1 g, 14 mmol) in acetic acid (40 ml). There was obtained 1.1 g (36%) of 5-(3,5-dimethylphenyl)-4-[4-(methylsulfonyl)phenyl]-2-(trifluoromethyl)-1H-imidazole after recrystallization from ethanol: mp 255–257° C. Anal. Calc'd. for $C_{19}H_{17}N_2O_2F_3S$ (MW 394.42): C, 57.86; H, 4.34; N, 7.10; S, 8.13. Found: C, 57.46; H, 4.18; N, 7.00; S, 8.42.

EXAMPLE 47

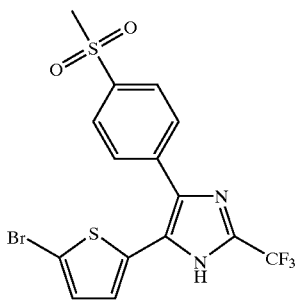

5-(5-Bromothien-2-yl)-4-[4-(methylsulfonyl) phenyl]-2-(trifluoromethyl)-1H-imidazole Step 1 Preparation of 4-Methylthiophenyl-(5-bromo-2-thiophene)Benzoin The benzoin was synthesized according to the procedure of Example 41, Step 2 using the cyanohydrin of Example Step 1 (5 g, 20 mmol), 5-bromothiophene-2-carboxaldehyde (3.82 g, 20 mmol) and 1M lithium bis(trimethylsilyl)amide in tetrahydrofuran (23 ml, 23 mmol). The crude benzoin was purified by chromatography on silica gel using 20% ethyl acetate in hexane as the eluent to give 970 mg (14%) of the desired compound as a crystalline solid: mp 115–117° C. Anal. Calc'd. for $C_{13}H_{11}BrO_2S_2$ (MW 343.26): C, 45.49; H, 3.23; S, 18.68; Br, 23.28. Found: C, 45.21; H, 3.09; S, 18.82; Br, 23.00.

Step 2 Preparation of 4-Methylthiophenyl-(5-bromo-2-thiophene)Benzil

The benzil was synthesized according to the procedure of Example 41, Step 3 using the product of Step 1 (950 mg, 2.7 mmol) and bismuth oxide (1.5 g, 3.2 mmol) in acetic acid (15 ml). There was obtained 680 mg (74%) of the desired benzil after recrystallization from methanol: mp 181–183° C. Anal. Calc'd. for $C_{13}H_9BrO_2S_2$ (MW 341.25): C, 45.76; H, 2.66; S, 18.79; Br, 23.42. Found: C, 45.46; H, 2.49; S, 18.99; Br, 23.11.

Step 3 Preparation of 4-Methylsulfonylphenyl-(5-bromo-2-thiophene)Benzil

The sulfone was synthesized according to the procedure of Example 41, Step 4 using the product of Step 2 (675 mg, 2 mmol) and Oxone® (3 g, 5 mmol) in methanol (25 ml), tetrahydrofuran (15 ml) and water (15 ml). There was isolated 553 mg (75%) of, the desired sulfone as a crystalline solid: mp 198–200° C. Anal. Calc'd. for $C_{13}H_9BrO_4S_2$ (MW 373.25): C, 41.83; H, 2.43; S, 17.18; Br, 21.41. Found: C, 41.68; H, 2.32; S, 17.40; Br, 21.20.

Step 4 Preparation of 5-(5-Bromothien-2-yl)-4-[4-(methylsulfonyl)phenyl]-2-(trifluoromethyl)-1H-imidazole The title compound was synthesized according to the procedure of Example 41, Step 5 using the product of Step 3 (550 mg, 1.5 mmol), ammonium acetate (570 mg, 7 mmol) and trifluoroacetaldehyde ethyl hemiacetal (500 mg, 3 mmol) in acetic acid (12 ml). The crude product was purified by chromatography on silica gel using 20% ethyl acetate in toluene as the eluent and recrystallization from ethyl acetate and hexane to give 190 mg (48%) of the desired product as a crystalline solid: mp 261–262° C. Anal. Calc'd. for $C_{15}H_{10}F_3BrN_2O_2S_2$ (MW 451.29): C, 39.92; H, 2.23; N, 6.21; S, 14.21. Found: C, 40.29; H, 2.25; N, 5.88; S, 14.35.

EXAMPLE 48

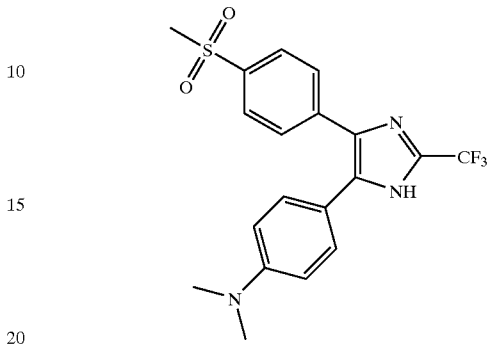

N,N-Dimethyl-4-[4-[4-(methylsulfonyl)phenyl]-2-(trifluoromethyl)-1H-imidazol-5-yl]benzenamine Step 1 Preparation of 4-Methylthiophenyl-4'-dimethylaminophenyl Benzoin The benzoin was synthesized according to the procedure of Example 41, Step 2 using the product of Example 41, Step 1 (5 g, 20 mmol), 4-dimethylaminobenzaldehyde (3 g, 20 mmol) and 1M lithium bis(trimethylsilyl)amide in tetrahydrofuran (23 ml, 23 mmol). The crude product was triturated with 10% ethyl acetate in hexane and filtered to give 1.4 g (21%) of the benzoin as a crystalline solid: mp 92–94° C. Anal. Calc'd. for $C_{17}H_{19}NO_2S$ (MW 301.41): C, 67.74; H, 6.35; N, 4.65; S, 10.64. Found: C, 67.59; H, 6.29; N, 4.38; S, 10.75.

Step 2 Preparation of 4-Methythiophenyl-4'-dimethylaminonhenyl Benzil

The benzil was synthesized according to the procedure of Example 41, Step 3 using the product of Step 1 (1.4 g, 4.6 mmol) and bismuth oxide (2.25 g, 4.9 mmol) in acetic acid (25 ml). The crude product was purified by chromatography on silica gel using 5% ethyl acetate in toluene as the eluent to give 940 mg (68%) of the desired benzil as a crystalline solid: mp 109–111° C. Anal. Calc'd. for $C_{17}H_{17}NO_2S$ (MW 299.40): C, 68.20; H, 5.72; N, 4.68; S, 10.71. Found: C, 68.10; H, 5.70; N, 4.51; S, 10.69.

Step 3 Preparation of 4-Methylsulfonylphenyl-4'-dimethylaminophenyl Benzil

The sulfone was synthesized according to the procedure of Example 41, Step 4 using the product of Step 2 (930 mg, 3.1 mmol) and Oxone® (4.3 g, 7 mmol) in methanol (40 ml), tetrahydrofuran (15 ml) and water (15 ml). There was isolated 340 mg (33%) of the desired sulfone as a crystalline solid: mp 126–129OC. Anal. Calc'd. for $C_{17}H_{17}NO_4S$ (MW 331.40): C, 61.62; H, 5.17; N, 4.23; S, 9.68. Found: C, 61.40; H, 5.07; N, 4.12; S, 9.89.

Step 4 Preparation of N,N-Dimethyl-4-[4-[4-(methylsulfonyl)-phenyl]-2-(trifluoromethyl)-1H-imidazol-5-yl]benzenamine The title compound was synthesized according to the procedure of Example 41, Step 5 using the product of Step 3 (331 mg, 1 mmol), ammonium acetate (500 mg, 6 mmol) and trifluoroacetaldehyde ethyl hemiacetal (320 mg, 2 mmol) in acetic acid (6 ml). The crude product was purified by chromatography on silica gel using 20% ethyl acetate in toluene as the eluent and recrystallization from ethyl acetate and hexane to give 65 mg (16%) of the desired product as a crystalline solid: mp 248–251° C. Anal. Calc'd. for $C_{19}H_{18}N_3O_2F_3S$ (MW 409.43): C, 55.74; H, 4.43; N, 10.26; S, 7.83. Found: C, 55.28; H, 4.33; N, 9.95; S, 7.49.

EXAMPLE 49

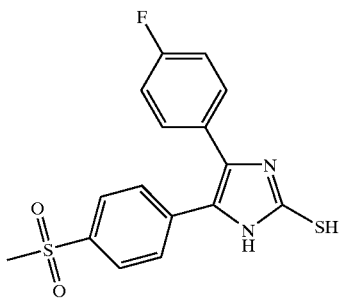

4-(4-Fluorophenyl)-5-[4-(methylsulfonyl)phenyl]-1H-imidazole-2-thiol

Step 1 Preparation of 4-Methylthiophenyl-4'-fluorophenyl Benzoin

The benzoin was synthesized according to the procedure of Example 41, Step 2 using 4-fluorobenzaldehyde trimethylsilylcyanohydrin (5 g, 21 mmol), 4-methylthiobenzaldehyde (3.62 g, 21 mmol) and 1M lithium bis(trimethylsilyl)amide in tetrahydrofuran (24 ml, 24 mmol). The crude product was purified by chromatography on silica gel using 20% ethyl acetate in hexane to give 3.8 g (67%) of the title compound as a crystalline solid: mp 95–97° C. Anal. Calc'd. for $C_{15}H_{13}O_2FS$ (MW 276.33): C, 65.20; H, 4.74; S, 11.60. Found: C, 65.09; H, 4.59; S, 11.65.

Step 2 Preparation of 4-Methylsulfonylphenyl-4'-fluorophenyl Benzoin

The sulfone was synthesized according to the procedure of Example 41, Step 4 using the product of Step 1 (1.8 g, 6.5 mmol) and Oxone® (10 g, 15 mmol) in methanol (125 ml), tetrahydrofuran (50 ml) and water (50 ml). Because of its water solubility, methylene chloride was used to extract the product from the aqueous reaction mixture. There was isolated 2.25 g (98%) of the desired benzoin as a crystalline solid: mp 106–107° C. Anal. Calc'd. for $C_{15}H_{13}OF_4S$ (MW 308.33): C, 58.43; H, 4.25; S, 10.40. Found: C, 58.22; H, 4.12; S, 10.70.

Step 3 Preparation of 4-(4-Fluorophenyl)-5-[4-(methylsulfonyl)phenyl]-1H-imidazole-2-thiol A solution of the sulfone from Step 2 (2.25 g, 7.3 mmol) and thiourea (1.05 g, 14.6 mmol) in dimethylformamide (30 ml) was heated at reflux under a nitrogen atmosphere for 3.5 hours. The reaction was cooled, poured into water (150 ml) and the precipitate filtered and air dried. Recrystallization from ethyl acetate and hexane gave 1.4 g (55%) of the desired product as a crystalline solid: mp 158–161° C. Anal. Calc'd. for $C_{16}H_{13}N_2O_2FS_2$ (MW 348.42): C, 55.16; H, 3.76; N, 8.04; S, 18.41. Found: C, 54.95; H, 3.77; N, 7.70; S, 17.98.

EXAMPLE 50

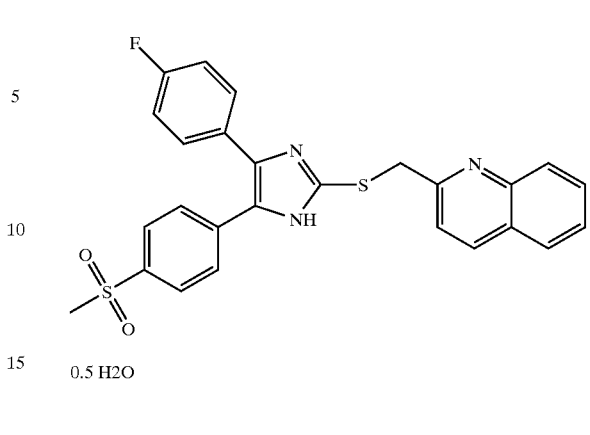

0.5 H2O

2-[[[4-(4-Fluorophenyl)-5-[4-(methylsulfonyl)phenyl]-1H-imidazol-2-yl]thio]methyl]quinoline A solution of 4-(4-fluorophenyl)-5-(4-(methylsulfonyl)phenyl]-1H-imidazole-2-thiol (Example 49) (100 mg, 0.29 mmol), 2-chloromethylquinoline hydrochloride (62 mg, 0.29 mmol) and triethylamine (60 mg, 0.58 mmol) in 2-propanol (5 ml) was heated at reflux under an argon atmosphere for 4 hours. The reaction was cooled, poured into water (25 ml) and extracted with ethyl acetate. After drying over sodium sulfate, the solvent was removed and the residue was purified by chromatography on silica gel using 50% ethyl acetate in toluene as the eluent to give 136 mg (85%) of the desired product. Although initially an oil, this material crystallized on standing: mp 179–182° C. Anal. Calc'd. for $C_{26}H_{20}N_3O_2FS_2.5H_2O$ (MW 498.60): C, 62.63; H, 4.25; N, 8.43; S, 12.86. Found: C, 62.98; H, 4.43; N, 8.03; S, 12.60.

EXAMPLE 51

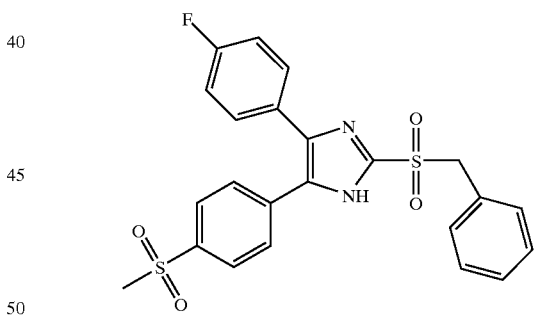

4-(4-Fluorophenyl)-5-[4-(methylsulfonyl)phenyl]-2-[(phenylmethyl)sulfonyl]-1H-imidazole Step 1 Preparation of 2-Thiobenzyl-4-(4-fluorophenyl)-5-(4-methylsulfonylphenyl)-1H-imidazole A solution of 4-(4-fluorophenyl)-5-[4-(methylsulfonyl)phenyl]-1H-imidazole-2-thiol (Example 49) (300 mg, 0.86 mmol) and benzyl bromide (150 mg, 0.87 mmol) in 2-propanol was heated at reflux for 3 hours. After cooling and removal of the solvent, the residue was stirred with 5% aqueous potassium carbonate (10 ml) and methylene chloride (15 ml). The organic layer was separated and dried over sodium sulfate. The drying agent was filtered, the filtrate concentrated in vacuo and the residue was purified by chromatography on silica gel using 25% ethyl acetate in toluene as the eluent to give 170 mg (40%) of the desired thiobenzyl compound as a glass: Anal. Calc'd. for $C_{23}H_{19}N_2O_2FS_2$ (MW 438.55): C, 62.99; H, 4.37; N. 6.39; S, 14.62. Found : C, 62.52; H, 4.19; N, 6.08; S, 14.41.

Step 2 Preparation of 4-(4-Fluorophenyl)-5-[4-(methylsulfonyl)phenyl]-2-[(phenylmethyl)sulfonyl]-1H-imidazole The title compound was synthesized according to the procedure of Example 41, Step 4 using the thiobenzyl compound of Step 1 (160 mg, 0.36 mmol) and Oxone® (350 mg, 0.43 mmol) in methanol (5 ml), tetrahydrofuran (3 ml) and water (3 ml). There was isolated 545 mg (96%) of the desired product as a crystalline solid: mp 211–213° C., after recrystallization from ethyl acetate and hexane. Anal. Calc'd. for $C_{23}H_{19}N_2O_4FS2$ (MW 470.54): C, 58.71; H, 4.07; N, 5.95; S, 13.63. Found: C, 58.43; H, 3.79; N, 5.66; S, 13.69.

EXAMPLE 52

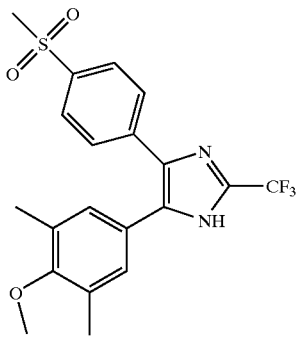

5-(3,5-Dimethyl-4-methoxyphenyl)-4-[4-(methylsulfonyl)phenyl]-2-(trifluoromethyl)-1H-imidazole Step 1 Preparation of Methyl-4-methoxy-3,5-dimnethylbenzoate A solution of 4-methoxy-3,5-dimethyl benzoic acid (10 g, 45 mmol) and sulfuric acid (5 g) in methanol (200 ml) was stirred at 25° C. for 3 days. The mixture was poured into dilute aqueous sodium bicarbonate solution and extracted with ethyl acetate. The combined organic layers were dried over sodium sulfate and concentrated to give 9 g (94%) of the desired compound which was used without further purification.

Step 2 Preparation of 4-Methoxy-3.5-dimethylbenzyl Alcohol

A mixture of ester from Step 1 (9 g, 49 mmol) and 1M lithium aluminum hydride solution in tetrahydrofuran (50 ml) in tetrahydrofuran (150 ml) was heated at reflux for 1 hour under an argon atmosphere. After cooling, the reaction was quenched by adding water (2 ml), 15% aqueous sodium hydroxide solution (2 ml) and more water (6 ml). The precipitated aluminum salts were filtered and the filtrate was evaporated to give 7.5 g (95%) of the desired compound suitable for use in the next reaction without further purification.

Step 3 Preparation of 4-Methoxy-3,5-dimethylbenzaldehyde

The aldehyde was synthesized according to the procedure of Example 46, Step 1 using the alcohol from Step 2 (7.5 g, 45 mmol), oxalyl chloride (6.35 g, 50 mmol), dimethylsulfoxide (8.8 g, 100 mmol) and triethylamine (10.2 g, 110 mmol) and in methylene chloride (100 ml). There was obtained 7 g (92%) of the desired aldehyde which was used in the next step without further purification.

Step 4 Preparation of 4-Methylthiophenyl-4'-methoxy-3',5'-dimethylphenyl benzoin The benzoin was synthesized according to the procedure of Example 41, Step 2 using the aldehyde of Step 3 (3.3 g, 20 mmol), the cyanohydrin of Example 41, Step 1 (5 g, 20 mmol) and 1M lithium bis(trimethylsilyl)amide in tetrahydrofuran (23 ml, 23 mmol). The crude compound was purified by chromatography on silica gel using 25% ethyl acetate in hexane to give 2.7 g (40%) of the benzoin as a crystalline solid: mp 121–125° C. Anal. Calc'd. for $C_{18}H_{20}O_3S$ (MW 316.42): C, 68.33; H, 6.37; S,. 10.13. Found: C, 68.00; H, 6.20; S, 10.00.

Step 5: Preparation of 4-Methylthiophenyl4'-methoxy-3',5'-dimethylphenyl Benzil

The benzil was synthesized according to the procedure of Example 41, Step 3 using the benzoin of Step 4 (1.6 g, 5 mmol) and bismuth oxide (2.9 g, 6 mmol) in acetic acid (16 ml). There was obtained 1.5 g (95%) of the desired benzil as a crystalline solid: mp 132–134° C. Anal. Calc'd. for $C_{18}H_{18}O_3S$ (MW 314.40): C, 68.76; H, 5.77; S, 10.20. Found: C, 68.70; H, 5.81; S, 10.25.

Step 6: Preparation of 4-Methylsulfonylphenyl-4'-methoxy-3',5'-dimethylphenyl Benzil The sulfone was synthesized according to the procedure of Example 41, Step 4 using the compound of Step .5 (1.5 g, 4.8 mmol) and Oxone® (7.3 g, 10.5 mmol) in methanol (50 ml), tetrahydrofuran (25 ml) and water (25 ml). There was isolated 1.1 g (70%) of the desired sulfone as a crystalline solid: mp 158–160° C. Anal. Calc'd. for $C_{18}H_{18}O_5S$ (MW 346.40): C, 62.41; H, 5.24; S,. 9.26. Found: C, 62.30; H, 5.30; S, 9.35.

Step 7: Preparation of 5-(3,5-Dimethyl-4-methoxyphenyl)-4-[4-(methylsulfonyl)phenyl]-2-(trifluoromethyl)-1H-imidazole The title compound was synthesized according to the procedure of Example 41, Step 5 using the sulfone of Step 6 (1.1 g, 3.2 mmol), ammonium acetate (1.5 g, 16 mmol) and trifluoroacetaldehyde ethyl hemiacetal (1.2 g, 6.4 mmol) in acetic acid (16 ml). The crude product was purified by chromatography on silica gel using 20% ethyl acetate in toluene as the eluent give 563 mg (44%) of the desired product as a crystalline solid: mp 265–267° C., after recrystallization from ethanol. Anal. Calc'd. for $C_{20}H_{19}N_2O_3F_3S$ (MW 424.44): C, 56.60; H, 4.51; N, 6.60; S, 7.55. Found: C, 56.75; H, 4.69; N, 6.31; S, 7.50.

EXAMPLE 53

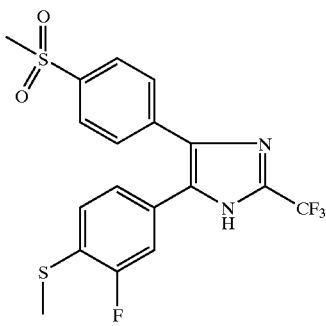

5-[3-Fluoro-4-(methylthio)phenyl]-4-[4-(methylsulfonyl)phenyl]-2-(trifluoromethyl)-1H-imidazole Step 1 Preparation of 4-Methylthio-3-fluorobenzaldehyde A solution of 3,4-difluorobenzaldehyde (2.8 g, 20 mmol) and sodium thiomethoxide (1.5 g, 20 mmol) in dimethylformamide (20 ml) was heated at 80° C. under an argon atmosphere for 2 hours. The reaction was cooled, poured into water (125 ml) and extracted with methylene chloride. The combined organic layers were dried over sodium sulfate and evaporated. The residue was distilled (bp 110–111° C., 0.5 mm Hg) to give 2.5 g (75%) of the desired aldehyde: Anal. Calc'd. for $C_8H_7FSO$ (MW 170.21): C, 56.45; H, 4.15; S, 18.84. Found: C, 56.40; H, 4.00; S, 18.90.

Step 2 Preparation of 4-Fluorophenyl-3'-fluoro-4'-methylthiophenyl Benzoin

The title compound was synthesized according to the procedure of Example 41, Step 2 using the aldehyde of Step 1 (2.5 g, 14 mmol), 4-fluorobenzaldehyde trimethylsilylcyanohydrin (3.3 g, 14 mmol) and 1M lithium bis(trimethylsilyl)amide in tetrahydrofuran (16 ml, 16 mmol). The crude benzoin was purified by chromatography on silica gel using 10% ethyl acetate in toluene to give 2.1 g (49%) of the compound as an oil. Anal. Calc'd. for $C_{15}H_{12}F_2O_2S$ (MW 294.32): C, 61.21; H, 4.11; S, 10.89. Found: C, 61.10; H, 4.15; S, 10.90.

Step 3 Preparation of 4-Fluorophenyl-3'-fluoro-4'-methylthiophenyl Benzil

The benzil was synthesized according to the procedure of Example 41, Step 3 using the benzoin of Step 2 (2.1 g, 7 mmol) and bismuth oxide (3.5 g, 8,4 mmol) in acetic acid (19 ml). There was obtained 2 g (95%) of the desired benzil as a crystalline solid: mp 92–93° C. Anal. Calc'd. for $C_{15}H_{10}F_2O_2S$ (MW 292.31): C, 61.64; H, 3.45; S, 10.97. Found: C, 61.43; H, 3.21; S, 11.05.

Step 4 Preparation of 4-Methylsulfonylphenyl-3'-fluoro-4'-methylthiophenyl Benzil A mixture of the benzil from Step 3 (2 g, 6.8 mmol) and sodium methylsulfinate (775 mg, 7.1 mmol) in dimethylformamide (10 ml) was stirred at 90° C. for 16 hours. The reaction was cooled, poured into water (120 ml) and the mixture was extracted with methylene chloride. The organic layer was dried over sodium sulfate, filtered and the filtrate concentrated. The residue was recrystallized from ethyl acetate and hexane to give 760 mg (45%) of the desired sulfone: mp 130–132° C. Anal. Calc'd. for $C_{16}H_{13}FO_4S_2$ (MW 352.41): C, 54.53; H, 3.72; S, 18.20. Found: C, 54.20; H, 3.51; S, 18.40.

Step 5 Preparation of 5-[3-Fluoro-4-(methylthio)phenyl]-4-[4-(methylsulfonyl),phenyl]-2-(trifluoromethyl)-1H-imidazole The imidazole was synthesized according to the procedure of Example 41, Step 5 using the sulfone of Step 4 (750 mg, 2.1 mmol), ammonium acetate (850 mg, 10.5 mmol) and trifluoroacetaldehyde ethyl hemiacetal (675 mg, 4.2 mmol) in acetic acid (10 ml). There was obtained 305 mg (35%) of the desired product as a crystalline solid: mp 272–274° C., after recrystallization from ethyl acetate. Anal. Calc'd. for $C_{18}H_{14}N_2F_4)O_2S_2$ (MW 430.44): C, 50.23; H, 3.28; N, 6.51; S, 14.90. Found: C, 50.41; H, 3.32; N, 6.21; S, 14.80.

EXAMPLE 54

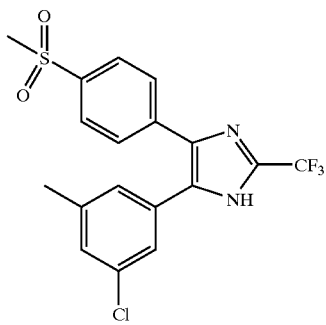

5-(3-Chloro-5-methylphenyl)-4-[-(methylsulfonyl)phenyl]-2-(trifluoromethyl)-1H-imidazole Step 1 Preparation of 4-Fluorophenyl-3'-methyl-5'-chlorophenyl Benzoin The benzoin was synthesized according to the procedure of Example 41, Step 2 using 4-fluorobenzaldehyde trimethylsilylcyanohydrin (4 g, 18 mmol), 3-methyl-5-chlorobenzaldehyde (2.78 g, 18 mmol) and 1M lithium bis(trimethylsilyl)amide in tetrahydrofuran (20 ml, 20 mmol). The crude compound was purified by chromatography on silica gel using 5% ethyl acetate in toluene as the eluent to give 1.85 g (37%) of the benzoin as a crystalline solid: mp 101–103° C. Anal. Calc'd. for $C_{15}H_{12}FClO_2$ (MW 278.71): C, 64.64; H, 4.34. Found: C, 64.51; H, 4.29.

Step 2 Preparation of 4-Fluorophenyl-3'-methyl-5'-chlorophenyl Benzil

The benzil was synthesized according to the procedure of Example 41, Step 3 using the benzoin of Step 1 (1.85 g, 6.6 mmol) and bismuth oxide (3.3 g, 7.3 mmol) in acetic acid (15 ml). There was obtained 1.6 g (90%) of the desired benzil as a crystalline solid: mp 115–116° C. Anal. Calc'd. for $C_{15}H_{10}FClO_2$ (MW 276.70): C, 65.11; H, 3.64. Found: C, 65.00; H, 3.48.

Step 3 Preparation of 4-Methylsulfonylphenyl-3'-methyl-5'-chlorophenyl Benzil

Following the procedure of Example 53, Step 4 and using the product from Step 2 (1.5 g, 5.4 mmol) and sodium methylsulfinate (665 mg, 6.5 mmol) in dimethylformamide (15 ml), there was obtained 1.4 g (75%) of the desired benzil sulfone: mp 145–147° C., after recrystallization from ethyl acetate and hexane. Anal. Calc'd. for $C_{16}H_{13}ClO_4S$ (MW 336.80): C, 57.06; H, 3.89; S, 9.52. Found: C, 56.98; H, 3.71; S, 9.62.

Step 4 Preparation of 5-(3-Chloro-5-methylphenyl)-4-[4-(methylsulfonyl)phenyl]-2-(trifluoromethyl)-1H-imidazole The title compound was synthesized according to the procedure of Example 41, Step 5 using the benzil sulfone of Step 3 (1 g, 3 mmol), ammonium acetate (1.25 g, 15 mmol) and trifluoroacetaldehyde ethyl hemiacetal (875 mg, 6 mmol) in acetic acid (15 ml). There was obtained 480 mg (45%) of the desired product as a crystalline solid: mp 260–262° C., after recrystallization from ethyl acetate and hexane. Anal. Calc'd. for $C_{18}H_{14}N_2O_2F_3ClS$ (MW 414.84.): C, 52.12; H, 3.40; N, 6.75; S, 7.73. Found: C, 52.47, H, 3.31; N. 6.52; S, 7.57.

EXAMPLE 55

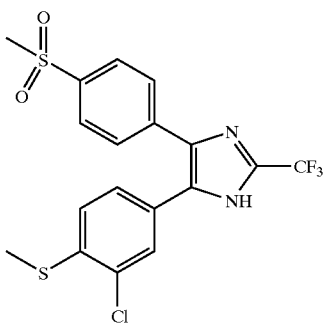

5-[3-Chloro-4-(methylthio)phenyl]-4-[4-(methylsulfonyl)phenyl]-2-(trifluoromethyl)-1H-imidazole Step 1 Preparation of 3-Chloro-4-methylthiobenzaldehyde The aldehyde was synthesize d according to the procedure of Example 53, step 1 using 4-fluoro-3-chlorobenzaldehyde (2.3 g, 14 mmol) and sodium methyl mercaptide (1.08 g, 15 mmol) in dimethylformamide (10 ml). There was obtained 1.58 g (60%) of the desired aldehyde as a crystalline solid: mp 59–61° C., after chromatography on silica gel using 5% ethyl acetate in hexane as the eluent. Anal. Calc'd. for $C_8H_7ClOS$ (MW 186.66): C, 51.48; H, 3.78; S, 17.18. Found: C, 51.29; H, 3.52; S, 17.10.

Step 2 Preparation of 4-Fluorophenyl-3'-chloro-4'-methylthiophenyl Benzoin

The benzoin was synthesized according to the procedure of Example 41, Step 2 using the compound of Step 1 (1.5 g, 8 mmol), 4-fluorobenzaldehyde trimethylsilylcyanohydrin (1.78 g, 8 mmol) and 1M lithium bis(trimethylsilyl)amide in tetrahydrofuran (9 ml, 9 mmol). The crude compound was purified by chromatography on silica gel using 10% ethyl acetate in toluene to give 1.5 g (61%) of the benzoin as a crystalline solid: mp 96–98° C. Anal. Calc'd. for $C_{15}H_{12}O_2FClS$ (MW 310.78): C, 57.97; H, 3.89; S, 10.32. Found: C, 58.04; H, 3.80; S, 10.47.

Step 3 Preparation of 4-Fluorophenyl-3'-chloro-4'-methylthiophenyl Benzil

The benzil was synthesized according to the procedure of Example 41, Step 3 using the benzoin of Step 2 (1.5 g, 4.8 mmol) and bismuth oxide (2.65 g, 5.3 mmol) in acetic acid (15 ml). There was obtained 1.45 g (98%) of the desired benzil as a crystalline solid: mp 124–126° C. Anal. Calc'd. for $C_{15}H_{10}O_2FClS$ (MW 308.77): C, 58.35; H, 3.26; S, 10.38. Found: C, 58.18; H, 3.09; S, 10.55.

Step 4 Preparation of 4-Methylsulfonylphenyl-3'-chloro-4'-thiomethylphenyl Benzil Following the procedure of Example 53, Step 4 using the benzil of Step 3 (1.5 g, 4.9 mmoles) and sodium methylsulfinate (620 mg, 5.5 mmol) in dimethylformamide (15 ml), there was obtained 450 mg, (25%) of the desired sulfone: mp 138–139° C., after recrystallization from ethyl acetate. Anal. Calc'd. for $C_{16}H_{13}O_4ClS_2$ (MW 368.86): C, 52.10; H, 3.55; S, 17.39. Found: C, 51:93; H, 3.31; S, 17.52.

Step 5: Preparation of 5-[3-Chloro-4-(methylthio)phenyl]-4-[4-(methylsulfonyl)phenyl]-2-(trifluoromethyl)-1H-imidazole The title compound was synthesized according to the procedure of Example 41, Step 5 using the sulfone of Step 4 (440 mg, 1.2 mmol), ammonium acetate (560 mg, 7.2 mmol) and trifluoroacetaldehyde ethyl hemiacetal (390 mg, 2.4 mmol) in acetic acid (7 ml). The crude product was purified by recrystallization from ethyl acetate and hexane to give 283 mg (53%) of the title compound as a crystalline solid: mp 255–257C. Anal. Calc'd. for $C18H_{14}N_2O_2F_3ClS_2$ (MW 446.90): C,48.38; H, 3.16; N, 6.27; S, 14.35. Found: C, 48.54; H, 3.15; N, 5.89; S. 14.57.

EXAMPLE 56

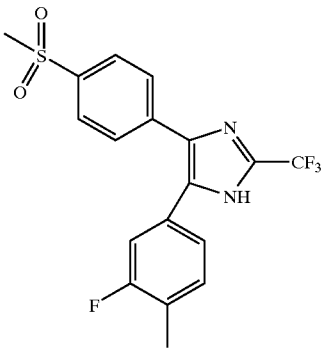

5-(3-Fluoro-4-methylphenyl)-4-[4-(methylsulfonyl)phenyl]-2-(trifluoromethyl)-1H-imidazole Step 1 Preparation of 3-Fluoro-4-methylbenzaldehyde tert-Butyllithium (31 ml of a 1.7 M solution in toluene, 52 mmol) was added slowly over 30 minutes to a cold (−70° C.), stirred solution of 4-bromo-2-fluorotoluene (5 g, 26 mmol) in tetrahydrofuran (25 ml). After addition was complete, the mixture was stirred for 15 minutes and a solution of dimethylformamide (2 g, 28 mmol) in tetrahydrofuran (10 ml) was then added over 10 minutes. After addition was complete, the reaction solution was warmed to room temperature over 30 minutes. The reaction was poured into 0.5N aqueous potassium bisulfate (125 ml) and extracted with ethyl ether. The combined organic extracts were dried over sodium sulfate and evaporated to give 3.3 g (90%) of the desired product as an oil. This material was suitable for use without further purification.

Step 2 Preparation of 4-Fluorophenyl-3-fluoro-4'-methylphenyl Benzoin

The benzoin was synthesized according to the procedure of Example 41, Step 2 using the product of Step 1 (3.3 g, 24 mmol), 4-fluorobenzaldehyde trimethylsilylcyanohydrin (5.3 g 24 mmol) and 1M lithium bis(trimethylsilyl)amide in tetrahydrofuran (25 ml, 25 mmol). The crude compound was purified by chromatography on silica gel using 10% ethyl acetate in toluene as the eluent to give 2.4 g (48%) of the title benzoin as a crystalline solid: mp 69–72° C. Anal. Calc'd. for $C_{15}H_{12}F_2O_2$ (MW 262.25): C, 68.70; H, 4.61. Found: C, 68.53; H, 4.49.

Step 3 Preparation of 4-Fluorophenyl-3'-fluoro-4'-methylphenyl Benzil

The benzil compound was synthesized according to the procedure of Example 41, Step 3 using the product of Step 2 (2.4 g, 9 mmol) and bismuth oxide (5 g, 12 mmol) in acetic acid (25 ml). There was obtained 2.3 g (95%) of the desired benzil as a crystalline solid: mp 81–82° C. Anal. Calc'd. for $C_{15}H_{10}F_2O_2$ (MW 260.24): C, 69.23; H, 3.87. Found: C, 69.04; H, 3.80.

Step 4 Preparation of 4-Methylsulfonylphenyl-3'-fluoro-4'-methylphenyl Benzil

Following the procedure of Example 53, Step 4 using the benzil from Step 3 (2.15 g 8.2 mmol) and sodium methylsulfinate (1.05 g, 10 mmol) in dimethylformamide (20 ml), there was obtained 1 g (50%) of the desired sulfone: mp 146–147° C., after recrystallization from ethyl acetate and hexane. Anal. Calc'd. for $C_{16}H_{13}FO_4S$ (MW 320.34): C, 59.99; H, 4.09; S, 10.01. Found: C, 59.68; H, 4.17; S, 10.13.
Step 5 Preparation of 5-(3-Fluoro-4-methylphenyl)-4-[4-(methylsulfonyl)phenyl]-2-(trifluoromethyl)-1H-imidazole The title compound was synthesized according to the procedure of Example 41, Step 5 using the product of Step 4 (355 mg, 1.1 mmol), ammonium acetate (510 mg, 6.6 mmol) and trifluoroacetaldehyde ethyl hemiacetal (360 mg, 2.2 mmol) in acetic acid (5 ml). The crude product was purified by recrystallization from ethyl acetate and hexane to give 140 mg (40%) of the title compound: mp 251–252° C. Anal. Calc'd. for $C_{18}H_{14}N_2F_4O_2S$ (MW 398.38): C, 54.27; H, 3.54; N, 7.03; S, 8.05. Found: C, 53.98; H, 3.40; N, 6.72; S, 7.84.

EXAMPLE 57

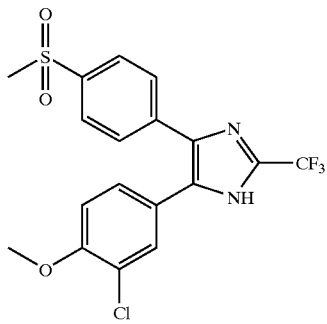

5-(3-Chloro-4-methoxyphenyl)-4-[4-(methylsulfonyl)phenyl]-2-(trifluoromethyl)-1H-imidazole Step 1 Preparation of 4-Fluorophenyl-3'-chloro-4'-methoxyphenyl Benzoin The benzoin compound was synthesized according to the procedure of Example 41, Step 2 using 4-fluorobenzaldehyde trimethylsilylcyanohydrin (5.3 g, 24 mmol), 3-chloro-4-methoxybenzaldehyde (4.1 g, 24 mmol) and 1M lithium bis(trimethylsilyl)amide in tetrahydrofuran (25 ml, 25 mmol). The crude compound was purified by chromatography on silica gel using 10% ethyl acetate in toluene as the eluent to give 3.5 g (51%) of the title benzoin as a crystalline solid: mp 119–121° C. Anal. Calc'd. for $C_{15}H_{12}ClFO_3$ (MW 294.71): C, 61.13; H, 4.10. Found: C, 61.00; H, 4.21.
Step 2 Preparation of 4-Fluorophenyl-3'-chloro-4'-methoxyphenyl Benzil The benzil compound was synthesized according to the procedure of Example 41, Step 3 using the product of Step 1 (3.5 g, 12 mmol) and bismuth oxide (6.6 g, 14 mmol) in acetic acid (35 ml). There was obtained 2.8 g (85%) of the desired benzil as a-crystalline solid: mp 152–154° C. Anal. Calc'd. for $C_{15}H_{10}FClO_3$ (MW .292.70): C, 61.55; H, 3.44. Found: C, 61.40; H, 3.31.
Step 3 Preparation of 4-Methylsulfonylphenyl-3'-chloro-4'-methoxyphenyl Benzil Following the procedure of Example 53, Step 4 using the benzil from Step 2 (2.8 g, 9.6 mmol) and sodium methylsulfinate (1.25 g, 12 mmol) in dimethylformamide (25 ml), there was obtained 2.3 g (70%) of the desired product: mp 163–166° C. Anal. Calc'd. for $C16H_{13}ClO_5S$ (MW 352.79): C, 54.47; H, 3.71; S, 9.09. Found: C, 54.11; H, 3.52; S, 9.30.
Step 4: Preparation of 5-(3-Chloro-4-methoxyphenyl)-4-[4-(methylsulfonyl)phenyl]-2-(trifluoromethyl)-1H-imidazole The title compound was synthesized according to the procedure of Example 41, Step 5 using the sulfone of Step 3 (2.2 g, 6.5 mmol), ammonium acetate (3 g, 20 mmol) and trifluoroacetaldehyde ethyl hemiacetal (2.1 g, 13 mmol) in acetic acid (30 ml). The crude product was purified by chromatography on silica gel using 25% ethyl acetate in toluene as the eluent give 760 mg (35%) of the desired product as a crystalline solid: mp 288–291° C., after recrystallization from ethyl acetate and hexane. Anal. Calc'd. for $C_{18}H_{14}F_3ClN_2O_3S$ (MW 430.83): C, 50.16; H, 3.28; N, 6.50; S, 7.44. Found: C, 50.17; H, 3.17; N, 6.31; S, 7.58.

EXAMPLE 58

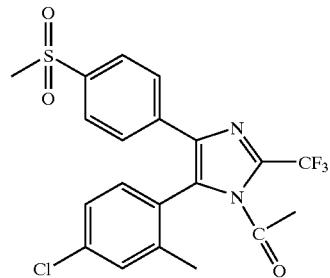

1-[5-(3-Chloro-5-methylphenyl)-4-[4-(methylsulfonyl)phenyl]-2-(trifluoromethyl)-1H-imidazol-1-yl]ethanone Acetyl chloride (50 mg, 0.6 mmol) was added to a cold (5° C.), stirred solution of Example 54 (150 mg, 0.3 mmol) and triethylamine (80 mg, 0.8 mmol) in acetonitrile (3 ml). The reaction was warmed to room temperature and stirred for 4 hours. The solvent was removed and the residue was purified by chromatography on silica gel using 20% ethyl acetate in toluene as the eluent to give 15 mg of the desired product as a crystalline solid: mp 257° C. Anal. Calc'd. for $C_{20}H_{16}N_2O_3ClF_3S$ (MW 456.87): C, 52.58; H, 3.53; N, 6.13; S, 7.02. Found: C, 52.21; H, 3.61; N, 5.95; S, 7.30.

EXAMPLE 59

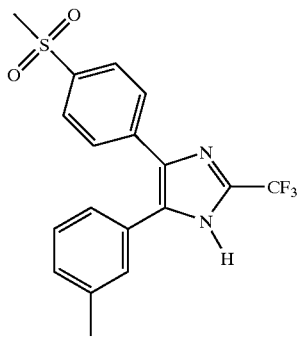

5-(3-Methylphenyl)-4-[4-(methylsulfonyl)phenyl]-2-trifluoromethyl-1H-imidazole

Step 1 Preparation of 3-Methyl-α-[(trimethylsilyl)oxy]benzeneacetonitrile

The silyl compound was prepared by allowing trimethylsilylcyanide (52 mmol, 7 ml) and m-tolualdehyde (50 mmol, 5.88 ml) to stir at room temperature in the presence of zinc(II) iodide (50 mg) for 3 hours. The compound (10.6 g, 96%) was obtained as an oil by distilling the reaction mixture in vacuo: bp 89° C., ca. 1 torr).

Step 2 Preparation of 2-Hydroxy-1-(3-methylphenyl)-2-[4-(methylthio)phenyl]-ethanone Dry tetrahydrofuran (100 ml) was introduced to a dry round-bottom flask, and cooled to −78%C. Lithium hexamethyldisilazide (1M in THF, 50 ml) was added, followed by the silyl compound from step 1 (48 mmol, 10.6 g), rinsing with ca. 10 ml additional THF to ensure complete transfer. After 30 minutes, (4-methylthio)benzaldehyde (50 mmol, 6.67 ml), was added. After 1 hour the reaction was quenched with 10% HCl (200 ml) and $KHF_2$ (60 mmol, 4.68 g). The resulting mixture was stirred at ambient temperature for 1 hour, then extracted using ethyl acetate (400 ml). The organic phase was separated and washed with sat. NaCl (60 ml). The organic phase was dried over magnesium sulfate, filtered, concentrated, and subjected to silica gel chromatography (2:1 hexanes: ethyl acetate), affording the title material (8.31 g, 62%) as a waxy semisolid, which was used in the next step.

Step 3 Preparation of 1-(3-Methylphenyl)-2-[4-(methylthio)phenyl]ethane-1,2-dione The ketone from step 2 (30.5 mmol, 8.31 g) was diluted with acetic acid (90 ml) and heated to ~90° C. $Bi_2O_3$ (30.5 mmol, 14.2 g) was added. After stirring 15 minutes, additional bismuth oxide (15 mmol, 7 g) was added. After 30 additional minutes, the mixture was filtered through silica and Celite®, then lyophilized. The residue was subjected to chromatography (3:1 hexane: ethyl acetate), affording the title compound as a yellow solid (3.56 g, 43%), which was used in the next step.

Step 4 Preparation of 5-(3-Methylphenyl)-4-[4-(methylthio)phenyl]-2-(trifluoromethyl)-1H-imidazole The dione from step 3 (13 mmol, 3.51 g) was combined with acetic acid (40 ml), ammonium acetate (78 mmol, 6.01 g) and ethyl trifluoroacetaldehyde hemiacetal (39 mmol, 4.53 ml). The mixture was stirred at reflux for 1 hour. Additional hemiacetal (ca 13 mmol, 1.5 ml) was added and heating was continued for another hour. The mixture was cooled, lyophilized, and subjected to chromatography (5% methanol in toluene), affording the product as a thick semi-solid (2.35 g, 54%) which was carried through the next step.

Step 5 Preparation of 5-(3-Methylphenyl)-4-[4-(methylsulfonyl)phenyl]-2-(trifluoromethyl)-1H-imidazole Acetic acid (30 ml) was added to the imidazole from step 4 (6.95 mmol, 2.35 g), followed by 30% hydrogen peroxide (~24 mmol, 2.4 ml). The mixture was heated for thirty minutes over a steam bath, cooled, lyophilized, and then purified by chromatography (ethyl acetate). Final purification was accomplished by recrystallization from acetonitrile, affording the title compound (0.60 g, 24%): Anal. Calc'd. for $C_{18}H_{15}F_3N_2O_2S$: C, 56.84; H, 3.97; N, 7.36. Found: C, 56.80; H, 4.09; N, 7.29.

EXAMPLE 60

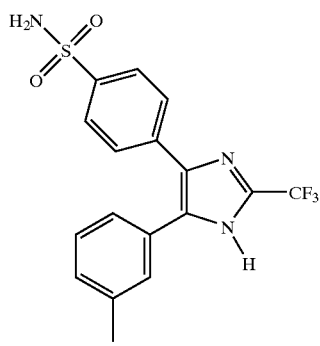

5-(3-Methylphenyl)-4-[4-(sulfonamido)phenyl]-2-trifluoromethyl-1H-imidazole

Step 1 Preparation of 5-(3-Methylphenyl)-4-[4-(methylsulfonyl)phenyl]-2-(trifluoromethyl)-1-[(2-trimethylsilylethoxy)methyl]-1H-imidazole Sodium hydride (60% in oil, 1.06 mmol, 42 mg) was washed with hexane (ca 2×1 ml), then covered with N,N-dimethyformamide (2.1 ml). 5-(3-Methylphenyl)-4-[4-(methylsulfonyl)phenyl]-2-trifluoromethyl-1H-imidazole (Example 59) (0.70 mmol, 268 mg) was added, with stirring. After 15 minutes, 2-(trimethylsilyl)ethoxymethyl chloride (SEM-Cl) (1.06 mmol, 0.19 ml) was added and the mixture was stirred overnight. The reaction was quenched with saturated ammonium chloride (ca. 4 drops), and concentrated in vacuo. The residue was subjected to chromatography (2:1 hexane: ethyl acetate) and concentrated to afford the title compound (284 mg, 79%) as an oil as a mixture of the two possible N alkylated isomers (by NMR).

Step 2 Preparation of 5-(3-Methylphenyl)-4-[4-(sulfonamido)phenyl]-2-trifluoromethyl-1H-imidazole The compound of step 1 (1.0 mmol, 510 mg) was diluted with tetrahydrofuran (3 ml) and cooled to 0° C. n-Butylmagnesium chloride (2.0 M in THF, 2.5 ml) was added over 1 minute. After 5 minutes, the cold bath was removed and the reaction mixture was warmed the ref lux. The solution was cooled to 0° C. after 40 hours at reflux, and a solution of hydroxylamine O-sulphonic acid (0.9 g) and sodium hydroxide (0.9 g) in water (4 ml) was added. The reaction mixture was stirred for 7 hours at ambient temperature, and extracted into ethyl acetate (50 ml). The organic phase was dried over magnesium sulphate, filtered through a silica plug, and concentrated. The residue was diluted with ethanol (8 ml) and 6N HCl (2 ml). After 90 minutes, a solution of ammonium hydroxide (0.5 ml) in water (5 ml) was added, and the mixture was taken up with ethyl acetate (100 ml). The organic phase was separated, dried using magnesium sulphate, concentrated, and subjected to chromatography (2:1 hexane: ethyl acetate). The product was re-concentrated from acetone to afford the title compound as a white powder (173 mg, 45%): Anal. Calc'd. for $C_{17}H_{14}F_3N_3O_2S.(1/2$ acetone): C, 54.14; H, 4.18; N, 10.24. Found: C, 54.06; H, 4.23; N, 9.86.

EXAMPLE 61

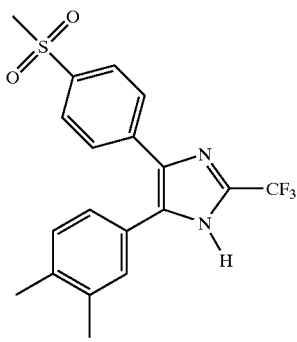

5-(3,4-Dimethylphenyl)-4-[4-(methylthio)phenyl]-2-(trifluoromethyl)-1H-imidazole Step 1 Preparation of 3,4-Dimethyl-α-[(trimethylsilyl)oxy]benzeneacetonitrile The title compound was prepared by the method of Example 59, step 1, using (41 mmol, 5.5 g) of 3,4-dimethylbenzaldehyde and affording the title compound as an oil (8.51 g, 98%)(bp$_{\sim 1torr}$=105° C.).

Step 2 Preparation of 1-(3,4-Dimethylphenyl)-2-hydroxy-2-[4-(methylthio)phenyl]-ethanone The title compound was prepared by the method of Example 59, step 2, using (40.9 mmol, 8.50 g) of 3,4-dimethyl-α-[(trimethylsilyl)oxy]benzeneacetonitrile from Step 1, and affording (9.7 g, 83%) of the title compound as an oil.

Step 3 Preparation of 1-(3,4-Dimethylphenyl)-2-[4-(methylthio)phenyl]ethane-1,2-dione The title compound was prepared from 1-(3,4-dimethylphenyl)-2-hydroxy-2-[4-(methylthio)phenyl]-ethanone from step 2 (34 mmol, 9.7 g)) by the method of Example 59, step 3. The title compound (4.65 g, 50%), a yellow solid, was used directly in the next step.

Step 4 Preparation-of 5-(3,4-Dimethylphenyl)-4-[4-(methylthio)phenyl]-2-(trifluoromethyl)-1H-imidazole The title compound was obtained by the method of Example 59, step 4, using 1-(3,4-dimethylphenyl)-2-[4-(methylthio)phenyl]ethane-1,2-dione from step 3 (16 mmol, 4.5 g). The product was a viscous oil (2.3 g, 41%).

Step 5 Preparation of 5-(3,4-Dimethylphenyl)-4-[4-(methylsulfonyl)phenyl]-2-(trifluoromethyl)-1H-imidazole The title compound was obtained from 5-(3,4-dimethylphenyl)-4-[4-(methylthio)phenyl]-2-(trifluoromethyl)-1H-imidazole (Step 4) (6.6 mmol, 2.3 g) by the method of Example 59, step 5. This analog was recrystallized first from 2-butanone, and then acetone, and finally dried by concentration from acetonitrile, affording the desired product (150 mg, 6%). mp (DSC) 279–284° C. Anal. Calc'd. for $C_{19}H_{17}F_3N_2O_2S \cdot 1/3\ H_2O$: C, 56.99; H, 4.45; N, 7.00. Found: C, 56.95; H, 4.08; N, 7.00.

EXAMPLE 62

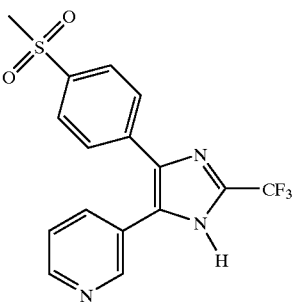

4-(4-(Methylsulfonyl)phenyl]-5-(3-pyridyl)-2-(trifluoromethyl)-1H-imidazole

Step 1 Preparation of 4-Methylthio-α-[(trimethylsilyl)oxy]benzeneacetonitrile

To a mixture of KCN (50 mg) and trimethysilylcyanide (55 mmol, 7.31 ml) was added 4-methylthiobenzaldehyde (50 mmol, 6.66 ml). The reaction was stirred at ambient temperature 4 hours, then subjected to distillation (bp$_{\sim 1torr}$=131° C.), affording the product as an oil (9.7 g, 77%).

Step 2: Preparation of 2-Hydroxy-1-[4-(methylthio)phenyl]-2-(3-pyridyl)-ethanone 4-Methylthio-α-[(trimethylsilyl)oxy]benzeneacetonitrile (39 mmol, 9.70 g was added to a solution of lithium hexamethydisilazide (1M in THF, 42 ml) in dry tetrahydrofuran (42 ml) at −78° C. After 15 minutes, 3-pyridinecarboxaldehyde (39 mmol, 4.13 ml) was added. The reaction was quenched after an additional 30 minutes using 10% HCl (150 ml), followed by KHF$_2$ (4.0 g). The mixture was warmed to ambient temperature and basified to ca. pH 14, using 50% NaOH, The product was extracted into ethyl acetate (200 ml, then 2×100 ml). The combined organic layers were dried using magnesium sulfate, filtered, concentrated, and subjected to chromatography (2:1 hexane:ethyl acetate), affording the title compound as a solid (6.3 g, 61%), which was used in the next step.

Step 3: Preparation of 1-(4-[Methylthio)phenyl]-2-(3-pyridyl)-ethane-1,2-dione

A solution of dimethylsulphoxide (30 mmol, 2.13 ml) in methylene chloride (90 ml) was cooled to −65° C. Trifluoroacetic acid anhydride (20 mmol, 2.82 ml) was added over 3 minutes, then stirred 10 minutes. 2-Hydroxy-1-[4-(methylthio)phenyl]-2-(3-pyridyl)-ethanone (step 2) (10 mmol, 2.59 g) was suspended in ca 10 ml of methylene chloride and rinsed into the reaction vessel using ca 5 ml additional solvent. After 40 minutes, triethylamine (58 mmol, 8.07 ml) was added. The mixture was warmed to 0° C. over 30 minutes, with continued stirring, then-diluted with water (100 ml) and extracted with ethyl acetate (200, then 2×50 ml). The combined organic layers were dried over magnesium sulfate, filtered, concentrated, and subjected to chromatography (2:1 hexane:ethyl acetate), affording the title compound as a yellow solid (2.43 g, 94%), which was used in the next step.

Step 4 Preparation of 4-[4-(Methylthio)phenyl]-5-(3-pyridyl)-2-(trifluoromethyl)-1H-imidazole The title compound was synthesized from 1-[4-(methylthio)phenyl]-2-(3-pyridyl)-ethane-1,2-dione (Step 3) by the method of Example 59, step 4, except that after lyophilization, the residue was diluted with ethyl acetate (200 ml) and washed with 10% ammonium hydroxide (100 ml). The aqueous layer was extracted with ethyl acetate (2×50 ml), and the combined organic layers were dried over magnesium sulfate, filtered, concentrated, and subjected to chromatography, affording the product as a viscous oil (3.13 g, ~quant.), which was used in the next step.
Step 5: Preparation of 4-[4-(Methylsulfonyl)phenyl]-5-(3-pyridyl)-2-(trifluoromethyl)-1H-imidazole 4-[4-(Methylthio)phenyl]-5-(3-pyridyl)-2-(trifluoromethyl)-1H-imidazole (Step 4) (9.3 mmol, 3.13 g) was diluted with acetic acid (20 ml), treated with hydrogen peroxide (30%, ~19 mmol, 1.9 ml), and heated over a steam bath for 30 minutes. After subsequent lyophilization, the residue was treated with amberlyst (OH-) resin and washed onto a chromatography column, where the product was eluted using 90:10:1 ethyl acetate:methanol:ammomium hydroxide. The concentrated product was recrystallized twice from ethyl acetate/hexane, and concentrated from acetone solution to remove final traces of water and solvent. The structure of the product (640 mg, 22%) was verified spectroscopically. Anal. Calc'd. for $C_{16}H_{12}F_3N_3O_2S$: C, 52.31; H, 3.29; N, 11.44. Found:. C, 52.74; H, 3.48; N, 10.22.

EXAMPLE 63

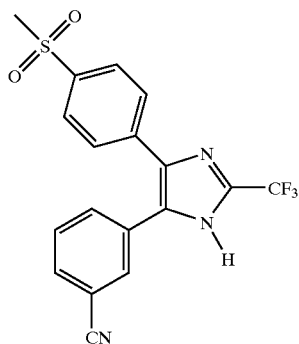

5-(3-Cyanophenyl)-4-[4-(methylthio)phenyl]-2-(trifluoromethyl)-1H-imidazole

Step 1 Preparation of 1-[3-Cyanophenyl)-2-hydroxy-2-[4-(methylthio)phenyl]-ethanone Sodium cyanide (3 mmol, 0.147 g) was added to a mixture of ethanol (30 ml), water (30 ml), 3-cyanobenzaldehyde (30 mmol, 3.93 g) and 4-(methylthio)benzaldehyde (30 mmol, 4.0 ml). The reaction was stirred at reflux 30 minutes, diluted with water (20 ml) and extracted with ethyl acetate (250 ml). The organic layer was separated, dried over magnesium sulfate, concentrated, and the residue purified by silica gel chromatography (2:1 hexane:ethyl acetate), affording the title compound as a solid (5.2, 61%).

Step 2 Preparation of 1-(3-Cyanophenyl)-2-(4-(methylthio)phenyl]ethane-1,2-dione The ketone from step 1 (7.07 mmol, 2.00 g) was transformed into the title dione using a Swern. oxidation similar to Example 62, step 3. The title compound (2.0 g, ~quant), a yellow solid, was used in the next step.

Step 4: Preparation of 5-(3-Cyanophenyl)-4-[4-(methylthio),phenyl]-2-(trifluoromethyl)-1H-imidazole 1-(3-Cyanophenyl)-2-[4-(methylthio) phenyl]ethane-1,2-dione (Step 3) (7.00 mmol, 1.97 g) was converted into the title compound using the method of Example 59, step 4, affording a foam (1.79 g, 71%).

Step 5: Preoparation of 5-(3-Cyanophenyl)-4-[4-(methylsulfonyl)phenyl]-2-(trifluoromethyl)-1H-imidazole 5-(3-cyanophenyl)-4-[4-(methylthio)phenyl]-2-(trifluoromethyl)-1H-imidazole (Step 4) (1.4 mmol, 502 mg) was oxidized using the method of Example 59, step 5. The chromatographed product was recrystallized from ethyl acetate/hexane, then dried by concentration from acetonitrile, affording 132 mg (25%). Anal. Calc'd. for $C_{18}H_{12}F_3N_3O_2S$: C, 55.24; H, 3.09; N, 10.74. Found: C, 55.25; H, 3.11; N, 10.74.

EXAMPLE 64

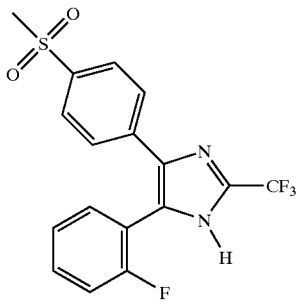

5-(2-Fluorophenyl)-4-[4-(methylsulfonyl)phenyl]-2-(trifluoromethyl)-1H-imidazole Step 1 Preparation (2-Fluorophenyl) methyl-triphenylphosphonium Bromide 2-Fluorobenzyl bromide (80 mmol, 12.4 ml) was added to a solution of triphenylphosphine (80 mmol, 21.0 g) and tetrabutylammonium iodide (100 mg) in toluene (60 ml). The mixture was stirred at ambient temperature 24 hours, then heated at reflux for 15 minutes. On cooling, the title compound was isolated by filtration, dried in vacuo to constant weight (34 g, 94%) and used without characterization.

Step 2 Preparation of 1-Fluoro-2-[2-[4-(methylsulfonyl) phenyl]ethylenyl]benzene The phosphonium salt from step 1 (20 mmol, 9.02 g) was suspended in ethanol (60 ml) and cooled to 0° C. n-Butyllithium (1.6 M in hexane, 13.1 ml) was added slowly (over ~15 minutes). Five minutes after complete addition, (4-methylthio)benzaldehyde (20 mmol, 2.67 ml) was added, and the mixture was stirred 2.5 hours at ambient temperature. Water (40 ml) was added, and the product was extracted into methylene chloride (200 ml). The organic phase was dried over magnesium sulfate, passed through a large silica plug, and concentrated, affording a solid material, which was diluted with methanol (80 ml) and cooled to 0° C. Oxone® (50 mmol, 30.8 g) in aqueous (150 ml) suspension was added, the reaction was stirred at 0° C. for 15 minutes, then 1.5 hours at ambient temperature. The product was extracted into methylene chloride (200 ml, then 2×50 ml). The combined organic phases were dried (MgSO$_4$), filtered through a silica plug, and concentrated to afford the title compound (3.5 g, 63%) as a semi-solid mixture (~2:1) of olefin isomers. The material was used, as is, in the next transformation.

Step 3 Preparation of 1-(2-Fluorophenyl)-2-[4-(methylsulfonyl)phenyl]ethane-1,2-dione Based on a procedure by: K. B. Sharpless,et al. [J. Am. Chem. Soc., 93, 3303 (1971)] the stilbene from step 2 (12.5 mmol, 3.45 g) was dissolved in acetic anhydride (60 ml) and cooled to 0° C. Solid KMnO$_4$ (50 mmol, 7.90 g) was added in 5 portions over a 20 minute period. After an additional hour, the reaction was quenched as follows: toluene (200 ml, chilled to 0° C.) was added; then sodium bisulfite (14 g/60 ml, chilled to 0° C.) in a portionwise manner. Slow quenching is desirable because the reduction of excess permanganate is exothermic. The mixture was stirred at 0° C. until no purple color remained, then washed with a cooled (0° C.) 1N NaOH solution (200 ml). The organic layer was separated, dried over MgSO$_4$, concentrated, and subjected to chromatography, yielding the title compound as a yellow solid (3.58 g, 95%).

Step 4: Preparation of 5-(2-Fluororhenyl)-4-[4-(methylsulfonyl)phenyl]-2-(trifluoromethyl)-1H-imidazole The title compound was prepared from the dione in the previous step (11 mmol, 3.43 g) using the method of Example 59, step 5, except that the reaction was at reflux 8 hours. Purification consisted of chromatography [hexane:ethyl acetate (2:1), then methylene chloride/ethyl acetate (9:1)], recrystallization from ethyl acetate/hexane, and drying by concentration from acetone solution, affording a white solid (508 mg, 12%). Mass spectrum (EI, M/e): 384. Anal. Calc'd. for C$_{17}$H$_{12}$F$_4$N$_2$O$_2$S: C, 53.13; H, 3.15; N, 7.29. Found: C, 53.01; H, 3.04; N, 6.76.

EXAMPLE 65

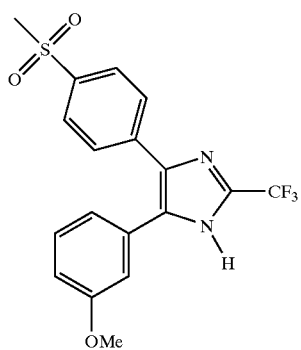

5-(3-Methoxyphenyl)-4-[4-(methylsulfonyl)phenyl]-2-(trifluoromethyl)-1H-imidazole Step 1 Preparation (3-Methoxyphenyl) methyltriphenylphosohonium Chloride The title compound was prepared from (80 mmol, 11.6 ml) of 3-methoxybenzyl chloride by the method of Example 64, step 1, except that the reaction was heated 3 days at reflux, affording the title compound (21.6 g, 65%).

Step 2 Preparation of 1-Methoxy-3-[2-[4-(methylsulfonyl)phenyl]ethylenyl]benzene The title compound was prepared by method of Example 64, step 2. From 20 mmol phosphonium salt (8.36 g) was obtained 5.47 g (95%) of the title compound.

Step 3 Preparation of 1-(3-Methoxyphenyl)-2-[4-(methylsulfonyl)phenyl]ethane-1,2-dione The title compound was obtained from 1-methoxy-3-[2-[4-(methylsulfonyl)phenyl]ethylenyl]benzene (Step 2) (18.4 mmol, 5.29 g), using the method of Example 64, step 3, and affording the desired dione as a yellow solid (1.55 g, 27%).

Step 4 Preparation of 5-(3-Methoxyphenyl)-4-[4-(methylsulfonyl)phenyl]-2-(trifluoromethyl)-1H-imidazole The title compound was prepared from the dione in the previous step (4.9 mmol, 1.55 g) using the method of Example 59, step 5, except that the reaction was at reflux for 5 hours. Purification consisted of chromatography (9:1 methylene chloride:ethyl acetate), followed by recrystallization from ethyl acetate/hexane, affording a white solid (676 mg, 35%): mp (DSC)=202–208° C. Anal. Calc'd. for C$_{18}$H$_{15}$F$_3$N$_2$O$_3$S.1/3H$_2$O: C, 53.73; H, 3.92; N, 6.96. Found: C, 53.78; H, 3.63; N. 6.45.

EXAMPLE 66

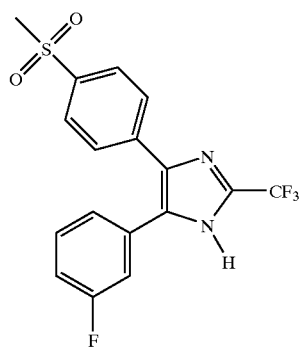

5-(3-Fluorophenyl)-4-[4-(methylsulfonyl)phenyl]-2-(trifluoromethyl)-1H-imidazole Step 1 Preparation (3-Fluorophenyl) methyltriphenylphosdhonium Bromide The title compound was prepared from (80 mmol, 11.6 ml) of 3-fluorobenzyl bromide by the method of Example 64, step 1, except that the reaction was stirred 3 days at ambient, affording the title compound (27.1 g, 76%).

Step 2 Preparation of 1-Fluoro-3-[2-[4-(methylsulfonyl)phenyl]ethylenyl]benzene

The title compound was prepared by method of Example 64, step 2. From 20 mmol phosphonium salt (8.80 g) was obtained 2.68 g (48%) of the title compound.

Step 3 Preparation of 1-(3-Fluorophenyl)-2-[4-(methylsulfonyl)-phenyl]ethane-1,2-dione The title compound was obtained from 1-fluoro-3-[2-[4-(methylsulfonyl)phenyl]ethylenyl]benzene (Step 2) (9.71 mmol, 2.68 g), using the method of Example 64, step 3, and affording the desired dione as a yellow solid (770 mg, 26%).

Step 4 Preparation of 5-(3-Fluorophenyl)-4-[4-(methylsulfonyl)phenyl]-2-(trifluoromethyl)-1H-imidazole The title compound was prepared from the dione in the previous step (2.5 mmol, 770 mg) using the method of Example 59, step 5, except that the reaction was at reflux 5 hours. Purification consisted of chromatography (20:1 methylene chloride:ethyl acetate), followed by recrystallization from ethyl acetate/hexane, affording a white solid (377 mg, 39%): Mass spectrum (EI, M/e): 384. mp (DSC)=225–229° C. Anal. Calc'd. for C$_{17}$H$_{12}$F$_4$N$_2$O$_2$S: C, 53.13; H, 3.15; N, 7.29. Found: C, 52.98; H, 3.01; N, 7.04.

EXAMPLE 67

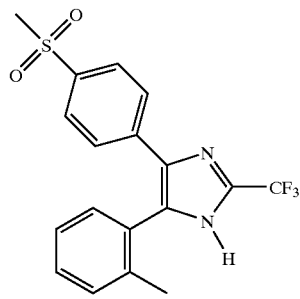

5-(2-Methylphenyl)-4-[4-(methylsulfonyl)phenyl]-2-(trifluoromethyl)-1H-imidazole Step 1 Preparation (2-Methylphenyl) methyltriphenylphosphonium Bromide The title compound was prepared from (105 mmol, 14.1 ml) of 2-fluorobenzyl bromide by the method of Example 64, step 1, except that the reaction was stirred 3 days at ambient, affording the title compound (39.8 g, 85%).

Step 2: Preparation of 1-Methyl-2-[2-[4-(methylsulfonyl)phenyl]ethylenyl]benzene The title compound was prepared by method of Example 64, step 2. From 40 mmol phosphonium salt (17.9 g) was obtained 10.5 g (96%) of the title compound.

Step 3: Preparation of 1-(2-Methylphenyl)-2-[4-(methylsulfonyl)phenyl]ethane-1,2-dione The title compound was obtained from 1-methyl-2-[2-[4-(methylsulfonyl)phenyl]ethylenyl]benzene (Step 2) (38.8 mmol, 10.5 g), using the method of Example 64, step 3, and affording the desired dione as a yellow solid (3.50 mg, 28%).

Step 4: Preparation of 5-(2-Methylphenyl)-4-[4-(methylsulfonyl)phenyl]-2-(trifluoromethyl)-1H-imidazole The title compound was prepared from the dione in the previous step (11 mmol, 10.5 g) using the method of Example 59, step 5, except that the reaction was at reflux 6 hours. Purification consisted of chromatography (20:1 methylene chloride:ethyl acetate), followed by recrystallization from ethyl acetate/hexane, affording a white solid (299 mg, 39%). mp (DSC) 180–190° C. Anal. Calc'd. for $C_{18}H_{15}F_3N_2O_2S$.(1/2 $H_2O$): C, 55.52; H, 4.14; N, 7.19. Found: C, 55.67; H, 3.89; N, 6.60.

EXAMPLE 68

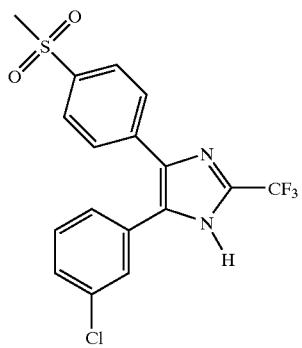

5-(3-Chlorophenyl)-4-[4-(methylsulfonyl)phenyl]-2-(trifluoromethyl)-1H-imidazole Step 1 Preparation (3-Chlorophenyl) methyltriphenylphosphonium Bromide The title compound was prepared from 3-chlorobenzyl chloride (100 mmol, 12.7 ml) by the method of Example 64, step 1, affording after three days of reflux the desired white solid (9.03 g, 20%).

Step 2: Preparation of 1-Chloro-3-[2-[4-(methylsulfonyl)phenyl]ethylenyl]benzene The title compound was prepared by method of Example 64, step 2. From 21 mmol phosphonium salt (8.92 g) was obtained 4.72 g (76%) of the title compound.

Step 3: Preparation of 1-(3-Chlorophenyl)-2-[4-(methylsulfonyl)phenyl]ethane-1,2-dione The title compound was obtained from the product of step 2 (15.2 mmol, 4.44 g), using the method of Example 64, step 3, and affording the desired dione as a yellow solid (2.90 g, 60%).

Step 4 Preparation of 5-(3-Chlorophenyl)-4-[4-(methylsulfonyl)phenyl]-2-(trifluoromethyl)-1H-imidazole The title compound was prepared from the dione in the previous step (9.0 mmol, 2.9 g) using the method of Example 59, step 5, except that the reaction was at reflux 6 hours. Purification consisted of chromatography (20:1 methylene chloride:ethyl acetate), followed by recrystallization twice from ethyl acetate/hexane, affording a white solid (730 mg, 20%). mp (DSC) 224–226° C. Mass spectrum (EI, M/e): 400. Anal. Calc'd. for $C_{17}H_{12}ClF_3N_2O_2S$: C, 50.94; H, 3.02; N, 6.99. Found: C, 50.81; H, 3.03; N, 6.84.

EXAMPLE 69

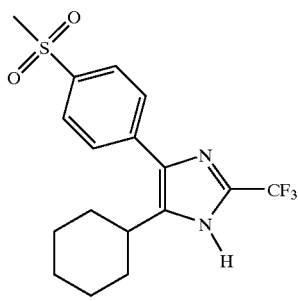

5-(Cyclohexyl)-4-[4-(methylsulfonyl)phenyl]-2-(trifluoromethyl)-1H-imidazole

Step 1 Preparation of 4-(Methylsulfonyl)benzyl Alcohol 4-(Methylthio)benzyl alcohol (50 mmol, 7.71 g) was dissolved in methanol (150 ml) and cooled to 0° C. Oxone® (110 mmol, 67.6 g) in water (250 ml) was added. The stirred mixture was warmed to room temperature after 5 minutes. After 40 minutes, the mixture was diluted with water (250 ml), and extracted with methylene chloride (300 ml, then 2×100 ml). The combined organic layers were dried ($MgSO_4$), filtered through silica, and concentrated to afford the title compound (5.48 g, 58%) as a waxy solid.

Step 2 Preparation of 4-(Methylsulfonyl)phenylmethyl Triphenylphosphonium Bromide Dimethyl sulfide (36 mmol, 2.64 ml) was added to a 0° C. suspension of recently recrystallized (water) N-bromosuccinimide (30 mmol, 5.37) in methylene chloride. After 3 minutes, the mixture was chilled to –30° C., and the alcohol from step 1 (20 mmol, 3.72 g) was added as a solid. After 10 minutes, the reaction was warmed to 0° C. After 1.5 hours, the reaction was warmed to ambient temperature, and stirred an additional 2 hours. The reaction product was poured directly onto a column and was eluted with methylene chloride. Concentration afforded the intermediate benzyl bromide as a white solid (4.55 g, 90%), which was diluted with toluene (30 ml) and tetrahydrofuran (10 ml). Triphenylphosphine (18.5 mmol, 4.85 g) was added, and the reaction was stirred 4 days at ambient temperature, then subjected to filtration to isolate the title compound (8.78, 85% overall), as a white solid.

Step 3 Preparation of 1-Methylsulfonyl-4-[2-cyclohexylethylenyl]benzene

The phosphonium salt from step 2 (5.18 mmol, 2.64 g) was suspended in ethanol (10 ml) and cooled to 0° C. n-Butyllithium (1.6 M in hexane, 3.44 ml) was added over 5 minutes. After an additional 5 minutes, cyclohexanecarboxaldehyde (5.5 mmol, 0.67 ml) was introduced, and the reaction was heated to reflux. The reaction was cooled after 3 hours, concentrated, and subjected to chromatography (3:1 hexane/ethyl acetate). The title compound (1.73 g, ~quant.) was obtained as a semi-solid mixture of olefin isomers (plus some triphenylphosphine oxide).

Step 4 Preparation of 1-(Cyclohexyl)-2-[4-(methylsulfonyl)phenyl]ethane-1,2-dione The title compound was obtained from the compound of step 3 (6.08 mmol, 1.61 g), using the method of Example 64, step 3, and affording the desired dione as a yellow solid (1.05 g, 57%).

Step 5 Preparation of 5-(Cyclohexyl)-4-[4-(methylsulfonyl) phenyl]-2-(trifluoromethyl)-1H-imidazole The title compound was prepared from the dione in the previous step (3.5 mmol, 1.02 g) using the method of Example 59, step 5, except that the reaction was at reflux 4 hours. Purification consisted of chromatography (20:1 methylene chloride:ethyl acetate), followed by recrystallization from ethyl acetate/hexane (×2), affording a white solid (140 mg, 11%): mp (DSC) 250–253° C. Mass spectrum (EI, M/e): 372. Anal. Calc'd. for $C_{17}H_{19}F_3N_2O_2S$: C, 54.84; H, 5.14; C, 7.52. Found: C, 54.69; H, 5.12; N, 7.39.

EXAMPLE 70

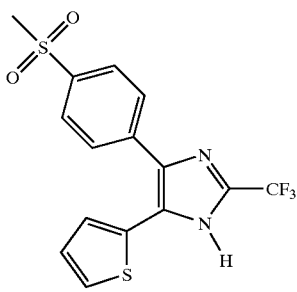

4-[4-(Methylsulfonyl)phenyl]-5-(2-thiophenyl)-2-(trifluoromethyl)-1H-imidazole

Step 1 Preparation of [4-(Methylsulfonyl)phenyl]ethylenyl]-2-thiophene

The title compound was prepared by the method of Example 69, step 3. From 5.2 mmol (0.48 ml) of thiophene-2-carboxaldehyde, 0.67 g (49%) of the desired olefin was obtained as a yellow solid.

Step 2 Preparation of 1-[4-(Methylsulfonyl)phenyl]-2-(2-thiophenyl)ethane-1,2-dione The olefin from the previous step (2.5 mmol, 0.67 g) was transformed by the method of Example 64, step 3 into the title compound, a yellow semisolid (357 mg, 44%).

Step 3 Preparation of 4-[4-(Methylsulfonyl)phenyl]-5-(2-thiophenyl)-2-(trifluoromethyl)-1H-imidazole The dione (1.1 mmol, 325 mg) was converted to final product by the method of Example 59, step 5, affording, after ethyl acetate/hexane recrystallization, a tan solid (78 mg): mp (DSC)=95–97° C. Mass spectrum (EI, M/e): 372. Anal. Calc'd. for $C_{15}H_{11}F_3N_2O_2S_2$: C, 48.38; H, 2.98; N, 7.52. Found: C, 48.30; H, 2.99; N, 7.02.

EXAMPLE 71

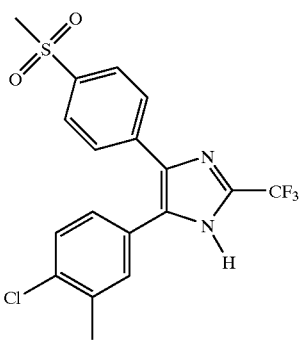

5-(4-Chloro-3-methylphenyl)-4-[4-(methylsulfonyl) phenyl]-2-(trifluoromethyl)-1H-imidazole Step 1 Preparation of 4-(Methylsulfonyl)phenylmethyl triphenylphosphonium Chloride 4-(Methylsulfonyl)benzyl chloride (Transworld Chemical) (121 mmol, 24.7 g) and triphenylphosphine (130 mmol, 34.1 g) were heated at reflux in toluene (125 ml) with stirring for 56 hours. The reaction was cooled, and the title compound was collect by filtration (48.0 g, 85%).

Step 2 Preparation of 4-Chloro-3-methylbenzaldehyde

4-Chloro-3-methylbenzoic acid, methyl ester (Lancaster) (29 mmol, 5.40 g) was dissolved in methylene chloride (30 ml) and cooled to 0° C. Diisobutylaluminum hydride (1 M in toluene, 64 ml) was added slowly (over ca. 10 minutes). One hour after complete addition, the reaction was quenched with methanol (64 ml), then poured into ether (500 ml). This mixture was stirred at room temperature 1 hour, filtered through silica gel and Celite®, eluting with addition ether. Concentration afforded 4-chloro-3-methylbenzyl alcohol (23 mmol, 3.53 g) as a solid, which was diluted with methylene chloride (46 ml), combined with Celite® (3.5 g) and $MgSO_4$ (1.5. g), and cooled to 0° C. Pyridinium chlorochromate (45 mmol, 9.67 g) was added over 2–3 minutes. In 1 hour's time, the reaction mixture was filtered through silica and concentrated to afford 4-chloro-3-methylbenzaldehyde as a waxy solid (2.10 g, 47% overall), which was used in the next step.

Step 3 Preparation of 1-Chloro-2-methyl-4-[2-[4-(methylsulfonyl)phenyl]ethylenyl]benzene The aldehyde from step 2 (11 mmol, 1.69 g) was reacted with the phosphonium chloride from step 1, under the-reaction conditions established in Example 69, step 3, affording the title compound as a solid (3.09 g, ~quant.), which was used in the next step.

Step 4: Preparation of 1-(4-Chloro-3-methylphenyl)-2-[4-(methylsulfonyl)phenyl]ethane-1,2-dione The title compound was obtained from the product of step 3 (10 mmol, 3.1 g), using the method of Example 64, step 3, and affording the desired dione as a yellow solid (0.63 g, 19%).

Step 5 Preparation of 5-(4-Chloro-3-methylphenyl)-4-[4-(methylsulfonyl)phenyl]-2-(trifluoromethyl)-1H-imidazole The title compound was prepared from the dione in the previous step (1.86 mmol, 625 mg) using the method of Example 59, step 5, except that the reaction was at reflux 6 hours. Purification consisted of chromatography (20:1 methylene chloride:ethyl acetate), followed by recrystallization twice from ethyl acetate/hexane, affording a white solid (344 mg, 45%): mp (DSC)=261–264° C. Anal. Calc'd. for $C_{18}H_{14}ClF_3N_2O_2S$: C, 52.12; H, 3.40; N, 6.75. Found: C, 52.50; H, 3.46; N, 6.33.

EXAMPLE 72

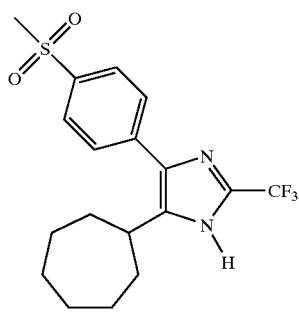

5-[4-Cycloheptyl)-4-[4-(methylsulfonyl)phenyl]-2-(trifluoromethyl)-1H-imidazole

Step 1 Preparation of Cycloheptanecarboxaldehyde

Cycloheptanemethanol (20 mmol, 2.56 g) was combined with methylene chloride (40 ml), Celite® (2.56 g), and MgSO$_4$ (0.5 g). Pyridinium chlorochromate (30 mmol, 6.47 g) was added. After 2.5 hours, the mixture was filtered through silica and concentrated, affording the title compound as an oil (2.33 g, 91%).

Step 2 Preparation of 1-Methylsulfonyl-4-(2-cycloheptylethylenyl]benzene

The aldehyde from step 1 (5 mmol, 1.34 g) was reacted with the phosphonium chloride from Example 71, step 1, under the reaction conditions established in Example 69, step 3, affording the title compound as a solid (1.34 g, ~quant.), which was used in the next step.

Step 3 Preparation of 1-(Cycloheptyl)-2-[4-(methylsulfonyl)phenyl]ethane-1,2-dione The title compound was obtained from the compound of step 2 (5.0 mmol, 1.34 g), using the method of Example 64, step 3, and affording the desired dione as a yellow semi-solid. (1.34 g, 87%).

Step 4 Preparation of 5-[4-Cycloheptyl)-4-[4-(methylsulfonyl)phenyl]-2-(trifluoromethyl)-1H-imidazole The title compound was prepared from the dione in the previous step (4.35 mmol, 1.34 g) using the method of Example 59, step 5, except that the reaction was at reflux 6 hours. Purification consisted of chromatography (20:1 methylene chloride:ethyl acetate), followed by recrystallization twice from ethyl acetate/hexane, affording a white solid (368 mg, 22%): mp (DSC)=206–207° C. Anal. Calc'd. for C$_{18}$H$_{21}$F$_3$N$_2$O$_2$S: C, 55.95; H, 5.48; N, 7.25. Found: C, 55.83; H, 5.37; N, 7.16.

EXAMPLE 73

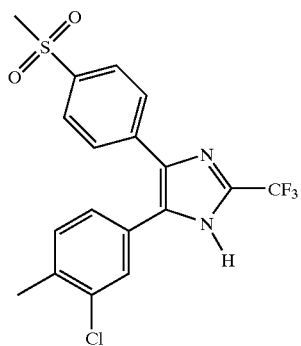

5-(3-Chloro-4-methylphenyl)-4-[4-(methylsulfonyl)phenyl]-2-(trifluoromethyl)-1H-imidazole Step 1: Preparation of 3-Chloro-4-methylbenzaldehyde 3-Chloro-4-methylbenzonitrile (12 mmol, 1.82 g) was dissolved in methylene chloride (12 ml) and cooled to 0° C. Diisobutylaluminum hydride (1 M in toluene, 13 ml) was added over several minutes, and the ice bath was removed. After 2.5 hours, the reaction was quenched at 0° C. with acetaldehyde (4 ml), then after 5 minutes, poured into ice-cold 5% HCl (100 ml). The product was extracted using methylene chloride (150 ml) and the organic layer was dried using magnesium sulfate. Filtration through silica, followed by concentration afforded the title compound, an oil (1.61, 88%), which was used in the next step.

Step 2 Preparation of 1-Chloro-2-methyl-5-(2-[4-(methylsulfonyl)phenyl]ethylenyl]benzene The aldehyde from step 1 (10 mmol, 1.61 g) was reacted with the phosphonium chloride from Example 71, step 1, under the reaction conditions established in Example 69, step 3, affording the title compound as a solid (2.70 g, 88%.), which was used in the next step.

Step 3 Preparation of 1-(3-Chloro-4-methylphenyl)-2-[4-(methylsulfonyl)phenyl]ethane-1,2-dione The title compound was obtained from the compound of step 2 (8.8 mmol, 2.7 g), using the method of Example 64, step 3, and affording the desired dione as a yellow solid (1.90 g, 64%).

Step 4 Preparation of 5-(3-Chloro-4-methylphenyl)-4-[4-(methylsulfonyl)phenyl]-2-(trifluoromethyl)-1H-imidazole The title compound was prepared from the dione in the previous step (5.6 mmol, 1.90 g) using the method of Example 59, step 5, except that the reaction was at reflux 6 hours. Purification consisted of chromatography (20:1 methylene chloride:ethyl acetate), followed by recrystallization twice from acetone/hexane, affording a white solid (359 mg, 15%): mp (DSC)=273–275° C. Mass spectrum (EI, M/e): 414. Anal. Calc'd. for C$_{18}$H$_{14}$ClF$_3$N$_2$O$_2$S: C, 52.12; H, 3.40; N, 6.75. Found: C, 52.32; H, 3.36; N, 6.65.

EXAMPLE 74

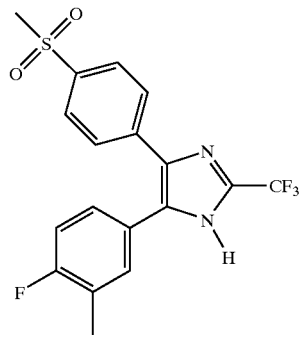

5-(4-Fluoro-3-Methylphenyl)-4-[4-(methylsulfonyl)phenyl]-2-(trifluoromethyl)-1H-imidazole Step 1 Preparation of 4-Fluoro-3-methylbenzaldehyde 5-Bromo-2-fluoro-toluene (26 mmol, 5.0 g) was dissolved in tetrahydrofuran (25 ml) and cooled to −78° C. t-Butyllithium (1.7 M in pentane, 31 ml) was added over 10 minutes. After 30 minutes, N,N-dimethylformamide (2.1 ml) was added. The reaction mixture was warmed to ambient over 30 minutes and 6% HCl (100 ml) was added with vigorous swirling. The mixture was extracted with ethyl acetate (200 ml). The organic layer was dried over MgSO$_4$, then concentrated affording the title compound as an oil (3.6 g, ~quant.).

Step 2: Preparation of 1-Fluoro-2-methyl-4-[2-[4-(methylsulfonyl)phenyl]ethylenyl]benzene The aldehyde from step 1 (10 mmol, 1.5 g) was reacted with the phosphonium chloride from Example 71, step 1, under the reaction conditions established in Example 69, step 3, affording the title compound as a solid (2.98 g, ~quant.), which was used in the next step.
Step 3: Preparation of 1-(4-Fluoro-2-methylphenyl)-2-[4-(methylsulfonyl)phenyl]ethane-1,2-dione The title compound was obtained from the compound of step 2 (10 mmol, 2.98 g), using the method of Example 64, step 3, and affording the desired dione as a yellow solid (2.2 g, 69%).
Step 4 Preparation of 5-(3-Fluoro-2-methylphenyl)-4-[4-(methylsulfonyl)phenyl]-2-(trifluoromethyl)-1H-imidazole The title compound was prepared from the dione in the previous step (6.9 mmol, 2.2 g) using the method of Example 59, step 5, except that the reaction was at reflux 6 hours. Purification consisted of chromatography (20:1 methylene chloride:ethyl acetate), followed by recrystallization twice from acetone/hexane, affording a white solid (204 mg, 7%): Anal. Calc'd. for $C_{18}H_{14}F_4N_2O_2S$: C, 54.27; H, 3:54; N, 7.03. Found: C, 54.33; H, 3.49; N, 6.39.

EXAMPLE 75

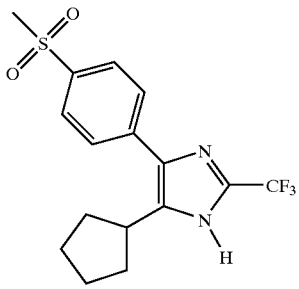

5-(Cyclopentyl)-4-[4-(methylsulfonyl)phenyl]-2-(trifluoromethyl)-1H-imidazole
Step 1 Preparation of Cyclopentanecarboxaldehyde Cyclopentanemethanol (40 mmol, 4.3 g) was combined with methylene chloride (60 ml), Celite® (4.3 g), and $MgSO_4$ (1 g). Pyridinium chlorochromate (60 mmol, 12.9 g) was added. After 2.5 hours, the mixture was filtered through silica and concentrated, affording the title compound as a volatile oil (1.7 g, 44%).
Step 2 Preparation of 1-Methylsulfonyl-4-[2-cyclopentylethylenyl]benzene The aldehyde from step 1 (~20 mmol, excess) was reacted with the phosphonium chloride from Example 71, step 1 (12 mmol, 5.59 g), under the reaction conditions established in Example 69, step 3, affording the title compound as a solid (3.28 g, ~quant.), which was used in the next step.
Step 3 Preparation of 1-(Cyclopentyl)-2-[4-(methylsulfonyl)phenyl]ethane-1,2-dione The title compound was obtained from the compound of step 2 (12 mmol, 3.28 g), using the method of Example 64, step 3, and affording the desired dione as a yellow semi-solid (1.05 g, 31%).
Step 4 Preparation of 5-(Cyclopentyl)-4-[4-(methylsulfonyl)phenyl]-2-(trifluoromethyl)-1H-imidazole The title compound was prepared from the dione in the previous step (3.7 mmol, 1.05 g) using the method of Example 59, step 5, except that the reaction was at reflux 4 hours. Purification consisted of chromatography (20:1 methylene chloride:ethyl acetate), followed by recrystallization from ethyl acetate/hexane, then acetone/hexane, affording a white solid (501 mg, 38%): mp (DSC)=210–212° C. Anal. Calc'd. for $C_{16}H_{17}F_3N_2O_2S$: C, 53.62; H, 4.78; N, 7.82. Found: C, 53.43; H, 4.63; N, 7.67.

EXAMPLE 76

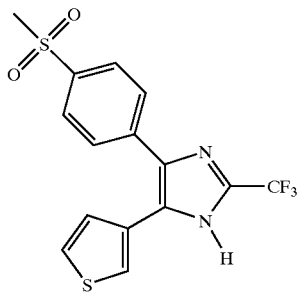

4-[4-(Methylsulfonyl)phenyl]-5-(3-thiophenyl)-2-(trifluoromethyl)-1H-imidazole
Step 1 Preparation of [-4-(Methylsulfonyl)phenyl]ethylenyl]-3-thiophene The title compound was prepared by the method of Example 69, step 3 using the phosphonium chloride from Example 71, step 1. From 10.5 mmol (0.92 ml) of thiophene-3-carboxaldehyde, 2.64 g (~quant) of the desired olefin was obtained as a solid.
Step 2 Preparation of 1-[4-(Methylsulfonyl)phenyl]-2-(3-thiophenyl)ethane-1,2-dione The olefin from the previous step (10 mmol, 2.64 g) was transformed by the method of Example 64, step 3 into the title compound, a yellow semisolid (1.25g, 42%).
Step 3 Preparation of 4-[4-(Methylsulfonyl)phenyl]-5-(3-thiophenyl)-2-(trifluoromethyl)-1H-imidazole The dione (4.25 mmol, 1.25 g) was converted to final product by the method of Example 59, step 5, affording, after recrystallization twice from acetone/hexane, 408 mg (26%). mp (DSC)=230–232° C. Mass spectrum (EI, M/e): 372. Anal. Calc'd. for $C_{15}H_{11}F_3N_2O_2S_2$: C, 48.38; H, 2.98; N, 7.52. Found: C, 48.49; H, 2.93; N, 7.34.

EXAMPLE 77

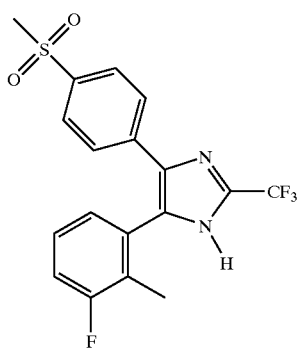

5-(3-Fluoro-2-methylphenyl)-4-[4-(methylsulfonyl)phenyl]-2-(trifluoromethyl)-1H-imidazole
Step 1 Preparation of 3-Fluoro-2-methyl-3-[2-[4-(methylsulfonyl)phenyl]ethylenyl]benzene The 3-fluoro-2-methylbenzaldehyde (10 mmol, 1.2 g) was reacted with the phosphonium chloride from Example 71, step 1, under the reaction conditions established in Example 69, step 3, affording the title compound as a solid (2.9 g, ~quant.), which was used in the next step.

Step 2 Preparation of 1-(3-Fluoro-2-methylphenyl)-2-[4-(methylsulfonyl)phenyl]ethane-1,2-dione The title compound was obtained from the compound of step 2 (10 mmol, 2.9 g), using the method of Example 64, step 3, and affording the desired dione as a yellow solid (1.9 g, 59%).

Step 3 Preparation of 5-(3-Fluoro-2-methylphenyl)-4-[4-(methylsulfonyl)phenyl]-2-(trifluoromethyl)-1H-imidazole The title compound was prepared from the dione in the previous step (6.9 mmol, 2.2 g) using the method of Example 59, step 5, except that the reaction was at reflux 6 hours. Purification consisted of chromatography (20:1 methylene chloride:ethyl acetate), followed by recrystallization twice from acetone/hexane, which gave a white solid (184 mg, 6%). mp (DSC) 192–196° C. Anal. Calc'd. for $C_{18}H_{14}F_4N_2O_2S$: C, 54.27; H, 3.54; N, 7.03. Found: C, 54.23; H, 3.18; N, 6.76.

EXAMPLE 78

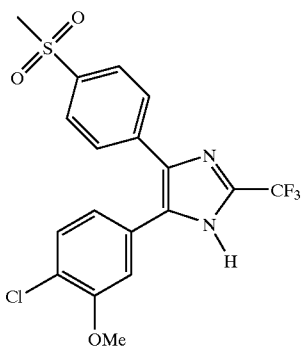

5-(4-Chloro-3-methoxyphenyl)-4-[4-(methylsulfonyl)phenyl]-2-(trifluoromethyl)-1H-imidazole Step 1 Preparation of 2-Chloro-5-methylanisole 2-Chloro-5-methylphenol (50 mmol, 7.13 g), NaOH pellets (60 mmol, 2.4 g), and methanol (50 ml) were stirred together until a homogeneous solution was obtained. The flask was cooled to 0° C., and methyl iodide (60 mmol, 3.77 ml) was added. The reaction was warmed over 2 hours to ambient and stirred for 16 hours. Reaction was still incomplete by thin layer chromatography; additional NaOH (~300 mg) and $CH_3I$ (~5 ml) was introduced, and stirring continued for another 24 hours. TLC again indicated incomplete conversion, so additional time and reagents were again applied. The mixture was at length concentrated, diluted with water (50 ml), and extracted with methylene chloride (2×25 ml). The combined organic layer was dried ($MgSO_4$), filtered through silica, and concentrated to afford the title compound as an oil (5.09 g, 65%).

Step 2 Preparation (4-Chloro-3-methoxyphenyl)methyltriphenylphosphonium Bromide

The compound from step 1 (33 mmol, 5.1 g) was combined with N-bromosuccinimide (33 mmol, 5.1 g) and benzoyl peroxide (1 mmol, 240 mg) in $CCl_4$ (40 ml) and heated for 3 hours at reflux. The mixture was diluted with additional $CCl_4$ (~60 ml), filtered trough Celite®, and washed with sodium bisulfite solution (1 g/10 ml water). The organic layer was dried ($MgSO_4$), concentrated, and azeotroped with toluene (~20 ml). The residue was dissolved in toluene (50 ml) and triphenylphosphine (32 mmol, 8.54 g) was added. After 3 days, the product was collected by filtration (1.95 g, 12%).

Step 3 Preparation of 1-Chloro-2-methoxy-4-[2-[4-(methylsulfonyl)phenyl]ethylenyl]benzene The title compound was prepared by method of Example 64, step 2. From 5.5 mmol phosphonium salt (2.7 g) was obtained 1.40 g (80%) of the title compound.

Step 4 Preparation of 1-(4-Chloro-3-methoxyphenyl)-2-[4-(methylsulfonyl)phenyl]ethane-1,2-dione The title compound was obtained from the compound of step 3 (4.33 mmol, 1.39 g), using the method of Example 64, step 3, and affording the desired dione as a yellow solid (580 mg, 38%).

Step 5: Preparation of 5-(4-Chloro-3-methoxyphenyl)-4-[4-(methylsulfonyl)phenyl]-2-(trifluoromethyl)-1H-imidazole The title compound was prepared from the dione in the previous step (1.65 mmol, 580 mg) using the method of Example 59, step 5, except that the reaction was at reflux for 5 hours. Purification, which consisted of chromatography (20:1 methylene chloride:ethyl acetate), followed by recrystallization twice from ethyl acetate/hexane, afforded a white solid (84 mg, 12%). Mass spectrum (EI, M/e): 430. mp (DSC)=233–234° C. Anal. Calc'd. for $C_{18}H_{14}ClF_3N_2O_3S$: C, 50.18; H, 3;28; N, 6.50. Found: C, 50.33; H, 3.63; N, 5.76.

EXAMPLE 79

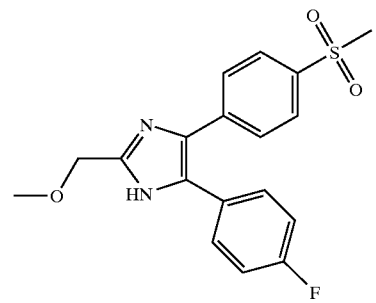

5-(4-Fluorophenyl)-2-(methoxymethyl)-4-[4-(methylsulfonyl)-phenyl]-1H-imidazole

Step 1 Preparation of 1-(1-Ethoxyethyl)-4-(4-fluorophenyl)-5-[4-(methylthio)phenyl]1-H-imidazol-2-yl]-1H-imidazole-2-methanol A solution of 5-(4-fluorophenyl)-4-(4-methylthiophenyl)-1-(1-methyl-1-ethoxymethyl)-1H-imidazole (Example 9, step 2) (4.19 g; 11.75 mmol) and tetramethylethylene diamine (TMEDA) (4.1 g mg; 13.39 mmol) in tetrahydrofuran (30 mL), was cooled to –70° C. under an argon atmosphere. n-Butyllithium (5.1 mL, 1.6 M in hexane, 12.9 mmol) was added and the solution was stirred at –78° C. for 15 minutes. Dimethylformamide (859 mg; 0.90 mL) was added and the solution was warmed to 0° C. The reaction was quenched by the addition of a saturated $NaHCO_3$ solution and extracted with diethyl ether. The organic extracts were dried ($MgSO_4$), filtered and concentrated in vacuo. The crude compound was redissolved in 23.5 ml of methanol and to this solution was added sodium borohydride (789.6 mg; 23.4 mmol). After stirring for 1 hour at 25° C., the reaction was quenched with a 1% aqueous hydrochloric acid solution till evidence of gas evolution ceased. The solution was extracted with methylene chloride, dried ($MgSO_4$), filtered and concentrated in vacuo. The residue was purified by chromatography ($SiO_2$; ethyl acetate/hexane) to yield ca. 4 g of the desired compound.

Step 2: Preparation of 5-(4-Fluorophenyl)-2-(methoxymethyl)-4-[4-(methylsulfonyl)-phenyl]-1H-imidazole To a solution of 1-(1-ethoxyethyl)-4-(4-fluorophenyl)-5-[4-(methylthio)phenyl]-1H-imidazol-2-yl]-1H-imidazole-2-methanol (Step 1) (549.3 mg; 1.42 mmol) in 5.6 ml of THF, at 25° C., was added 34.0 mg (1.42 mmol) of dry sodium hydride. After all the solids were dissolved, 88 μl of methyl iodide (201.55 g; 1.42 mmol) was added. After stirring at 25° C. for two hours, the reaction was diluted with 25 ml of ether and this solution was washed with 25 ml of water. The organic extracts were dried (MgSO$_4$), evaporated to dryness under reduced pressure, and purified with flash chromatography (SiO$_2$; 90/10 toluene/methanol) to give 334 mg of material containing the desired product. This material was dissolved in 16 ml of methanol/THF (1.6:1). Oxone® (900 mg) was dissolved in 4 ml of water and added to this solution all at once. After stirring the reaction at 25° C. for 2 hours, the reaction was poured into water and extracted with methylene chloride. The organic extracts were dried (MgSO$_4$) and evaporated under reduced pressure to give a white solid. Purification by preparative thin layer chromatography (SiO$_2$; 90/10 toluene/ethyl acetate) gave 33 mg of the desired sulfone: mp 169° C. Anal. Calc'd. for $C_{18}H_{17}FN_2O_3S$: C, 59.99; H, 4.75; N 7.77. Found: C, 59.47; H, 4.66; N, 7.32.

EXAMPLE 80

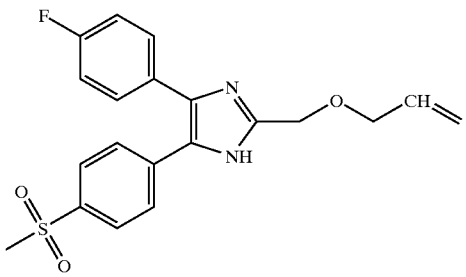

4-(4-Fluorophenyl)-5-[4-(methylsulfonyl)phenyl]-2-[(2-propenyloxy)methyl]-1H-imidazole To a solution of 1-(1-ethoxyethyl)-4-(4-fluorophenyl)-[4-(methylthio)phenyl]-H-imidazol-2-yl]-1H-imidazole-2-methanol (Example 79, Step 1) (200 mg; 0.52 mmol) in 2 ml of DMF, at 25° C., was added 20.0 mg (0.52 mmol) of sodium hydride (60% mineral oil dispersion). After stirring at 25° C. for 15–20 minutes, 44 μl of allyl bromide (62.9 mg; 0.52 mmol) was added. After stirring at 25° C. for 2 hours, the reaction was diluted with 40 ml of ethyl acetate and washed with 3×30 ml of brine. The organic extracts were dried (MgSO$_4$), and evaporated to dryness under reduced pressure to provide 184 mg of a oil, which was purified by flash chromatography (SiO$_2$; 25% ethyl acetate/toluene) to give 96 mg of the desired intermediate. This material was dissolved in 8 ml of methanol/THF (1.6:1). Oxone® (450 mg) was dissolved in 2 ml of water and added to this solution all at once. After stirring the reaction at 25° C. for 1.5 hours, the reaction was poured into 50 ml of methylene chloride and extracted with 2×50 ml of water. The organic extracts were dried (MgSO$_4$) and evaporated under reduced pressure to give 82.5 mg of a white solid which was further purified by preparative thin layer chromatography (SiO$_2$; 75/25 ethyl acetate/toluene) to give 56.4 mg of the desired sulfone: Anal. Calc'd. for $C_{20}H_{19}FN_2O_3S+0.5$ mol $H_2O$: C, 60.75; H, 5.10; N 7.08; S, 8.11. Found: C, 60.53; H, 4.83; N, 6.93; S, 8.11.

EXAMPLE 81

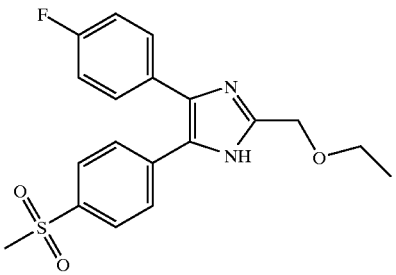

2-(Ethoxymethyl)-4-(4-fluorophenyl)-5-[4-(methylsulfonyl)phenyl]-1H-imidazole

To a solution of 1-(1-ethoxyethyl)-4-(4-fluorophenyl)-5-[4-(methylthio)phenyl]-1H-imidazol-2-yl]-1H-imidazole-2-methanol (Example 79, Step 1) 200 mg; 0.52 mmol) in 2 ml of DMF, at 25° C., was added 20.0 mg (0.52 mmol) of sodium hydride (60% mineral oil dispersion). After stirring at 25° C. for 15–20. minutes, 41 μl of ethyl iodide (81.0 mg; 0.52 mmol) was added. After stirring at 25° C. for 22 hours, the reaction was diluted with 40 ml of ethyl acetate and washed with 3×30 ml of brine. The organic extracts were dried (MgSO$_4$), and evaporated to dryness under reduced pressure to provide 151 mg of a orange oil, which was purified by flash chromatography (SiO$_2$; 25% ethyl acetate/toluene) to give 40.6 mg of the desired intermediate. This material was dissolved in 8 ml of methanol/THF (1.6:1). Oxone® (450 mg) was dissolved in 2 ml of water and added to this solution all at once. After stirring the reaction at 25° C. for 1.5 hours, the reaction was poured into water and extracted with methylene chloride. The organic extracts were dried (MgSO$_4$) and evaporated under reduced pressure to give 38 mg of a white solid which was purified by preparative thin layer chromatography (SiO$_2$; 75/25 ethyl acetate/toluene) to give 21.0 mg of the desired sulfone: HRMS, m/e Calc'd. for $C_{19}H_{19}N_2O_3SF$: 374.1100; measured: 374.1125.

EXAMPLE 82

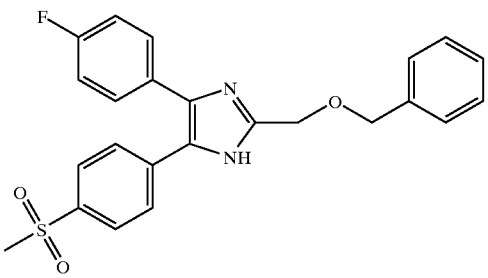

4-(4-Fluorophenyl)-5-[4-(methylsulfonyl)phenyl]-2-(phenyl-methoxymethyl)-1H-imidazole To a solution of 1-(1-ethoxyethyl)-4-(4-fluorophenyl)-5-[4-(methylthio)phenyl]-1H-imidazol-2-yl]-1H-imidazole-2-methanol (Example 79, Step 1) (220 mg; 0.56 mmol) in 2.2 ml of THF, at 25° C., was added 13.4 mg (0.56 mmol) of dry sodium hydride. After stirring at 25° C. for 15 minutes, 66 μl of benzylbromide (95.7 mg; 0.56 mmol) was added. After stirring at 25° C. for 24 hours, the reaction was diluted with ether and washed with water. The organic extracts were dried (MgSO$_4$), and evaporated to dryness under reduced pressure to provide 234 mg of material, which was purified by flash chromatography (SiO$_2$; 25% ethyl acetate/toluene) to give 90 mg of material containing the desired intermediate. This material was dissolved in 8 ml of methanol/THF (1.6:1). Oxone® (450 mg) was dissolved in 2 ml of water and added to this solution all at once. After stirring the reaction at 25° C. for 2 hours, the reaction was poured into water and extracted with methylene chloride. The organic extracts were dried (MgSO$_4$) and evaporated under reduced pressure to give 67 mg of a white solid which was further purified by preparative thin layer chromatography (SiO$_2$; 50% ethyl acetate/toluene) to give 48 mg of the desired sulfone: Anal. Calc'd. for C$_{24}$H$_{21}$FN$_2$O$_3$S+0.5 H$_2$O: C, 64.70; H, 4.98; N 6.29. Found: C, 64.75; H, 4.36; N, 6.00.

EXAMPLE 83

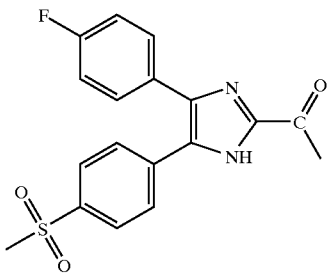

1-[4-(4-Fluorophenyl)-5-[4-(methylsulfonyl)phenyl]-1H-imidazol-2-yl] ethanone

To a solution of 1-(1-ethoxyethyl)-4-[4-fluorophenyl)-5-(4-(methyl-thio)phenyl]-1H-imidazole (Example 9, Step 2) (206 mg; 0.53 mmol) and tetramethylethylenediamine (TMEDA) (324 mg; 1.65 mmol) in 3.0 ml of THF at −78° C. was added 0.28 ml of a 2.5 M solution of n-butyllithium in hexanes. After stirring for 15 minutes, 66 μl of N,N-dimethylacetamide (62.7 mg; 0.72 mmol) was added. After 30 minutes, the solution was slowly warmed to 25° C., 2 ml of an aqueous solution of sodium bicarbonate was added, followed by dilution with 50 ml of diethyl ether. The solution was washed with 50 ml of a saturated solution of sodium bicarbonate and the organic extracts were dried (MgSO$_4$) and filtered. The solvent was removed under reduced pressure to give 230 mg of a yellow oil, which was purified by flash chromatography (SiO$_2$; 25% ethyl acetate/hexane) to yield 86 mg of slightly yellow oil (37%). This material was dissolved in 8 ml of methanol/THF (1.6:1). Oxone® (450 mg) was dissolved in 2 ml of water and this solution was added all at once. After stirring the reaction at 25° C. for 2 hours, the reaction was poured into water and extracted with methylene chloride. The organic extracts were dried (MgSO$_4$) and evaporated under reduced pressure to give a white solid which was purified by preparative thin-layer chromatography (SiO$_2$; 75% ethyl acetate/toluene) to give 56 mg of the desired sulfone: mp 215–217° C. Anal. Calc'd. for C$_{18}$H$_{15}$FN$_2$O$_3$S: C, 60.32; H, 4.22; N 7.82. Found: C, 60.09; H, 4.00; N, 7.76.

EXAMPLE 84

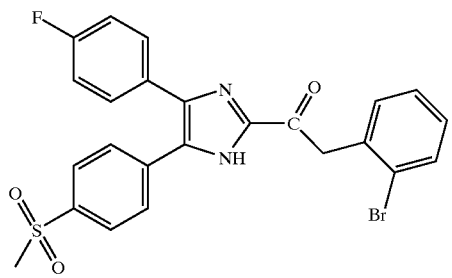

2-(2-Bromophenyl)-1-[4-(4-fluorophenyl)-5-[4-(methylsulfonyl)phenyl]-1H-imidazol-2-yl]ethanone Step 1 Preparation of 2-Bromo-N-methoxy-N-methylbenzene Acetamide To 2 g of 2-bromophenylacetic acid (9.3 mmol), in 33 ml of methylene chloride at 0° C., was added N,O-dimethylhydroxylamine hydrochloride (906.7 mg; 10.23 mmol), 4.26 ml of triethylamine (3.09 g; 30.6 mmol) and 2-chloromethylpyridinium iodide (2.6 g; 10.23 mmol). After stirring at 25° C. for 12 hours, the reaction mixture was poured into 250 ml of methylene chloride, then this solution was extracted with 150 ml of 1N hydrochloric acid, 150 ml saturated, aqueous solution of sodium bicarbonate, and 150 ml of brine. The organic extracts were dried (MgSO$_4$), filtered and evaporated under reduced pressure to give 1.98 g of a light pink oil, which was purified by flash chromatography (SiO$_2$; 25% ethyl acetate/ hexane) to give 849 mg of 2-bromo-N-methoxy-N-methylbenzene acetamide as an oil: Anal. Calc'd. for C$_{10}$H$_{12}$BrNO$_2$: C, 46.53; H, 4.69; N 5.43; Br 30.96. Found: C, 46.45; H, 4.71; N, 5.34; Br, 30.66.

Step 2 Preparation of 2-(2-Bromophenyl)-1-[4-(4-fluorophenyl)-5-[4-(methylsulfonyl)phenyl]-1H-imidazol-2-yl]ethanone To a solution of 1-(1-ethoxyethyl)-4-(4-fluorophenyl)-5-[4-(methyl-thio)phenyl]-1H-imidazole (Example 83 Step 1) (658.9 mg; 1.70 mmol) and TMEDA (639 mg; 5.4 mmol) in 10 ml of THF at −78° C. was added 0.91 ml of a 2.5 M n-butyllithium in hexanes. After stirring for 15 minutes, a solution of 2-bromo-N-methoxy-N-methylbenzene acetamide (step 1) (562.2 g; 2.29 mmol) in 1 ml of THF was added. The solution was warmed to 25° C. over 1 hour. The reaction was diluted with diethyl ether and washed with a saturated, aqueous, solution of sodium bicarbonate. The organic extracts were dried (MgSO$_4$), filtered and evaporated under reduced pressure to give a yellow oil, which was purified by flash chromatography (SiO$_2$; 50% ethyl acetate/hexane) to give 56 mg of a white foam. The foam (56 mg) was dissolved in 8 ml of methanol/THF (1.6:1). Oxone® (450 mg) was dissolved in 2 ml of water and this solution was added all at once. After stirring the reaction at 25° C. for 1.5 hours, the reaction was poured into water and extracted with methylene chloride. The organic extracts were dried (MgSO$_4$) and evaporated under reduced pressure to give a white solid which was purified by preparative thin layer chromatography (SiO$_2$; 75% ethyl acetate/toluene) to give 38 mg of the desired sulfone: Anal. Calc'd. for C$_{24}$H$_{18}$FN$_2$O$_3$SBr: C, 56.15; H, 3.53; N 5.46, Br, 15.56. Found: C, 56.23; H, 3.17; N, 5.26; Br; 15.74.

EXAMPLE 85

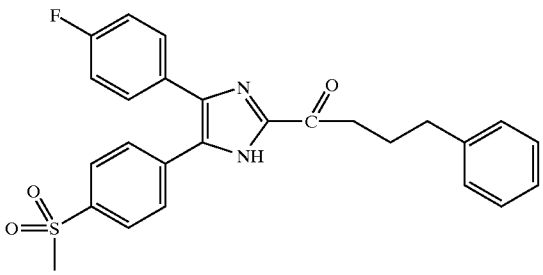

1-(4-(4-Fluorophenyl)-5-[4-methylsulfonyl)phenyl]-
1H-imidazol-2-yl]-3-phenyl-1-propanone Step 1 Preparation of N-Methoxy-N-methylbenzenepropaneamide To 1.39 g of dihydrocinnamic acid (9.3 mmol), in 33 ml of methylene chloride at 0° C., was added N,O-dimethylhydroxylamine hydrochloride (906.7 mg; 10.23 mmol), 4.26 ml of triethylamine (3.09 g; 30.6 mmol) and 2-chloromethylpyridinium iodide (2.6 g; 10.23 mmol). After stirring at 25° C. for 12 hours, the reaction mixture was poured into 250 ml of methylene chloride, then this solution was extracted with 150 ml of 1N hydrochloric acid, ml saturated, aqueous, solution of sodium bicarbonate with added sodium thiosulfate and 150 ml of brine. The organic extracts were dried ($MgSO_4$), filtered and evaporated under reduced pressure to give 1.3208 g of a light yellow oil, which was purified by flash chromatography ($SiO_2$; 50% ethyl acetate/hexane) to give 849 mg of N-methoxy-N-methylbenzenepropaneamide as an oil: Anal. Calc'd. for $C_{11}H_{15}NO_2$: C, 68.37; H, 7.82; N,7.25. Found: C, 68.60; H, 7.84; N,7.24.

Step 2 Preparation of 1-(4-(4-Fluorophenyl)-5-[4-methylsulfonyl)phenyl]-1H-imidazol-2-yl]-3-phenyl-1-propanone To a solution of 1-(1-ethoxyethyl)-4-(4-fluorophenyl)-5-[4-(methyl-thio)phenyl]-1H-imidazole (Example 83 Step 1) (503 mg; 1.30 mmol) and TMEDA (485 mg; 4.1 mmol) in 7.42 ml of THF at −78° C. was added 0.91 ml of a 2.5 M n-butyllithium in hexane. After stirring for 15 minutes, a solution of N-methoxy-N-methylbenzenepropaneamide (Step 1) (338.1; 1.75 mmol) in 1 ml of THF was added. The solution was warmed to 25° C. over a period of one hour. The reaction was diluted with diethyl ether and washed with a saturated, aqueous, solution of sodium bicarbonate. The organic extracts were dried ($MgSO_4$), filtered and evaporated under reduced pressure to give a yellow oil, which was purified by flash chromatography ($SiO_2$; 25% ethyl acetate/hexane) to give 515 mg of a colorless oil. The oil (100 mg) was dissolved in 8 ml of methanol/THF (1.6:1). Oxone® (450 mg) was dissolved in 2 ml of water and this solution was added all at once. After stirring the reaction at 25° C. for 1.5 hours, the reaction was poured into water and extracted with methylene chloride. The organic extracts were dried ($MgSO_4$) and evaporated under reduced pressure to give a white solid which was purified by preparative thin layer chromatography ($SiO_2$; 75% ethyl acetate/toluene) to give 51.5 mg of the desired sulfone: Mp 227–231° C.; Anal. Calc'd. for $C_{25}H_{21}FN_2O_3S$: C, 66.95; H, 4.72; N 6.25; S, 7.15. Found: C, 67.04; H, 4.58; N, 6.13; S, 7.24.

EXAMPLE 86

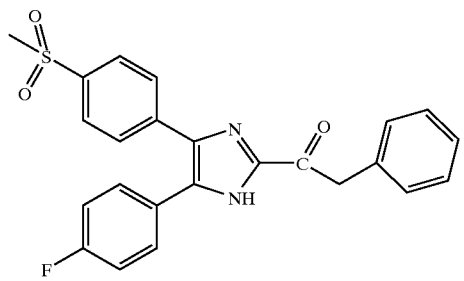

1-[5-(4-Fluorophenyl)-4-[4-(methylsulfonyl)phenyl]-
1H-imidazol-2-yl]-2-phenylethanone Step 1 Preparation of N-Methoxy-N-methylbenzeneacetamide To 1.26 g of phenylacetic acid, in 33 ml of methylene chloride at 0° C., was added N,O-dimethylhydroxylamine hydrochloride (906.7 mg; 10.23 mmol), 4.26 ml of triethylamine (3.09 g; 30.6 mmol) and 2-chloromethylpyridinium iodide (2.6 g; 10.23 mmol). After stirring at 25° C. for 12 hours, the reaction mixture was poured into 250 ml of methylene chloride, then this solution was extracted with 150 ml of 1N hydrochloric acid, 150 ml saturated, aqueous, solution of sodium bicarbonate, and 150 ml of brine. The organic extracts were dried ($MgSO_4$), filtered and evaporated under reduced pressure to give 1.98 g of a oil, which was purified by flash chromatography ($SiO_2$; 50% ethyl acetate/hexane) to give 1.1334 g of N-methoxy-N-methylbenzeneacetamide as an oil: Anal. Calc'd. for $C_{10}H_{13}NO_2+0.25 H_2O$: C, 65.38; H, 6.93; N 7.49. Found: C, 65.67; H, 6.93; N, 7.49.

Step 2 Preparation of 1-[5-(4-Fluorophenyl)-4-[4-(methylsulfonyl)phenyl]-1H-imidazol-2-yl]-2-phenylethanone To a solution of 1-(1-ethoxyethyl)-4-(4-fluorophenyl)-5-[4-(methyl-thio)phenyl]-1H-imidazole (Example 83 Step 1) (476 mg; 1.23 mmol) and TMEDA (462 mg; 3.97 mmol) in 7.0 ml of THF at −78° C. was added 0.66 ml of a 2.5 M n-butyllithium in hexanes. After stirring for 15 minutes, a solution of N-methoxy-N-methylbenzeneacetamide (338.1 mg; 1.75 mmol) in 1 ml of THF was added. The solution was warmed to 25° C. over 1 hour. The reaction was diluted with diethyl ether and washed with a saturated, aqueous, solution of sodium bicarbonate. The organic extracts were dried ($MgSO_4$), filtered and evaporated under reduced pressure to give a yellow oil, which was purified by flash chromatography ($SiO_2$; 25% ethyl acetate/hexane) to give 355 mg of a light yellow solid. This solid (100 mg) was dissolved in 8 ml of methanol/THF (1.6:1). Oxone® (450 mg) was dissolved in 2 ml of water and this solution was added all at once. After stirring the reaction at 25° C. for 1.5 hours, the reaction was poured into water and extracted with methylene chloride. The organic extracts were dried ($MgSO_4$) and evaporated under reduced pressure to give a white solid which was purified by flash chromatography ($SiO_2$; 25% ethyl acetate/toluene) to give 63 mg of the desired sulfone: mp 263.2° C.; Anal. Calc'd. for $C_{24}H_{19}FN_2O_3S$: C, 66.35; H, 4.41; N 6.45; S, 7.38. Found: C, 66.43; H, 4.26; N, 6.21; S, 7.12.

EXAMPLE 87

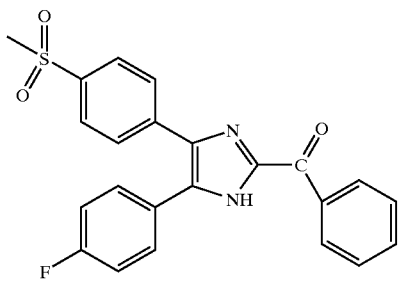

[5-(4-Fluorophenyl)-4-[4-(methylsulfonyl)phenyl]-1H-imidazol-2-yl]phenylmethanone Step 1 Preparation of N-Methoxy-N-methyl-benzenecarboxamide To 1.13 g of benzoic acid (9.3 mmol), in 33 ml of methylene chloride at 0° C., was added N,O-dimethylhydroxylamine hydrochloride (906.7 mg; 10.23 mmol), 4.26 ml of triethylamine (3.09 g; 30.6 mmol) and 2-chloromethylpyridinium iodide (2.6 g; 10.23 mmol). After stirring at 25° C. for 12 hours, the reaction mixture was poured into 250 ml of methylene chloride, then this solution was extracted with 150 ml of 1N hydrochloric acid, 150 ml saturated, aqueous solution of sodium bicarbonate, and 150 ml of brine. The organic extracts were dried ($MgSO_4$), filtered and evaporated under reduced pressure to give a oil, which was purified by flash chromatography ($SiO_2$; 50% ethyl acetate/hexane) to give 0.872 of N-methoxy-N-methyl-benzenecarboxamide as an oil: Anal. Calc'd. for $C_9H_{11}NO_2+0.25\ H_2O$: C, 63.70; H, 6.29; N 8.14. Found: C, 63.73; H, 6.83; N, 8.25

Step 2 Preparation of [5-(4-Fluorophenyl)-4-[4-(methylsulfonyl)phenyl]-1H-imidazol-2-yl]phenylmethanone To a solution of 1-(1-ethoxyethyl)-4-(4-fluorophenyl)-5-[4-(methyl-thio)phenyl]1H-imidazole (Example 83 Step 1) (374 mg; 0.96 mmol) and TMEDA (362 mg; 3.1 mmol) in 5.48 ml of THF at –780C was added 0.52 ml of a 2.5 M n-butyllithium in hexanes. After stirring for 15 minutes, a solution of N-methoxy-N-methyl-benzenecarboxamide (Step 1) (214 mg; 1.30 mmol) in 1 ml of THF was added. The solution was warmed to 25° C. over a period of one hour. The reaction was diluted with diethyl ether and washed with a saturated, aqueous solution of sodium bicarbonate. The organic extracts were dried ($MgSO_4$), filtered and evaporated under reduced pressure to give the crude product, which was purified by flash chromatography ($SiO_2$; 25% ethyl acetate/hexane) to give 294 mg of product. 133 mg of this material was dissolved in 8 ml of methanol/THF (1.6:1). Oxone® (450 mg) was dissolved in 2 ml of water and then this solution was added all at once. After stirring the reaction at 25° C. for 1.5 hours, the reaction was poured into water and extracted with methylene chloride. The organic extracts were dried ($MgSO_4$) and evaporated under reduced pressure to give a white solid which was purified by flash chromatography ($SiO_2$; 50% ethyl acetate/toluene) to give 49.5 mg of the desired sulfone: mp 2640 ° C. (dec.). Anal. Calc'd. for $C_{23}H_{17}FN_2O_3S$: C, 65.70; H, 4.08; N 6.66; S, 7.63. Found: C, 65.51; H, 4.34; N, 6.40; S, 7.68.

EXAMPLE 88

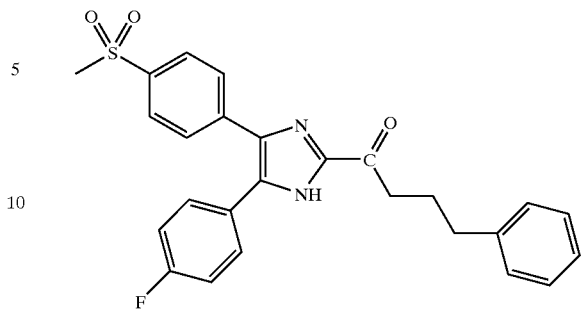

1-[5-(4-Fluorophenyl)-4-[4-(methylsulfonyl)phenyl]-1H-imidazol-2-yl]-4-phenyl-1-butanone Step 1 Preparation of N-Methoxy-N-methylbenzenebutanamide To 1.52 g of phenylbutyric acid (9.3 mmol), in 33 ml of methylene chloride at 0° C., was added N,O-dimethylhydroxylamine hydrochloride (906.7 mg; 10.23 mmol), 4.26 ml of triethylamine (3.09 g; 30.6 mmol) and 2-chloromethylpyridinium iodide (2.6 g; 10.23 mmol). After stirring at 25° C. for 12 hours, the reaction mixture was poured into 250 ml of methylene chloride, then this solution was extracted with 150 ml of 1N hydrochloric acid, 150 ml saturated, aqueous solution of sodium bicarbonate, and 150 ml of brine. The organic extracts were dried ($MgSO_4$), filtered and evaporated under reduced pressure to give an oil, which was purified by flash chromatography ($SiO_2$; 50% ethyl acetate/hexane) to give 0.525 g of N-methoxy-N-methylbenzenebutanamide: Anal. Calc'd. for $C_{12}H_{17}NO_2+0.15\ H_2O$: C, 68.64; H, 8.30; N 6.67. Found: C, 68.70; H, 7.96; N, 6.52.

Step 2 Preparation of 1-[5-(4-Fluorophenyl)-4-[4-(methylsulfonyl)phenyl]-1H-imidazol-2-yl]-4-phenyl-1-butanone To a solution of 1l(1-ethoxyethyl)-4-(4-fluorophenyl)-5-[4-(methyl-thio)phenyl]-1H-imidazole (Example 83 Step 1) (533 mg; 1.3 mmol) and TMEDA (491.56 mg; 4.21 mmol) in 7 ml of THF at –78° C. was added 0.70 ml of a 2.5 M n-butyllithium in hexanes. After stirring for 15 minutes, a solution of N-methoxy-N-methylbenzenebutanamide (Step 1)(363 mg; 1.75 mmol) in 1 ml of THF was added. The solution was warmed to 25° C. over 1 hour. The reaction was diluted with diethyl ether and washed with a saturated, aqueous solution of sodium bicarbonate. The organic extracts were dried ($MgSO_4$), filtered and evaporated under reduced pressure to give the crude product, which was purified by flash chromatography ($SiO_2$; 25% ethyl acetate/hexane) to give 229 mg of product. This material (74 mg) was dissolved in 8 ml of methanol/THF (1.6:1). Oxone® (450 mg) was dissolved in 2 ml of water and this solution was added all at once. After stirring the reaction at 25° C. for 1.5 hours, the reaction was poured into water and extracted with methylene chloride. The organic extracts were dried ($MgSO_4$) and evaporated under reduced pressure to give a white solid which was purified by flash chromatography ($SiO_2$; 50% ethyl acetate/toluene) to give 43 mg of the desired sulfone: Anal. Calc'd. for $C_{26}H_{23}FN_2O_3S+0.4\ H_2O$: C, 66.48; H, 5.11; N 5.96. Found: C, 66.65; H, 4.94; N, 5.81.

EXAMPLE 89

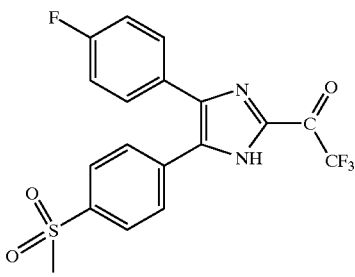

2,2,2-Trifluoro-1-[4-(4-fluorophenyl)-5-[4-methylsulfonyl)phenyl]-1H-imidazol-2-yl]ethanone Step 1 Preparation of 1-[1-(1-ethoxyethyl)-4-(4-fluorophenyl)-5-[4-(methylthio)phenyl]-1H-imidazol-2-yl]-2,2,2-trifluoroethanone To a solution of 1-(1-Ethoxyethyl)-4-(4-fluorophenyl)-5-[4-(methyl-thio)phenyl]-1H-imidazole (Example 83 Step 1) (403.8 mg; 1.04 mmol) and TMEDA (582.7 mg; 5.01 mmol) in 6 ml of THF at −78° C. was added 1.23 ml of 2.5 M n-butyllithium in hexanes. After stirring for 15 minutes, a solution of N-methoxy-N-methyltrifluoracetamide, (167 mg; 1.41 mmol) in 1 ml of THF was added. The solution was warmed to 25° C. over one hour. The reaction was diluted with diethyl ether and washed with a saturated, aqueous, solution of sodium bicarbonate. The organic extracts were dried ($MgSO_4$), filtered and evaporated under reduced pressure to give the crude product, which was purified by flash chromatography ($SiO_2$; 25% ethyl acetate/hexane) to give 81 mg of 1-[1-(1-ethoxyethyl)-4-(4-fluorophenyl)-5-[4-(methylthio)phenyl]-1H-imidazol-2-yl]-2,2,2-trifluoroethanone which was used directly in the next step.

Step 2 Preparation of 2,2,2-Trifluoro-1-[4-(4-fluorophenyl)-5-[4-methylsulfonyl)phenyl]-1H-imidazol-2-yl]ethanone 1-[1-(1-Ethoxyethyl)-4-(4-fluorophenyl)-5-[4-(methylthio)phenyl]-1H-imidazol-2-yl]-2,2,2-trifluoroethanone (Step 1) was dissolved in 8 ml of methanol/THF (1.6:1). Oxone® (450 mg) was dissolved in 2 ml of water and this solution was added all at once to methanol/THF solution. After stirring the reaction at 25° C. for 1.5 hours, the reaction was poured into water and extracted with methylene chloride. The organic extracts were dried ($MgSO_4$) and evaporated under reduced pressure to give a white solid which was purified by preparative thin layer chromatography ($SiO_2$; 50% ethyl acetate/toluene) to give 23 mg of the desired sulfone: mp 291.7° C. Anal. Calc'd. for $C_{18}H_{12}F_4N_2O_3S$: C, 52.43; H, 2.93; N 6.79. Found: C, 52.38; H, 2.96; N. 6.26.

EXAMPLE 90

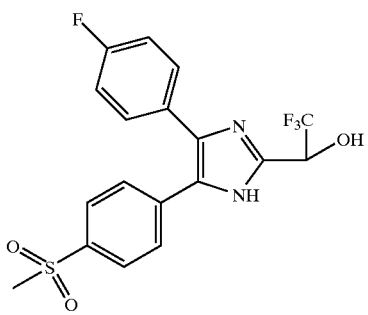

4-(4-Fluorophenyl)-5-(4-(methylsulfonyl)phenyl]-a-(trifluoromethyl)-1H-imidazole-2-methanol To a solution of 85 mg of 1-[1-(1-ethoxyethyl)-4-(4-fluorophenyl)-5-[4-(methylthio)phenyl]-1H-imidazol-2-yl]-2,2,2-trifluoroethanone (Example 89, Step 1) (0.18 mmol) in 1 ml of methanol at 0° C. was added 10 mg of sodium borohydride (0.26 mmol). The solution turned immediately from yellow to colorless. The reaction was quenched with 1% solution of aqueous hydrochloric acid and diluted with methylene chloride then washed with brine. The organic extracts were dried ($MgSO_4$), filtered and the solvent was removed under reduced pressure to provide 77.1 mg of a white film. All of this material was dissolved in 8 ml of methanol/THF (1.6:1). Oxone® (450 mg) was dissolved in 2 ml of water and the solution was added all at once. After stirring the reaction at 25° C. for 1.5 hours, the reaction was poured into water and extracted with methylene chloride. The organic extracts were dried ($MgSO_4$) and evaporated under reduced pressure to give a white foam which was purified by preparative thin layer chromatography ($SiO_2$; 100% ethyl acetate) to give 50.5 mg of the desired sulfone: mp 126–130° C. Anal. Calc'd. for $C_{18}H_{14}F_4N_2O_3S$: C, 51.49; H, 3.54; N 6.33. Found: C, 51.53; H, 3.26; N, 6.31.

EXAMPLE 91

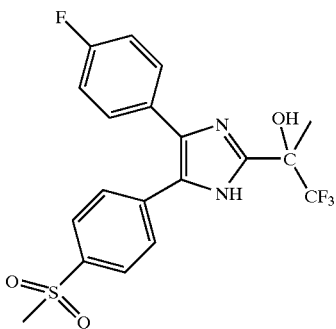

4-(4-Fluorophenyl)-α-methyl-5-[4-(methylsulfonyl)phenyl]-α-(trifluoromethyl)-1H-imidazole-2-methanol To a solution of 1-(1-ethoxyethyl)-4-(4-fluorophenyl)-5-[4-(methyl-thio)phenyl]-1H-imidazole (Example 83 Step 1) (346.6 mg; 0.89 mmol) and TMEDA (495.9 mg; 4.26 mmol) in 5.08 ml of THF, at −78° C., was added 0.48 ml of a 2.5

M n-butyllithium in hexanes. After stirring for 15 minutes, a solution of 1,1,1-trifluoroacetone (135.5 mg; 1.21 mmol) in 1 ml of THF was added. The solution was warmed to 25° C. over a period of one hour. The reaction was diluted with diethyl ether and washed with a saturated, aqueous, solution of sodium bicarbonate. The organic extracts were dried (MgSO$_4$), filtered and evaporated under reduced pressure to give the crude product, which was purified by flash chromatography (SiO$_2$; 50% ethyl acetate/hexane) to give 220 mg of a yellow oil. This material (100 mg) was dissolved in 8 ml of methanol/THF (1.6:1). Oxone® (450 mg) was dissolved in 2 ml of water and the solution was added all at once to the methanol/THF solution. After stirring the reaction at 25° C. for 1.5 hours, the reaction was poured into water and extracted with methylene chloride. The organic extracts were dried (MgSO$_4$) and evaporated under reduced pressure to give a white solid which was purified by preparative thin layer chromatography (SiO$_2$; 50% ethyl acetate/toluene) to give 40 mg of the desired sulfone: Anal. Calc'd. for C$_{19}$H$_{16}$F$_4$N$_2$O$_3$S: C, 53.27; H, 3.76; N 6.54. Found: C, 53.42; H, 3.73; N, 6.29.

EXAMPLE 92

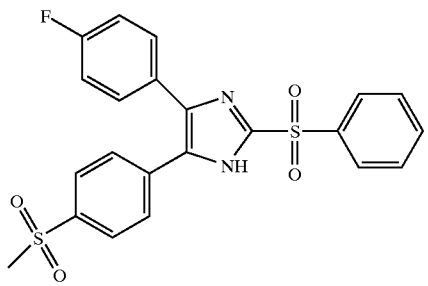

4-(4-Fluorophenyl)-5-[4-(methylsulfonyl)phenyl]-2-(phenyl-sulfonyl)-1H-imidazole To a solution of 1-(1-ethoxyethyl)-4-(4-fluorophenyl)-5-[4-(methyl-thio)phenyl]-1H-imidazole (Example 83 Step 1) (208 mg; 0.53 mmol) and TMEDA (76.3 mg; 0.23 mmol) in 3.02 ml of THF, under an argon atmosphere at −78° C., was added 0.21 ml of a 2.5 M n-butyllithium in hexanes. After stirring for 15 minutes, N-fluorodibenzene sulfonamide (167 mg; 0.53 mmol) was added and the reaction was slowly warmed to 25° C. The reaction was quenched with 1–2 ml of an aqueous, saturated solution of sodium bicarbonate, diluted with ether and washed with additional saturated, sodium bicarbonate solution. The organic extracts were dried (MgSO$_4$), filtered and evaporated under reduced pressure to give a yellow foam, which was purified by flash chromatography (SiO$_2$; 25% ethyl acetate/hexane) to give 179.9 mg of a yellow foam. The foam (90 mg) was dissolved in 8 ml of methanol/THF (1.6:1). Oxone® (450 mg) was dissolved in 2 ml of water and the solution was added all at once. After stirring the reaction at 25° C. for 1.5 hours, the reaction was poured into water and extracted with methylene chloride. The organic-extracts were dried (MgSO$_4$) and evaporated under reduced pressure to give product which was purified by flash chromatography (SiO$_2$; 5% ethanol/methylene chloride) to give 86 mg of the unexpected sulfone: Anal. Calc'd. for C$_{22}$H$_{17}$FN$_2$O$_4$S$_2$: C, 45.71; H, 3.20; N 4.44; S, 20.34. Found: C, 45.55; H, 2.95; N, 4.33; S, 20.49.

EXAMPLE 93

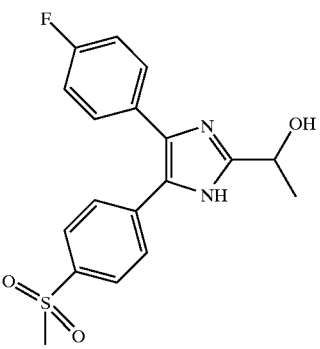

4-(4-Fluorophenyl)-α-methyl-5-[4-(methylsulfonyl)phenyl]-1H-imidazole-2-methanol Step 1 Preparation of 1-[(1-Ethoxyethyl)-4-(4-fluorophenyl)-5-[4-(methylthio)phenyl]-1H-imidazol-2-yl]ethanone To a solution of 1-(1-ethoxyethyl)-4-(4-fluorophenyl)-5-[4-(methylthio)phenyl]-1H-imidazole (Example 9, Step 2) (206 mg; 0.53 mmol) and TMEDA (324 mg; 1.65 mmol) in 3.0 mL of THF at −78° C. was added 0.28 ml of a 2.5 M solution of n-butyllithium in hexanes. After stirring for 15 minutes, 66 ml of N,N-dimethylacetamide (62.7 mg; 0.72 mmol) was added. After 30 minutes, the solution was slowly warmed to 25° C., then 2 ml of an aqueous solution of sodium bicarbonate was added, followed by dilution with 50 mL of diethyl ether. The solution was washed with 50 ml of a saturated solution of sodium bicarbonate and the organic extracts were dried (MgSO$_4$) and filtered. The solvent was removed under reduced pressure to give 230 mg of a yellow oil, which was purified by flash chromatography (SiO$_2$; 25% ethyl acetate/hexane) to yield 86 mg of the protected ketone as a slightly yellow oil (37%).

Step 2 Preparation of 1-[(1-Ethoxyethyl)-4-(4-fluorophenyl)-5-[4-(methylthio)phenyl]-1H-imidazol-2-yl]ethanol To a solution of 1-[(1-ethoxyethyl)-4-(4-fluorophenyl)-5-[4-(methylthio)phenyl]-1H-imidazol-2-yl]ethanone (Step 1) (1.08 g.; 2.9 mmol) at 25° C. was added sodium borohydride (109.7 mg; 2.9 mmol). After stirring for 20 hours, the reaction mixture was cooled to 0° C. and 50 ml of a 1% aqueous solution of hydrochloric acid was added. This solution was saturated with solid sodium chloride and extracted with 100 ml, then 2×50 ml of methylene chloride. The organics were combined then washed with 50 ml of a saturated, aqueous solution of sodium bicarbonate. The organic extracts were dried (MgSO$_4$), filtered and evaporated under reduced pressure to provide 1.06 g of a light yellow foam, which was purified by flash chromatography (SiO$_2$, 75% ethyl acetate/hexane) to provide 907 mg of the desired protected alcohol.

Step 3 Preparation of 4-(4-Fluorophenyl)-α-methyl-5-[4-(methylsulfonyl)phenyl]-1H-imidazole-2-methanol The protected alcohol (Step 2) (400 mg) was dissolved in 8 ml of methanol/THF (1.6:1). Oxone® (450 mg) was dissolved in 2 ml of water and the solution was added all at once. After stirring the reaction at 25° C. for 1.5 hours, the reaction was poured into 150 ml of water and extracted with 30 ml of methylene chloride several times. The organic extracts were dried (MgSO$_4$) and evaporated under reduced pressure to give 40 mg of crude product which was purified by preparative thin layer chromatography (SiO$_2$; 100% ethyl acetate) to give 14 mg of the sulfone: HRMS, m/e Calc'd. for $C_{18}H_{17}N_2O_3SF$: 360.0940; measured: 360.0977.

EXAMPLE 94

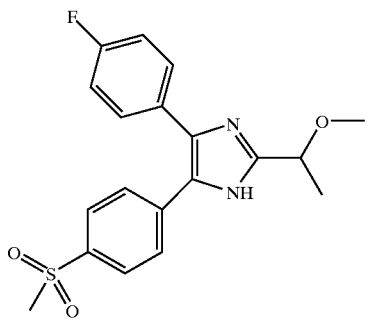

4-(4-Fluorophenyl)-2-(1-methoxyethyl)-5-[4-(methyl-sulfonyl)phenyl]-1H-imidazole To a solution of 1-[(1-ethoxyethyl)-4-(4-fluorophenyl)-5-(4-(methylthio)phenyl]-1H-imidazol-2-yl]ethanol (Example 93, Step 2) (410 mg; 1.05 mmol) in 4.2 ml of DMF was added 36 mg of sodium hydride (60 wt % oil dispersion). After stirring at 25° C. for 15 minutes, 65.4 µl of methyl iodide was added. Stirring continued at 25° C. for 12 hours, then the reaction was heated to 36° C. for 8 hours, then poured into ethyl acetate and extracted with brine. The organic extracts were dried ($MgSO_4$), filtered and the solvent was removed under reduced pressure to provide an oil which was purified by medium pressure chromatography ($SiO_2$; 50% ethyl acetate/hexane) to provide 133 mg of an oil. The alcohol was dissolved in 8 ml of methanol/THF (1.6:1). Oxone® (450 mg) was dissolved in 2 ml of water and the solution was added all at once to the methanol/THF solution. After stirring the reaction at 25° C. for 1.5 hours, the reaction was poured into water and extracted with methylene chloride. The organic extracts were dried ($MgSO_4$) and evaporated under reduced pressure to give the crude product which was purified by preparative thin layer chromatography ($SiO_2$; 100% ethyl acetate) to give 66 mg of the desired sulfone: mp 212° C. Anal. Calc'd. for $C_{19}H_{19}N_2O_3SF$: C, 60.95; H, 5.11; N 7.48; S, 8.56. Found: C, 61.24; H, 5.00; N, 7.45; S, 8.51.

EXAMPLE 95

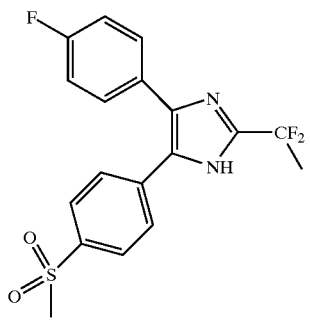

2-(1,1-Difluoroethyl)-4-(4-fluorophenyl)-5-[4-(methyl-sulfonyl)phenyl]-1H-imidazole
Step 1 Preparation of 5-(4-Fluorophenyl)-2-(2-methyl-1,3-dithian-2-yl)-4-[4-methylthio)phenyl]-1H-imidazole To a suspension of 1-[(1-ethoxyethyl)-4-(4-fluorophenyl)-5-[4-(methylthio)phenyl]-1H-imidazol-2-yl]ethanone (Example 93, Step 1) (797 mg; 2.12 mmol) in 0.42 ml of 1,3-propanedithiol in a 1 ml flask, at 25° C., under argon was added 0.88 ml of boron trifluoride acetic acid-complex. After stirring for 12–18 hours the reaction was slowly quenched with 8 ml of a saturated, solution of sodium bicarbonate then diluted with 8 ml of ethyl acetate. The organic extracts were diluted with additional ethyl acetate and then washed with a 1N solution of aqueous sodium hydroxide and brine. The organic extracts were dried ($MgSO_4$), filtered and the solvent was removed under reduced pressure to provide 542 mg of a solid which was washed with 25% ethyl acetate/hexane to provide 536.8 mg of 5-(4-fluorophenyl)-2-(2-methyl-1,3-dithian-2-yl)-4-[4-methylthio)phenyl]-1H-imidazole which was used in the following step without further purification: mp 164–168° C.
Step 2 Preparation of 2-(1,1-Difluoroethyl)-4-(4-fluorophenyl)-5-[4-(methyl-sulfonyl)phenyl]-1H-imidazole A solution of 5-(4-fluorophenyl)-2-(2-methyl-1,3-dithian-2-yl)-4-[4-methylthio)phenyl]-1H-imidazole (Step 1) (268.40 mg; 0.64 mmol) was prepared by sonicating a suspension of this material in 2 ml of methylene chloride then heated in a hot water bath till the compound dissolved. N-iodosuccinimide (863.9 mg; 3.84 ml) was suspended in 7.8 ml of anhydrous methylene chloride in a separate flask, under an atmosphere of argon, cooled to −30° C. and 0.43 ml of HF-pyridine (70%) was added to the cooled suspension. Immediately the solution of 5-(4-fluorophenyl)-2-(2-methyl-1,3-dithian-2-yl)-4-[4-methylthio)phenyl]-1H-imidazole was added and the resulting solution turned purple instantaneously. After maintaining the temperature between −27° C. and −40° C. for 2.5 hours, the reaction mixture was diluted with a saturated, aqueous, solution of sodium bicarbonate and additional methylene chloride. A spatula tip of solid sodium thiosulfate was added. After carefully shaking the two phase mixture the color disappeared. The organic extracts were dried ($MgSO_4$), filtered and the solvent was removed under reduced pressure to provide 309 mg of a yellow oil which solidified upon storage in the refrigerator overnight. The yellow brown solid was suspended in heptane and the solvent was removed under reduced pressure. This step was repeated twice which resulted in 242 mg of a yellow powder. This material (214 mg) was dissolved in 8 ml of methanol/THF (1.6:1). Oxone® (450 mg) was dissolved in 2.5 ml of water and then this solution was added all at once. After stirring the reaction at 25° C. for 1.25 hours, the reaction was poured into water and extracted with methylene chloride. The organic extracts were dried ($MgSO_4$) and evaporated under reduced pressure to give the crude product which was purified by flash chromatography ($SiO_2$; 50% ethyl acetate/ hexane) to give 57.4 mg of the desired sulfone: mp 211° C.; Anal. Calc'd. for $C_{18}H_{15}F_3N_2O_2S$: C, 45.71; H, 3.20; N 4.44; S, 20.34. Found: C, 45.55; H, 2.95; N, 4.33; S, 20.49.

BIOLOGICAL EVALUATION
Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 ml) with compounds suspended in vehicle containing 0.5% methylcellulose and 0.025% surfactant, or with vehicle alone. One hour later a subplantar injection of 0.1 ml of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the. percentage inhibition of edema was determined (Otterness and Bliven, Laboratory Models for Testing NSAIDs, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Example | RAT PAW EDEMA % Inhibition[1] | ANALGESIA % Inhibition[1] |
|---|---|---|
| 1 | 22 | 25 |
| 58 | 14 | |
| 70 | 27 | 29* |

*50 mg/kg body weight
[1]@ 30 mg/kg body weight

Evaluation of COX I and COX II Activity In Vitro

The compounds of this invention exhibited inhibition in vitro of COX II. The COX II inhibition activity of the compounds of this invention illustrated in the Examples was determined by the following methods.

a. Preparation of Recombinant COX Baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7–10E8 pfu/ml), stocks of virus were prepared. For large scale production, SF9 insect cells were infected in 10 liter fermentors (0.5×10⁶/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II Activity:

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II

| Example | Human COX II $ID_{50}$ μM | Human COX I $ID_{50}$ μM |
|---|---|---|
| 1 | 0.2 | >100 |
| 2 | 0.2 | >100 |
| 3 | 0.2 | 2.2 |
| 4 | 0.5 | >100 |
| 5 | 1.2 | >100 |
| 6 | 4.6 | >100 |
| 7 | 4.8 | >100 |
| 8 | >0.1 | 2.1 |
| 9 | 5.1 | >100 |
| 10 | 1.2 | 63.5 |
| 11 | 0.4 | 10.4 |
| 12 | 1.3 | >100 |
| 13 | >0.1 | 9.6 |
| 14 | 0.6 | 2.0 |
| 15 | 2.9 | 5.6 |
| 16 | 0.6 | 20 |
| 17 | 0.3 | >100 |
| 18 | 0.2 | >100 |
| 19 | 0.5 | >100 |
| 20 | 40.7 | >100 |
| 21 | >0.1 | 10.8 |
| 44 | 12.8 | >100 |
| 47 | 0.1 | 12.9 |
| 48 | 8.7 | >100 |
| 49 | 55 | 10.8 |
| 50 | 1.5 | >100 |
| 51 | 1.7 | >100 |
| 55 | 0.3 | >100 |
| 58 | 0.2 | >100 |
| 60 | 0.1 | 6.2 |
| 62 | 2.4 | >100 |
| 63 | 1.3 | >100 |
| 70 | 1.4 | >100 |
| 72 | 3.0 | >100 |
| 79 | 8.3 | >100 |
| 80 | 2.9 | >100 |
| 81 | 3.3 | 77 |
| 82 | 0.7 | >100 |
| 83 | 4.3 | >100 |
| 85 | 0.4 | >100 |
| 89 | 5.3 | >100 |
| 90 | 3.9 | >100 |
| 91 | 5.9 | >100 |
| 92 | 3.0 | >100 |
| 94 | 6.4 | >100 |
| 95 | 2.4 | >100 |

Biological paradigms for testing the cytokine-inhibiting activity of these compounds are found in WO 95/13067, published May 18, 1995.

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of the formula:

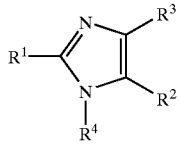

or a pharmaceutically acceptable salt thereof wherein
$R^1$ is haloalkyl, aralkylthio, aralkoxy, heteroarylthio, heteroaralkylthio, aryloxyalkyl, arylsulfonyl, arylcarbonyl, aralkylcarbonyl, aralkenyl, N-arylaminoalkyl, aminoalkyl, alkylaminoalkyl, N-arylaminoalkyl, aralkyl, N-alkyl-N-arylaminoalkyl, heteroaralkoxyalkyl, heteroaryloxyalkyl, heteroarylthioalkyl, heteroaralkyl, heteroarylalkylthioalkyl, heteroaralkoxy, heteroaryloxy, aralkylthio, arylthioalkyl, arylsulfonyl, aralkylsulfonyl, heteroarylsulfonyl, heteroarylalkylsulfonyl, arylthio, aryloxy, aralkylthioalkyl, aralkoxyalkyl, alkoxyaralkoxyalkyl, aryl or heteroaryl, wherein the aryl and heteroaryl radicals independently are substituted or unsubstituted at a substitutable position with one or more radicals selected from halo, alkylthio, alkylsulfinyl, alkyl, cyano, haloalkyl, hydroxyl, alkoxy, hydroxyalkyl and haloalkoxy;

$R^2$ and $R^3$ are independently selected from cycloalkyl, cycloalkenyl, heterocyclo and aryl, wherein the cycloalkyl, cycloalkenyl, heterocyclo and aryl radicals independently are substituted with one or more radicals selected from hydrido, halo, alkylthio, alkylsulfinyl, alkylsulfonyl, aminosulfonyl, haloalkylsulfonyl, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro; and $R^4$ is hydrido, alkyl or acyl;

provided that at least one of $R^2$ and $R^3$ is phenyl substituted with a radical selected from alkylsulfonyl and aminosulfonyl.

2. Compound of claim 1 wherein $R^1$ is selected from lower haloalkyl, lower aralkyl, lower heteroaralkyl, lower arylsulfonyl, lower arylcarbonyl, lower aralkylcarbonyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are unsubstituted or substituted at a substitutable position with one or more radicals independently selected from halo, lower alkylthio, lower alkylsulfinyl, lower alkyl, cyano, lower haloalkyl, lower hydroxyl, lower alkoxy, lower hydroxyalkyl and lower haloalkoxy;

$R^2$ and $R^3$ are independently selected from heteroaryl, lower cycloalkyl, lower cycloalkenyl, and aryl, wherein the heteroaryl, lower cycloalkyl, lower cycloalkenyl, and aryl radicals are substituted with one or more radicals independently selected from hydrido, halo, lower alkylthio, lower alkylsulfinyl, lower alkylsulfonyl, aminosulfonyl, lower haloalkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and $R^4$ is selected from hydrido, lower alkyl and acyl;

or a pharmaceutically acceptable salt thereof.

3. Compound of claim 2 wherein $R^1$ is selected from lower haloalkyl, phenylcarbonyl, lower aralkylcarbonyl, lower aralkenyl, lower aryloxyalkyl, lower aralkyloxyalkyl, lower arylsulfonyl, lower aralkylsulfonyl, lower arylthioalkyl, lower heteroarylalkylthioalkyl, and heteroaryl selected from 2-thienyl, 2-furyl, 3-furyl, 2-pyridyl, 4-pyridyl and 2-benzofuryl;

$R^2$ and $R^3$ are independently selected from heteroaryl, cycloalkyl and aryl, wherein the heteroaryl, cycloalkyl and aryl radicals are substituted at a substitutable position with one or more radicals independently selected from hydrido, halo, lower alkylthio, lower alkylsulfinyl, lower alkylsulfonyl, aminosulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, phenylamino and nitro; and wherein $R^4$ is selected from hydrido, lower alkyl and acyl; or a pharmaceutically-acceptable salt thereof.

4. Compound of claim 3 wherein $R^1$ is selected from trifluoromethyl, phenylcarbonyl, benzylcarbonyl, phenylethylcabonyl, phenylpropylcarbonyl, 2-bromobenzylcarbonyl, 2-phenylethenyl, phenoxymethyl, benzyloxymethyl, phenylthiomethyl, quinolylmethylthiomethyl, phenylsulfonyl, benzylsulfonyl, 3-furyl, 2-furyl, or 2-benzofuryl;

$R^2$ and $R^3$ are independently selected from phenyl, naphthyl, biphenyl, cyclobutyl, cyclopentyl, cyclohexyl, cycloheptyl, cyclohexenyl, benzofuryl, benzodioxolyl, furyl, imidazolyl, thienyl, thiazolyl, pyrrolyl, oxazolyl, isoxazolyl, triazolyl, pyrimidinyl, quinolinyl, benzimidazolyl, indolyl, pyrazolyl and pyridyl, wherein $R^2$ and $R^3$ are substituted at a substitutable position with one or more radicals independently selected from hydrido, fluoro, chloro, bromo, iodo, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methylsulfonyl, aminosulfonyl, cyano, methoxy, ethoxy, isopropoxy, tert-butoxy, propoxy, butoxy, isobutoxy, pentoxy, methylenedioxy, amino, trifluoromethoxy, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, hydroxyl, nitro, methylsulfinyl, butylsulfinyl, hydroxymethyl, methoxymethyl, ethoxymethyl, methylamino, N,N-dimethylamino, phenylamino, methylthio, ethylthio, propylthio and butylthio;

and wherein $R^4$ is selected from methyl, ethyl, hydrido, methylcarbonyl and trifluoromethylcarbonyl;

or a pharmaceutically-acceptable salt thereof.

5. Compound of claim 4 selected from compounds, and their pharmaceutically acceptable salts, of the group consisting of 5-(3-chlorophenyl)-4-(4-methylsulfonylphenyl)-2-trifluoromethyl-1H-imidazole;

5-(3-chloro-4-methylphenyl)-4-(4-methylsulfonylphenyl)-2-trifluoromethyl-1H-imidazole;

5-(3-fluorophenyl)-4-(4-methylsulfonylphenyl)-2-trifluoromethyl-1H-imidazole;

5-(3-chloro-4-methoxyphenyl)-4-(4-methylsulfonylphenyl)-2-trifluoromethyl-1H-imidazole;

5-(4-fluorophenyl)-4-(4-methylsulfonylphenyl)-2-trifluoromethyl-1H-imidazole;

5-(4-fluorophenyl)-4-(4-methylsulfonylphenyl)-2-phenoxymethyl-1H-imidazole;

5-(4-fluorophenyl)-4-(4-methylsulfonylphenyl)-2-(2-phenyl-trans-eth-1-ene)-1H-imidazole;

2-(2-benzofuryl)-5-(4-fluorophenyl)-4-(4-methylsulfonylphenyl)-1H-imidazole;

5-(4-fluorophenyl)-2-(2-furyl)-4-(4-methylsulfonylphenyl)-1H-imidazole;

2-benzylthio-5-(4-fluorophenyl)-4-[4-(methylsulfonyl)phenyl]imidazole;

5-(3-fluoro-4-methoxyphenyl)-4-[4-(methylsulfonyl)phenyl]-2-(trifluoromethyl)-1H-imidazole;

5-(4-chlorophenyl)-4-[4-(methylsulfonyl)phenyl]-2-(trifluoromethyl)-1H-imidazole;

5-(2-chlorophenyl)-4-[4-(methylsulfonyl)phenyl]-2-(trifluoromethyl)-1H-imidazole;

5-(3,4-dichlorophenyl)-4-[4-(methylsulfonyl)phenyl]-2-(trifluoromethyl)-1H-imidazole;

4-[4-(methylsulfonyl)phenyl]-5-(2-naphthyl)-2-(trifluoromethyl)-1H-imidazole;

5-(4-methoxyphenyl)-4-[4-(methylsulfonyl)phenyl]-2-(trifluoromethyl)-1H-imidazole;

5-(4-methylphenyl)-4-[4-(methylsulfonyl)phenyl]-2-(trifluoromethyl)-1H-imidazole;

5-(2,4-difluorophenyl)-4-[4-(methylsulfonyl)phenyl]-2-(trifluoromethyl)-1H-imidazole;

5-(3,4-difluorophenyl)-4-[4-(methylsulfonyl)phenyl]-2-(trifluoromethyl)-1H-imidazole;

4-[4-(methylsulfonyl)phenyl]-5-phenyl-2-(trifluoromethyl)-1H-imidazole;

5-(4-fluorophenyl)-2-(3-furyl)-4-(4-methylsulfonylphenyl)-1H-imidazole;

4-[5-(4-fluorophenyl)-2-(trifluoromethyl)-1H-imidazol-4-yl]benzenesulfonamide;

4-[5-(4-fluorophenyl)-2-phenoxymethyl-1H-imidazol-4-yl]benzenesulfonamide;

4-[5-(4-fluorophenyl)-2-(2-phenyl-trans-eth-1-ene)-1H-imidazol-4-yl]benzenesulfonamide;

4-[2-(2-benzofuryl)-5-(4-fluorophenyl)-1H-imidazol-4-yl]benzenesulfonamide;

4-[5-(4-fluorophenyl)-2-(2-furyl)-1H-imidazol-4-yl]benzenesulfonamide;

4-[2-benzylthio-5-(4-fluorophenyl)-1H-imidazol-4-yl]benzenesulfonamide;

4-[5-(3-fluoro-4-methoxyphenyl)-2-(trifluoromethyl)-1H-imidazol-4-yl]benzenesulfonamide;

4-[5-(4-chlorophenyl)-2-(trifluoromethyl)-1H-imidazol-4-yl]benzenesulfonamide;

4-[5-(2-chlorophenyl)-2-(trifluoromethyl)-1H-imidazol-4-yl]benzenesulfonamide;

4-[5-(3,4-dichlorophenyl)-2-(trifluoromethyl)-1H-imidazol-4-yl]benzenesulfonamide;

4-[5-(2-naphthyl)-2-(trifluoromethyl)-1H-imidazol-4-yl]benzenesulfonamide;

4-[5-(4-methoxyphenyl)-2-(trifluoromethyl)-1H-imidazol-4-yl]benzenesulfonamide;

4-[5-(4-methylphenyl)-2-(trifluoromethyl)-1H-imidazol-4-yl]benzenesulfonamide;

4-[5-(2,4-difluorophenyl)-2-(trifluoromethyl)-1H-imidazol-4-yl]benzenesulfonamide;

4-[5-(3,4-difluorophenyl)-2-(trifluoromethyl)-1H-imidazol-4-yl]benzenesulfonamide;

4-[5-phenyl-2-(trifluoromethyl)-1H-imidazol-4-yl]benzenesulfonamide;

4-[5-(4-fluorophenyl)-2-(3-furyl)-1H-imidazol-4-yl]benzenesulfonamide;

4-(3,4-dimethyoxyphenyl)-5-[4-(methylsulfonyl)phenyl]-2-(trifluoromethyl)-1H-imidazole;

4-(4-methoxy-3-methylphenyl)-5-[4-(methylsulfonyl)phenyl]-2-(trifluoromethyl)-1H-imidazole;

5-(4-fluorophenyl)-1-methyl-4-[4-(methylsulfonyl)phenyl]-2-(trifluoromethyl)-1H-imidazole;

4-(4-fluorophenyl)-1-methyl-5-[4-(methylsulfonyl)phenyl]-2-(trifluoromethyl)-1H-imidazole;

5-(3,5-dimethylphenyl)-4-[4-(methylsulfonyl)phenyl]-2-(trifluoromethyl)-1H-imidazole;

5-(5-bromothien-2-yl)-4-[4-(methylsulfonyl)phenyl]-2-(trifluoromethyl)-1H-imidazole;

N,N-dimethyl-4-[4-[4-(methylsulfonyl)phenyl]-2-(trifluoromethyl)-1H-imidazol-5-yl]benzenamine;

2-[[[4-(4-fluorophenyl)-5-[4-(methylsulfonyl)phenyl]-1H-imidazol-2-yl]thio]methyl]quinoline;

4-(4-fluorophenyl)-5-[4-(methylsulfonyl)phenyl]-2-[(phenylmethyl)sulfonyl]-1H-imidazole;

5-(3,5-dimethyl-4-methoxyphenyl)-4-[4-(methylsulfonyl)phenyl]-2-(trifluoromethyl)-1H-imidazole;

5-[3-fluoro-4-(methylthio)phenyl]-4-[4-(methylsulfonyl)phenyl]-2-(trifluoromethyl)-1H-imidazole;

5-(3-chloro-5-methylphenyl)-4-[4-(methylsulfonyl)phenyl]-2-(trifluoromethyl)-1H-imidazole;

5-[3-chloro-4-(methylthio)phenyl]-4-[4-(methylsulfonyl)phenyl]-2-(trifluoromethyl)-1H-imidazole;

5-(3-fluoro-4-methylphenyl)-4-[4-(methylsulfonyl)phenyl]-2-(trifluoromethyl)-1H-imidazole;

1-[5-(3-chloro-5-methylphenyl)-4-[4-(methylsulfonyl)phenyl]-2-(trifluoromethyl)-1H-imidazol-1-yl]ethanone;

5-(3-methylphenyl)-4-[4-(methylsulfonyl)phenyl]-2-trifluoromethyl-1H-imidazole;

5-(3-methylphenyl)-4-[4-(sulfonamido)phenyl]-2-trifluoromethyl-1H-imidazole;

5-(3,4-dimethylphenyl)-4-[4-(methylthio)phenyl]-2-(trifluoromethyl)-1H-imidazole;

4-[4-(methylsulfonyl)phenyl]-5-(3-pyridyl)-2-(trifluoromethyl)-1H-imidazole;

5-(3-cyanophenyl)-4-[4-(methylthio)phenyl]-2-(trifluoromethyl)-1H-imidazole;

5-(2-fluorophenyl)-4-[4-(methylsulfonyl)phenyl]-2-(trifluoromethyl)-1H-imidazole;

5-(3-methoxyphenyl)-4-[4-(methylsulfonyl)phenyl]-2-(trifluoromethyl)-1H-imidazole;

5-(2-methylphenyl)-4-[4-(methylsulfonyl)phenyl]-2-(trifluoromethyl)-1H-imidazole;

5-(cyclohexyl)-4-[4-(methylsulfonyl)phenyl]-2-(trifluoromethyl)-1H-imidazole;

4-[4-(methylsulfonyl)phenyl]-5-(2-thiophenyl)-2-(trifluoromethyl)-1H-imidazole;

5-(4-chloro-3-methylphenyl)-4-[4-(methylsulfonyl)phenyl]-2-(trifluoromethyl)-1H-imidazole;

5-(4-cycloheptyl)-4-[4-(methylsulfonyl)phenyl]-2-(trifluoromethyl)-1H-imidazole;

5-(4-fluoro-3-methylphenyl)-4-[4-(methylsulfonyl)phenyl]-2-(trifluoromethyl)-1H-imidazole;

5-(cyclopentyl)-4-[4-(methylsulfonyl)phenyl]-2-(trifluoromethyl)-1H-imidazole;

4-[4-(methylsulfonyl)phenyl]-5-(3-thiophenyl)-2-(trifluoromethyl)-1H-imidazole;

5-(3-flouro-2-methylphenyl)-4-[4-(methylsulfonyl)phenyl]-2-(trifluoromethyl)-1H-imidazole;

5-(4-chloro-3-methoxyphenyl)-4-[4-(methylsulfonyl)phenyl]-2-(trifluoromethyl)-1H-imidazole;

[5-(4-fluorophenyl)-4-[4-(methylsulfonyl)phenyl]-1H-imidazol-2-yl]phenylmethanone;

1-[5-(4-fluorophenyl)-4-[4-(methylsulfonyl)phenyl]-1H-imidazol-2-yl]-4-phenyl-1-butanone;

2,2,2-trifluoro-1-[4-(4-fluorophenyl)-5-[4-methylsulfonyl)phenyl]-1H-imidazol-2-yl]ethanone;

4-(4-fluorophenyl)-5-[4-(methylsulfonyl)phenyl]-2-(phenylsulfonyl)-1H-imidazole; and 2-(1,1-difluoroethyl)-4-(4-fluorophenyl)-5-[4-(methylsulfonyl)phenyl]-1H-imidazole.

6. A compound of the formula

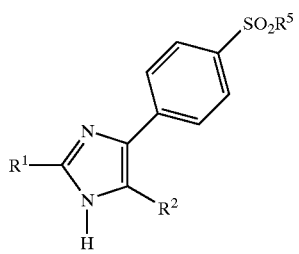

wherein $R^1$ is selected from lower haloalkyl, lower aralkyl, lower heteroaralkyl, lower arylsulfonyl, lower arylcarbonyl, lower aralkylcarbonyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are unsubstituted or substituted at a substitutable position with one or more radicals independently selected from halo, lower alkylthio, lower alkylsulfinyl, lower alkyl, cyano, lower haloalkyl, lower hydroxyl, lower alkoxy, lower hydroxyalkyl and lower haloalkoxy;

$R^2$ is selected from heteroaryl, lower cycloalkyl, lower cycloalkenyl, and aryl, wherein the heteroaryl, lower cycloalkyl, lower cycloalkenyl, and aryl radicals are substituted with one or more radicals independently selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro;

and $R^5$ is selected from lower alkyl and amino; or a pharmaceutically-acceptable salt thereof.

7. Compound of claim 6 wherein $R^1$ is lower haloalkyl, or $R_1$ is selected from phenylcarbonyl, lower aralkylcarbonyl, lower aralkenyl, lower aryloxyalkyl, lower aralkyloxyalkyl, lower arylsulfonyl, lower aralkylsulfonyl, lower arylthioalkyl, lower heteroarylalkylthioalkyl, and heteroaryl selected from 2-thienyl, 2-furyl, 3-furyl, 2-pyridyl, 4-pyridyl and 2-benzofuryl, each of which is unsubstituted or substituted with one or more groups independently selected from halo, lower alkyl thio, lower alkylsulfinyl, lower alkyl, cyano, lower haloalkyl, hydroxyl, lower alkoxy, lower hydroxyalkyl, and lower haloalkoxy;

$R^2$ is selected from heteroaryl, lower cycloalkyl, lower cycloalkenyl, and aryl, wherein the heteroaryl, lower cycloalkyl, lower cycloalkenyl, and aryl radicals are substituted with one or more radicals independently selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and $R^5$ is selected from lower alkyl and amino;

or a pharmaceutically-acceptable salt thereof.

8. Compound of claim 6 wherein $R^1$ is lower haloalkyl, or $R_1$ is lower aralkylsulfonyl, lower arylthioalkyl, heteroarylalkoxyalkyl, lower heteroaryloxyalkyl, lower heteroarylthioalkyl, lower heteroarylalkylthioalkyl, lower aralkylthio, and lower aralkoxy, each of which is unsubstituted or substituted with one or more groups independently selected from halo, lower alkyl, lower alkoxy, lower alkylthio, and lower alkylsulfinyl;

$R^2$ is selected from heteroaryl, cycloalkyl and aryl, wherein the heteroaryl, cycloalkyl and aryl radicals are substituted at substitutable positions with one or more radicals independently selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, phenylamino and nitro; and $R^5$ is selected from lower alkyl and amino;

or a pharmaceutically-acceptable salt thereof.

9. A compound of the formula

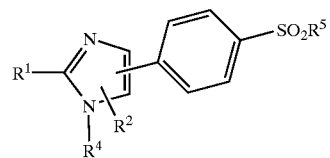

wherein $R^1$ is selected from lower haloalkyl, lower aralkyl, lower heterocyclicalkyl, lower heteroaralkyl, lower arylsulfonyl, lower arylcarbonyl, lower aralkylcarbonyl, lower aralkenyl, lower aminoalkyl, lower alkylaminoalkyl, lower N-arylaminoalkyl, lower N-alkyl-N-arylaminoalkyl, lower aralkoxy, lower aralkylthio, phenylsulfonyl, lower aralkylsulfonyl, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower arylthio, aryloxy, lower aralkylthioalkyl, lower aralkoxyalkyl, lower alkoxyaralkoxyalkyl, aryl and heteroaryl, wherein the aryl and heteroaryl radicals are unsubstituted or substituted with one or more radicals independently selected from halo, lower alkylthio, lower alkylsulfinyl, lower alkyl, cyano, lower haloalkyl, lower hydroxyl, lower alkoxy, lower hydroxyalkyl and lower haloalkoxy;

$R^2$ is selected from heteroaryl, lower cycloalkyl, lower cycloalkenyl, and aryl, wherein the heteroaryl, lower cycloalkyl, lower cycloalkenyl, and aryl radicals are substituted with one or more radicals independently selected from hydrido, halo, lower alkylthio, lower alkylsulfinyl, lower alkylsulfonyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro;

$R^4$ is selected from lower alkyl and acyl; and $R^5$ is selected from lower alkyl and amino;

or a pharmaceutically-acceptable salt thereof.

10. A pharmaceutical composition comprising a therapeutically-effective amount of a compound, said compound selected from a family of compounds of claim 1; or a pharmaceutically-acceptable salt thereof.

11. A pharmaceutical composition comprising a therapeutically-effective amount of a compound, said compound selected from a family of compounds of claim 2; or a pharmaceutically-acceptable salt thereof.

12. A pharmaceutical composition comprising a therapeutically-effective amount of a compound, said compound selected from a family of compounds of claim 3; or a pharmaceutically-acceptable salt thereof.

13. A pharmaceutical composition comprising a therapeutically-effective amount of a compound, said compound selected from a family of compounds of claim 4; or a pharmaceutically-acceptable salt thereof.

14. A pharmaceutical composition comprising a therapeutically-effective amount of a compound, said compound selected from a family of compounds of claim 5; or a pharmaceutically-acceptable salt thereof.

15. A pharmaceutical composition comprising a therapeutically-effective amount of a compound, said compound selected from a family of compounds of claim 6; or a pharmaceutically-acceptable salt thereof.

16. A pharmaceutical composition comprising a therapeutically-effective amount of a compound, said compound selected from a family of compounds of claim 7; or a pharmaceutically-acceptable salt thereof.

17. A method of treating inflammation or an inflammation-associated disorder in a subject, said method comprising administering to the subject having or susceptible to such inflammation or inflammation-associated disorder, a therapeutically-effective amount of a compound of claim 1; or a pharmaceutically-acceptable salt thereof.

18. A method of treating inflammation or an inflammation-associated disorder in a subject, said method comprising administering to the subject having or susceptible to such inflammation or inflammation-associated disorder, a therapeutically-effective amount of a compound of claim 2; or a pharmaceutically-acceptable salt thereof.

19. A method of treating inflammation or an inflammation-associated disorder in a subject, said method comprising administering to the subject having or susceptible to such inflammation or inflammation-associated disorder, a therapeutically-effective amount of a compound of claim 3; or a pharmaceutically-acceptable salt thereof.

20. A method of treating inflammation or an inflammation-associated disorder in a subject, said method comprising administering to the subject having or susceptible to such inflammation or inflammation-associated disorder, a therapeutically-effective amount of a compound of claim 4; or a pharmaceutically-acceptable salt thereof.

21. A method of treating inflammation or an inflammation-associated disorder in a subject, said method comprising administering to the subject having or susceptible to such inflammation or inflammation-associated disorder, a therapeutically-effective amount of a compound of claim 5; or a pharmaceutically-acceptable salt thereof.

22. A method of treating inflammation or an inflammation-associated disorder in a subject, said method comprising administering to the subject having or susceptible to such inflammation or inflammation-associated disorder, a therapeutically-effective amount of a compound of claim 6; or a pharmaceutically-acceptable salt thereof.

23. A method of treating inflammation or an inflammation-associated disorder in a subject, said method comprising administering to the subject having or susceptible to such inflammation or inflammation-associated disorder, a therapeutically-effective amount of a compound of claim 9; or a pharmaceutically-acceptable salt thereof.

24. The method of claim 17 for use in treatment of inflammation.

25. The method of claim 17 for use in treatment of an inflammation-associated disorder.

26. The method of claim 25 wherein the inflammation-associated disorder is arthritis.

27. The method of claim 25 wherein the inflammation-associated disorder is pain.

28. The method of claim 25 wherein the inflammation-associated disorder is fever.

* * * * *